US007176290B2

(12) United States Patent
Mandelkow et al.

(10) Patent No.: US 7,176,290 B2
(45) Date of Patent: Feb. 13, 2007

(54) TOOLS FOR THE DIAGNOSIS AND TREATMENT OF ALZHEIMER'S DISEASE

(75) Inventors: Eva-Marie Mandelkow, Hamburg (DE); Eckhard Mandelkow, Hamburg (DE); Birgit Lichtenberg-Kraag, Bärenklau (DE); Jacek Biernat, Hamburg (DE); Gerard Drewes, Hamburg (DE); Barbara Steiner, Ludwigshafen (DE)

(73) Assignee: Max-Planck-Gesellschaft zur Forderungder Wissenshaften, E.V., Munich (DE)

( * ) Notice: Subject to any disclaimer, the term of this patent is extended or adjusted under 35 U.S.C. 154(b) by 0 days.

(21) Appl. No.: 10/066,810

(22) Filed: Feb. 4, 2002

(65) Prior Publication Data

US 2002/0188106 A1 Dec. 12, 2002

Related U.S. Application Data

(62) Division of application No. 09/640,737, filed on Aug. 17, 2000.

(30) Foreign Application Priority Data

| Dec. 6, 1991 | (DE) | ................................. 91 12 0974 |
| Nov. 16, 1992 | (DE) | ................................. 92 11 9551 |
| Dec. 7, 1992 | (EP) | ....................... PCT/EP92/02829 |

(51) Int. Cl.
| C07K 16/00 | (2006.01) |
| C12P 21/08 | (2006.01) |
| C12N 5/06 | (2006.01) |
| C12N 5/16 | (2006.01) |
| C12N 5/00 | (2006.01) |

(52) U.S. Cl. ................................ 530/388.1; 530/387.1; 530/389.1; 530/387.9; 530/388.5; 435/326; 435/331

(58) Field of Classification Search ............. 530/387.1, 530/387.9, 388.1, 388.15; 435/7.1, 7.21, 435/7.9
See application file for complete search history.

(56) References Cited

FOREIGN PATENT DOCUMENTS

| EP | 475 295 A3 | 11/1991 |
| WO | WO 89/03993 | 5/1989 |
| WO | WO 93/03148 | 2/1993 |

OTHER PUBLICATIONS

Aizawa, et al., "Microtubule-binding Domain of Tau Proteins*", *J.Biol.Chem.* 263:7703-7707 (1988).
Biernat, et al., "The switch of tau protein to an Alzheimer-like state includes the phosphorylation of two serine—proline motifs upstream of the microtubule binding region", *EMBO J.* 11:1593-1597 (1992).
Binder, et al., "The Distribution of Tau in the Mammalian Central Nervous System", *J.Cell Biol.* 101:1371-1378 (1985).
Cleveland, et al., "Physical and Chemical Properties of Purified Tau Factor and the Role of Tau in Microtubule Assembly", *J.Mol.Biol.* 161:227-247 (1977).
Crowther and Wischik, "Image reconstruction of the Alzheimer paired helical filament", *EMBO J.* 4:3661-3665 (1985).
de Miguel, et al., "Molecular Analysis of Microtubule-Associated Protein-2 Kinase cDNA from Mouse and Rat Brain", *DNA and Cell Biology* 10:505-514 (1991).
de Garcini and Avila, "*In Vitro* Conditions for the Self-Polymerization of the Microtubule-Associated Protein, Tau Factor", *J.Biochem* 102:1415-1421 (1987).
Dignus, et al., "Use of a Heat-stable Microtubule-associated Protein Class-specific Antibody to Investigate the Mechanism of Microtubule Binding*", *J.Biol.Chem.* 266:18854-18860 (1991).
Geahlen, et al., "Detection of Protein Kinase Activity in Sodium Dodecyl Sulfate-Polyacrylamide Gels[1]", *Anal.Biochem* 153:151-158 (1986).
Geisler, et al., "Location and sequence characterization of the major phosphorylation sites of the high molecular mass neurofilament proteins M and H", *FEBS Letters* 221:403-407 (1987).
Goedert, et al., "Neurofibrillary tangles and β-amyloid deposits in Alzheimer's disease", *Current Opinion in Neurobiology* 1:441-447 (1991).
Goedert, et al., "Multiple Isoforms of Human Microtubule-Associated Protein Tau: Sequences and Localization in Neurofibrillary Tangles of Alzheimer's Disease", *Neuron* 3:519-526 (1989).
Goedert, et al., "Cloning and sequencing of the cDNA encoding a core protein of the paired helical filament of Alzheimer disease: Identification as the microtubule-associated protein tau", *Proc.Natl.Acad.Sci.(USA)* 85:4051-4055 (1988).
Greenberg and Davies, "A preparation of Alzheimer paired helical filaments that displays distinct τ proteins by polyacrylamide gel electrophoresis", *Proc.Natl.Acad.Sci.(USA)* 87:5827-5831 (1990).
Grundke-Iqbal, et al., "Abnormal phosphorylation of the microtubule-associated protein τ (tau) in Alzheimer cytoskeletal pathology", *Proc.Natl.Acad.Sci.(USA)* 83:4913-4917 (1986).
Hagestedt, et al., "Tau Protein Becomes Long and Stiff Upon Phosphorylation: Correlation between Paracrystalline Structure and Degree of Phosphorylation", *J.Cell Biol.* 109:1643-1651 (1989).

(Continued)

*Primary Examiner*—Olga N. Chemyshev
(74) *Attorney, Agent, or Firm*—Marshall, Gerstein & Borun LLP

(57) ABSTRACT

The present invention relates to phosphorylated tau protein epitopes associated with Alzheimer's disease, to protein kinases responsible for tau protein epitope phosphorylation, and to antibodies specific for the tau epitopes. Additionally, the present invention relates to pharmaceutical compositions, methods for detection, and methods of testing drugs effective in dissolving paired helical filaments associated with Alzheimer's disease.

5 Claims, 55 Drawing Sheets

OTHER PUBLICATIONS

Figure 1B:
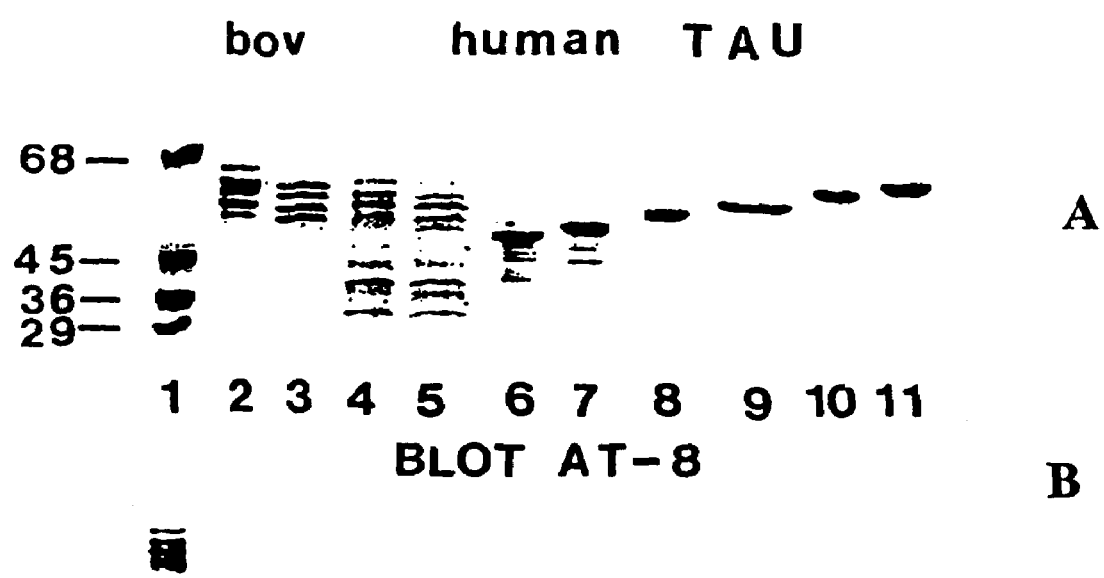

Higuchi, et al., "A general method of *in vitro* preparation and specific mutagenesis of DNA fragments: Study of protein and DNA interactions", *Nucl.Acids Res. 16*:7351-7367 (1988).

Himmler, et al., "Tau Consists of a Set of Proteins with Repeated C-Terminal Microtubule-Binding Domains and Variable N-terminal Domains", *Mol.Cell.Biol. 9*: 1381-1388 (1989).

Hirokawa, et al., "Tau Proteins: The Molecular Structure and Mode of Binding on Microtubules", *J.Cell Biol. 107*:1449-1459 (1988).

Hunter, "Protein Kinase Classification", *Meth.Enzymol 200*:3-37 (1991).

Ishiguro, et al., "Phosphorylation site son tau by tau protein kinase 1, a bovine derived kinase generating an epitope of paired helical filaments", *Neurosci.Lett. 148*:202-206 (1992).

Ishiguro, et al., "A Novel Tubulin-Dependent Protein Kinase Forming a Paired Helical Filament Epitope on Tau" *J.Biochem. 104*:319-321 (1988).

Ishiguro, et al., "A serine/threonine proline kinase activity is included in the tau protein kinase fraction forming a paired helical filament epitope", *Neurosci.Lett. 128*:195-198 (1991).

Ishiguro, et al., "Tau Protein Kinase I Converts Normal Tau Protein into A68-like Component of Paired Helical Filaments*", *J.Biol. Chem. 267*:10897-10901 (1992).

Jakes, et al., "Identification of 3- and 4-repeat tau isoforms within the PHF in Alzheimer's disease", *EMBO J. 10*:2725-2729 (1991).

Kosik, et al., "Epitopes That Span the Tau Molecule Are Shared with Paired Helical Filaments", *Neuron 1*:817-825 (1988).

Ksiezak-Reding, et al., "Alz 50, a Monoclonal Antibody to Alzheimer's Disease Antigen, Cross-reacts with τ Proteins from Bovine and Normal Human Brain*", *J.Biol.Chem. 263*:7943-7947 (1988).

Ledesma, et al., "Implication of brain cdc2 and MAP2 kinases in the phosphorylation of tau protein in Alzheimer's disease", *FEBS Letters 308*:218-224 (1992).

Lee, et al., A68: A Major Subunit of Paired Helical Filaments and Derivatized Forms of Normal Tau, *Science 251*:675-678 (1991).

Lichtenberg, et al., "Alzheimer-type Phosphorylation of Microtubule-Associated Protein Tau *In Vitro*", *J.Cell.Biol. 115*:3P2 (1991) (Abstract No. 2230).

Lichtenberg-Kraag and Mandelkow, "Isoforms of Tau Protein from Mammalian Brain and Avian Erythrocytes: Structure, Self-Assembly, and Elasticity", *J.Struct.Biol. 105*:46-53 (1990).

Lichtenberg-Kraag, et al., "Phosphorylation-dependent epitopes of neurofilament antibodies on tau protein and relationship with Alzheimer tau", *Proc.Natl.Acad.Sci.(USA) 89*:5384-5338 (1992).

Lindwall and Cole, "Phosphorylation Affects the Ability of Tau Protein to Promote Microtubule Assembly*", *J.Biol.Chem. 259*:5301-5303 (1984).

Nukina, et al., "Recognition of Alzheimer paired helical filaments by monoclonal neurofilament antibodies is due to crossreaction with tau protein", *Proc.Natl.Acad.Sci.(USA) 84*:3415-3419 (1987).

Rosenberg, et al., "Vectors for selective expression of cloned DNAs by T7 RNA polymerase", *Gene 56*:125-135 (1987).

Saiki, et al., "Primer-Directed Enzymatic Amplification of DNA with a Thermostable DNA Polymerase", *Science 239*:487-491 (1988).

Steiner, et al., "Phosphorylation of microtubule-associated protein tau: identification of the site for $Ca^{2+}$-calmodulin dependent kinase and relationship with tau phosphorylation in Alzheimer tangles", *EMBO J. 9*:3539-3544 (1990).

Sternberger, et al., Aberrant neurofilament phosphorylation in Alzheimer disease, *Proc.Natl.Acad.Sci.(USA) 82*:4274-4276 (1985).

Studier, et al., "Use of T7 RNA Polymerase to Direct Expression of Cloned Genes", *Meth.Enzymol. 185*:60-89 (1990).

VanBruggen, et al., "Two-dimensional crystallization experiments*", *J.Microsc. 141*:11-20 (1986).

Vandenheede et al., "APT•Mg-dependent Protein Phosphatase from Rabbit Skeletal Muscle", *J.Biol.Chem. 255*:11768-11774 (1980).

Vulliet, et al., "Proline-directed Phosphorylation of Human Tau Protein*", *J.Biol.Chem. 267*:22570-22574 (1992).

Wischik, et al., "Subunit Structure of Paired Helical Filaments in Alzheimer's Disease", *J.Cell Biol. 100*:1905-1912 (1985).

Wolozin, et al., "A Neuronal Antigen in the Brains of Alzheimer Patients", *Science 232*:648-650 (1986).

```
                  10        20        30        40
                   |         |         |         |
         MAEPROEFEVMEDHAGTYGLGDRKDQGGYTMHQDQEGDTDAGLK
           50        60        70            80        90       100
            •         •         |•            |         |         |
         ESPLQTPTEDGSEEPGSETSDAKSTPTAE    DVTAPLVDEGAPGKQAAAQPHTEIPEGTT
              110       120       130       140       150
               |•        |         |         |         |•
         AEEAGIGDTPSLEDEAAGHVTQARMVSKSKDGTGSDDKKAKGADGKTKIATPRGAAP
           160       170       180       190       200       210
            |         |         •         |•        |        •|••      |•
         PGQKGQANATRIPAKTPPAPKTPPSSGEPPKSGDRSGYSSPGSPGTPGSRSRTPSLP
            220       230       240
           •|         |•   •     |
         TPPTREPKKVAVVRTPPKSPSSAKSRL
```

```
              250       260       270
               |         |—        |
         QTAPVPMPDLKNVKSKIGSTENLKHQPGGGK
              280       290       300
               |         |—        |
         VQIINKKLDLSNVQSKCGSKDNIKHVPGGGS
              310       320       330
               |         |—        |
         VQIVYKPVDLSKVTSKCGSLGNIHHKPGGGQ
              340       350       360
               |         |—        |
         VEVKSEKLDFKDRVQSKIGSLDNITHVPGGGN
```

```
         370       380       390       400
          |         |         |•        |•
         KKIETHKLTFRENAKAKTDHGAEIVYKSPVVSGDTSPR
           410       420       430       440
            |         |•        |         |
         HLSNVSSTGSIDMVDSPQLATLADEVSASLAKQGL
```

FIGURE 1A ht$_{23}$ ht$_{24}$ ht$_{34}$ ht$_{39}$ ht$_{40}$

+Pi  +Pi  +Pi  +Pi  +Pi

BLOT AT-8

1  2  3  4  5  6  7  8  9  10

FIGURE 7A
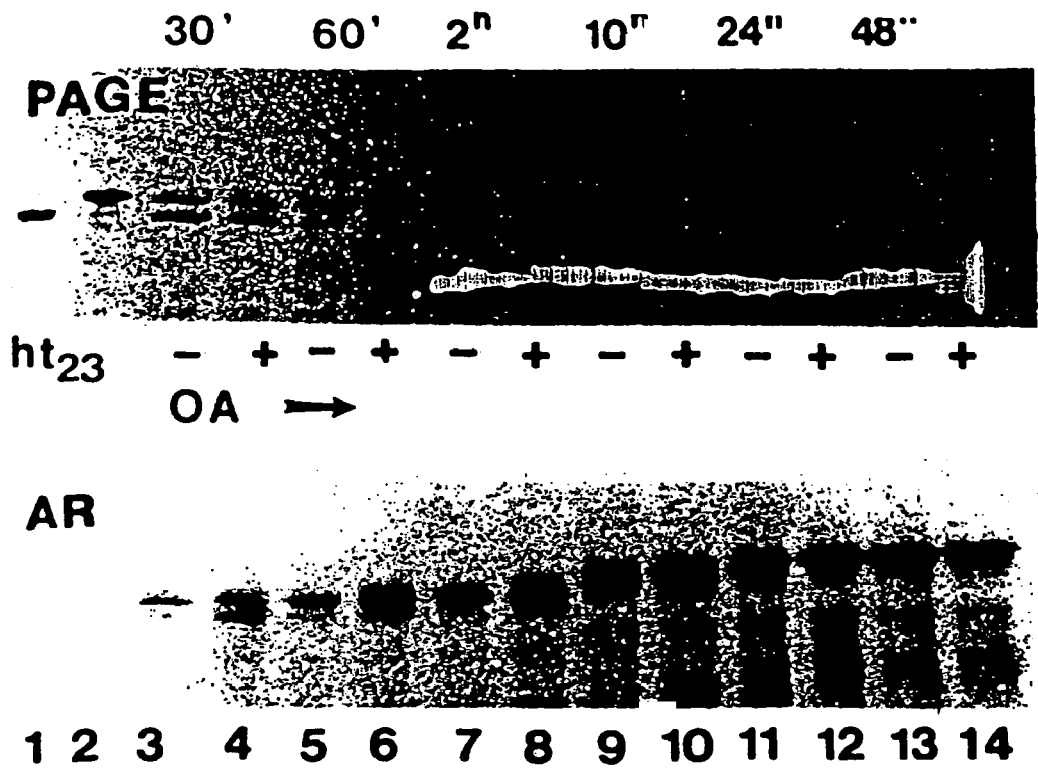
FIGURE 7B
FIGURE 8A
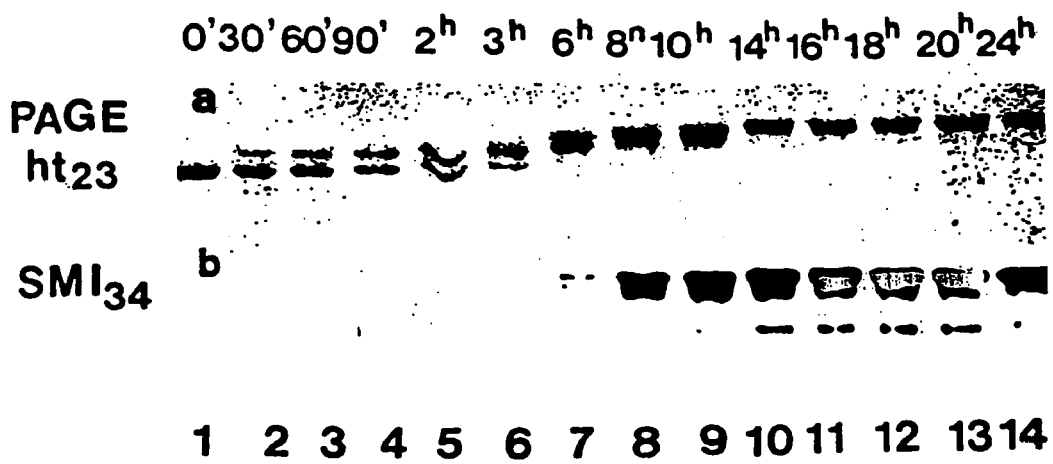
FIGURE 8B ht PHF-t

SMI₃₁

SMI₃₃

SMI₃₄

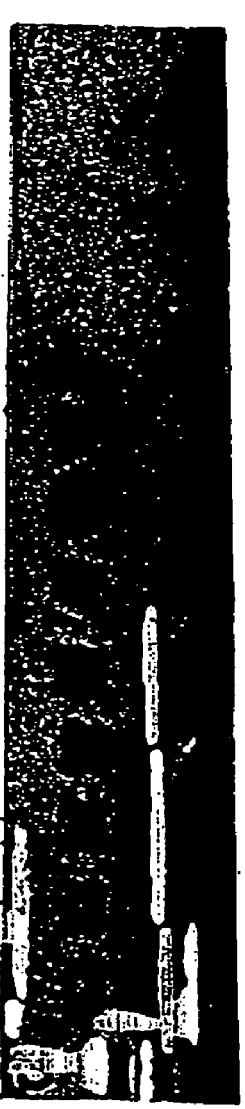
FIGURE 13A
FIGURE 13B
FIGURE 13C
FIGURE 13D

T-1

AT-8

$SMI_{35}$
$ht_{34}$ $SMI_{310}$

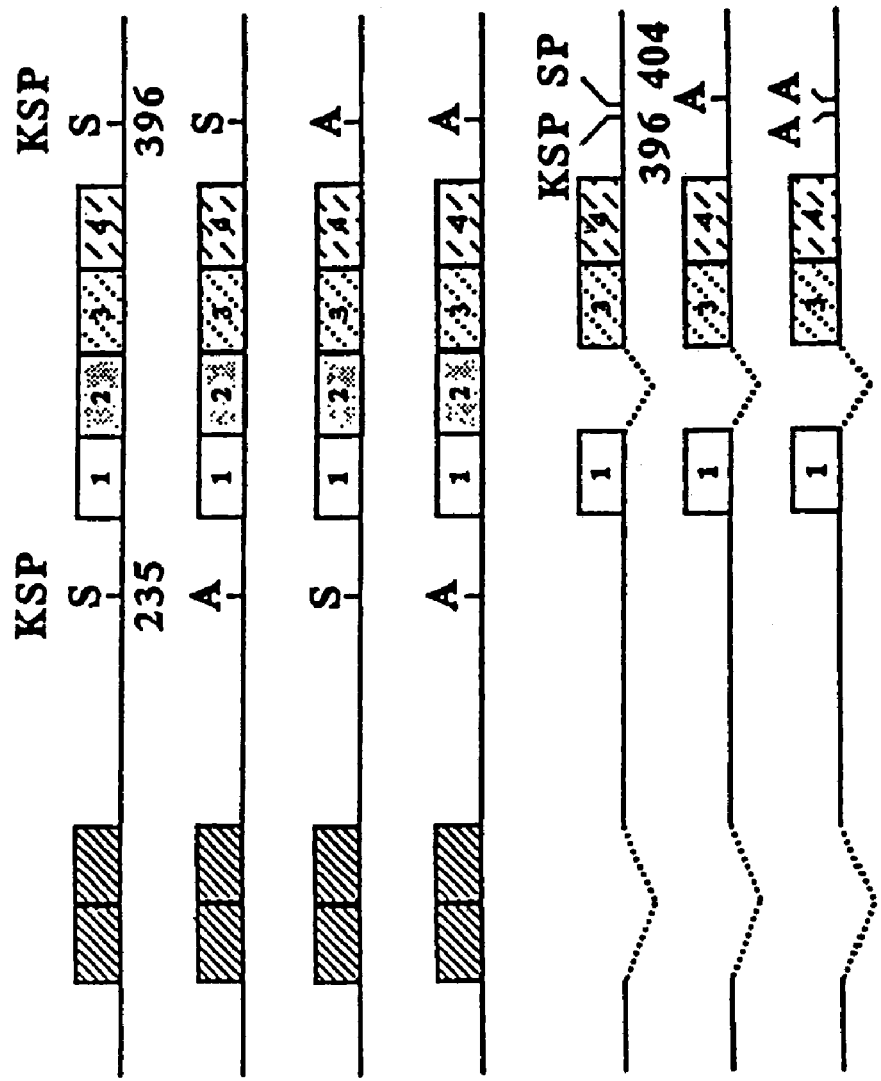

FIGURE 14A
FIGURE 14C
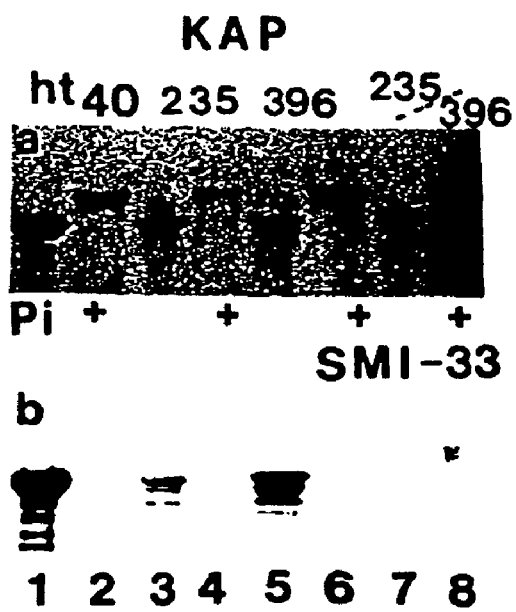
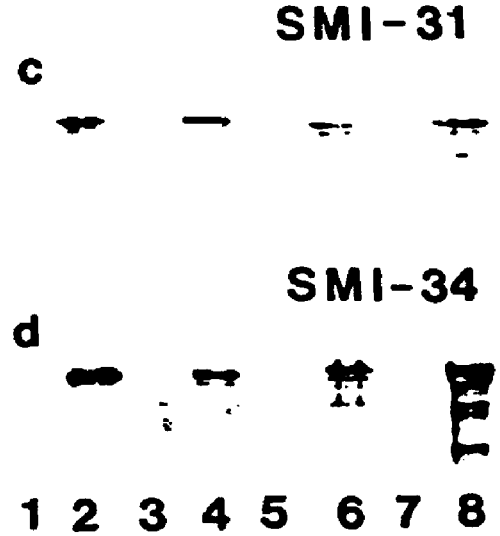
FIGURE 14B
FIGURE 14D
FIGURE 16A
FIGURE 16C
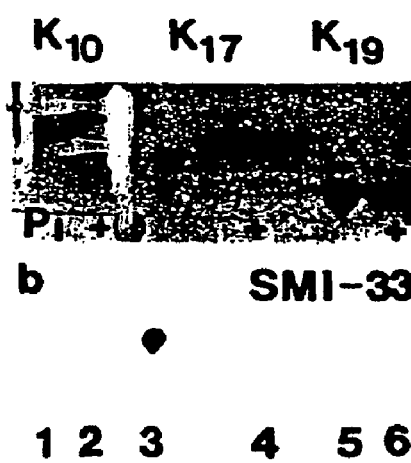
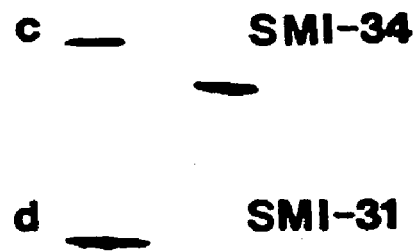
FIGURE 16B
FIGURE 16D

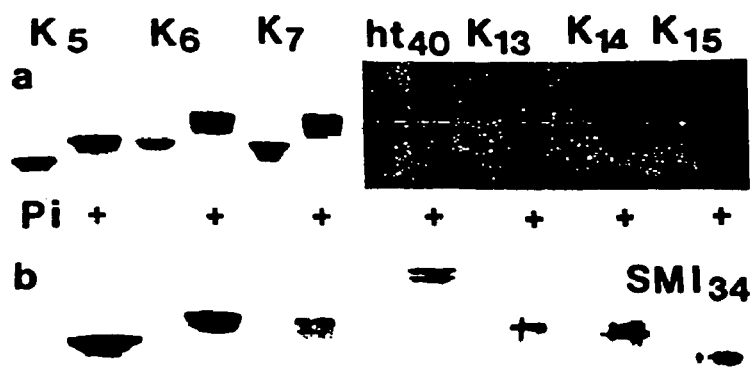
FIGURE 17A
FIGURE 17B
FIGURE 17C
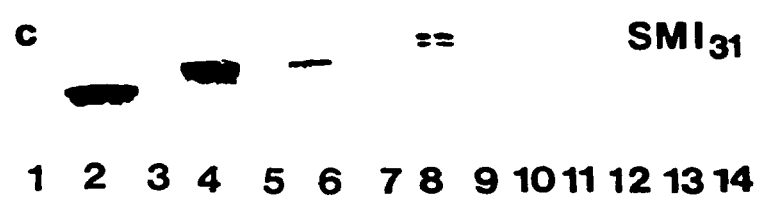
FIGURE 17D FIGURE 17E FIGURE 17F

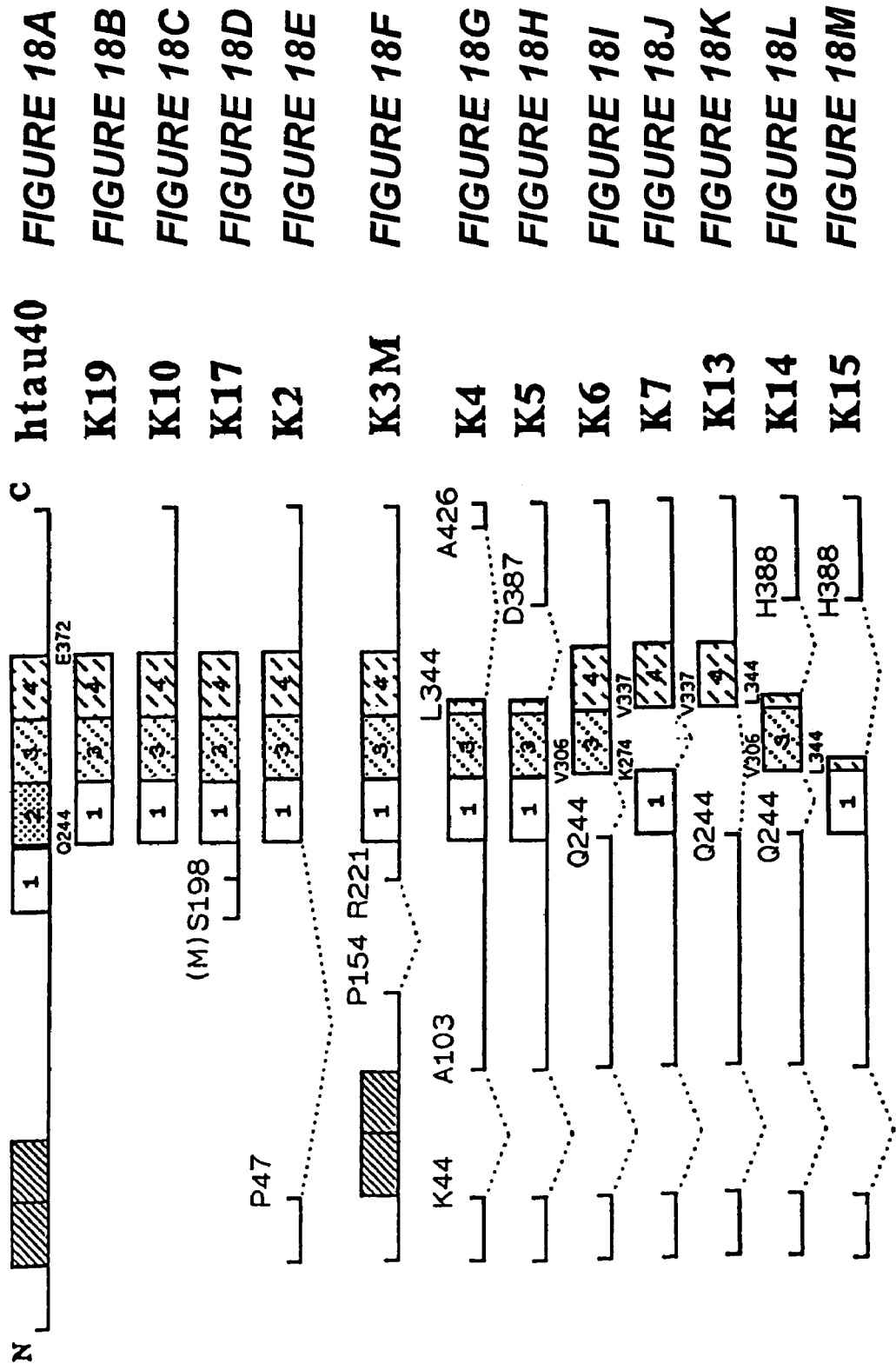

FIGURE 19A T8R-1
FIGURE 19B T8R-2
FIGURE 19C T7R-2
FIGURE 19D htau40
FIGURE 19E htau23
FIGURE 19F K11
FIGURE 19G K12

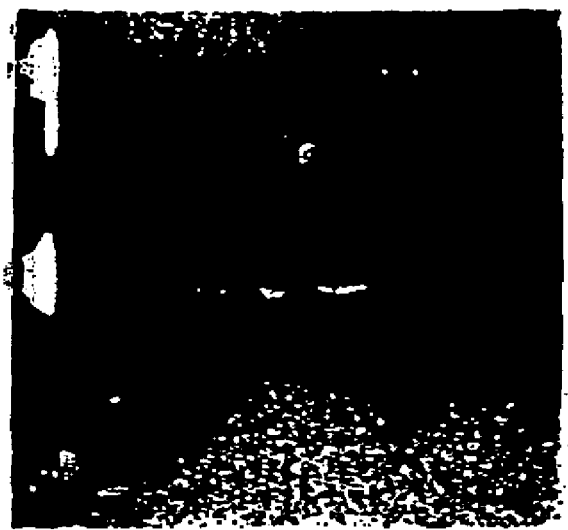
FIGURE 21F
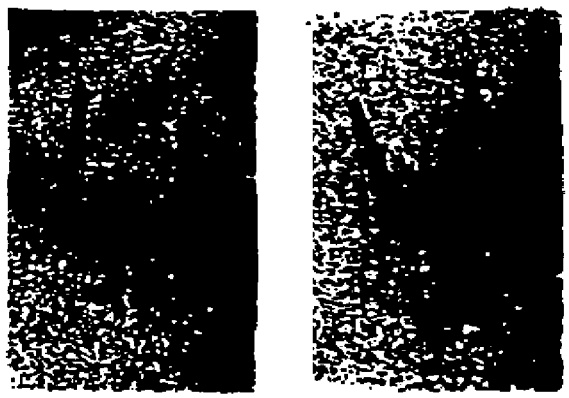
FIGURE 21H
FIGURE 21I
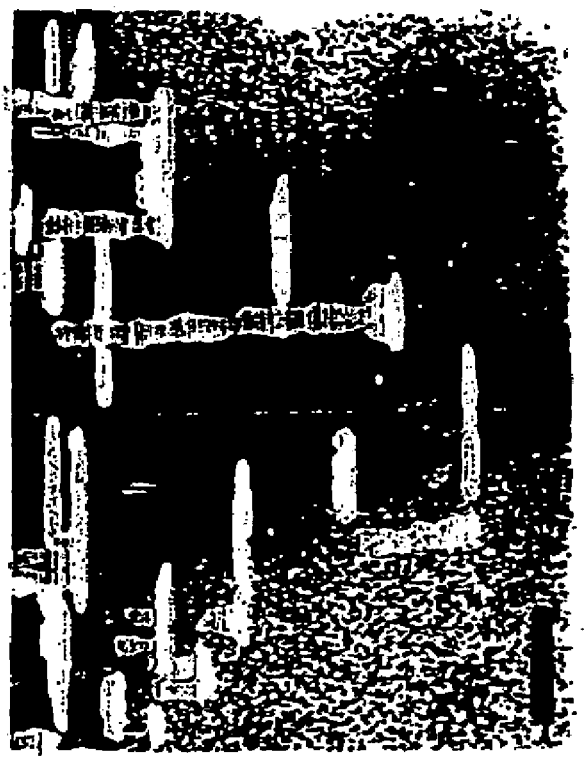
FIGURE 21G

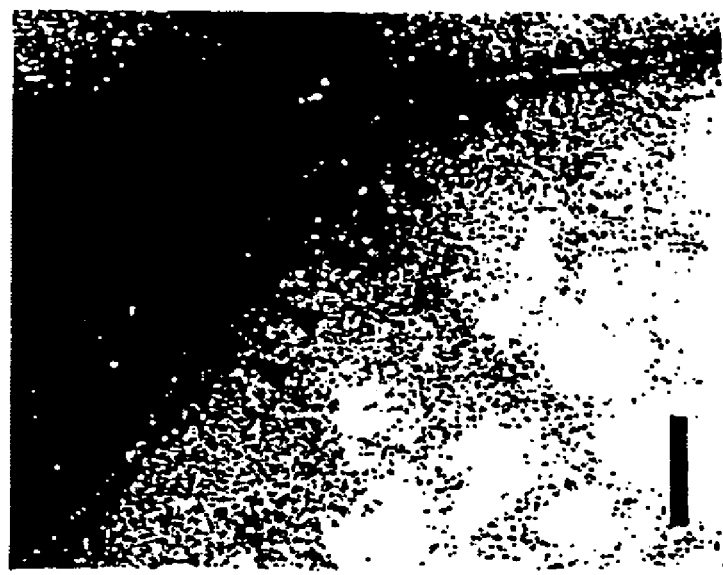
FIGURE 22A FIGURE 22B FIGURE 22C
PHFs from K12 PDM dimers

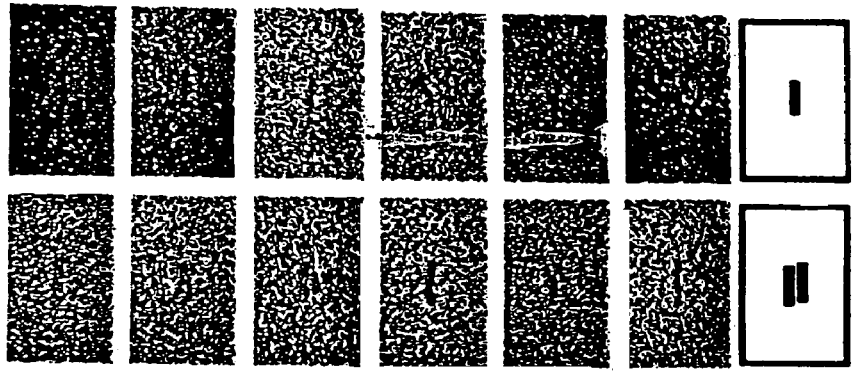
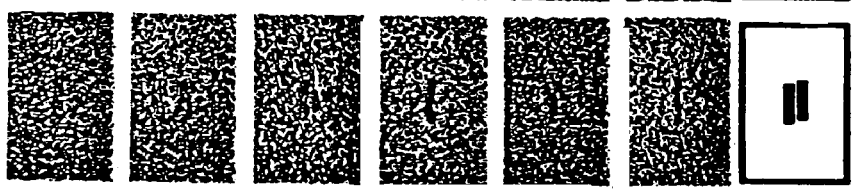
FIGURE 24A
FIGURE 24B
HTau23
FIGURE 24C
FIGURE 24D
FIGURE 24E
T8R-1

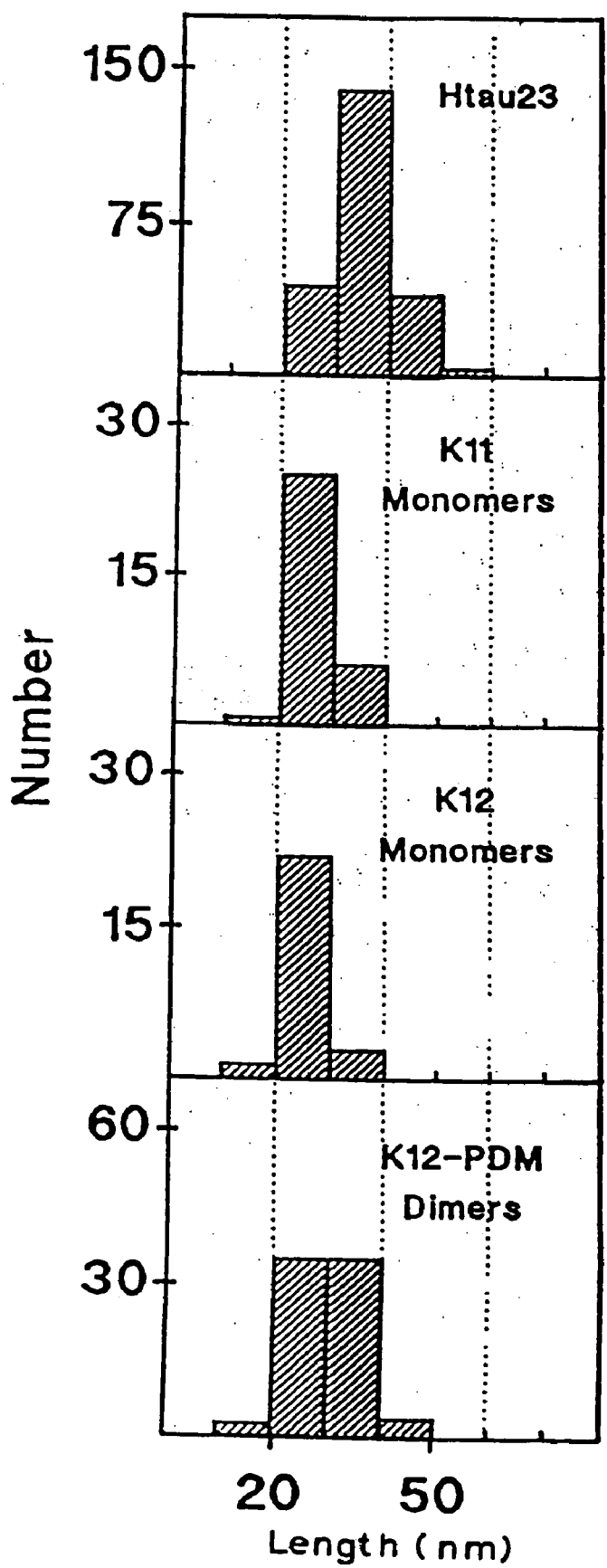

K11

K12

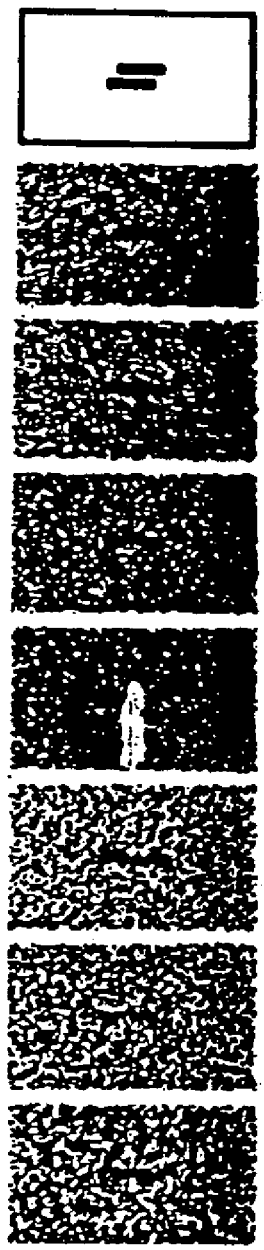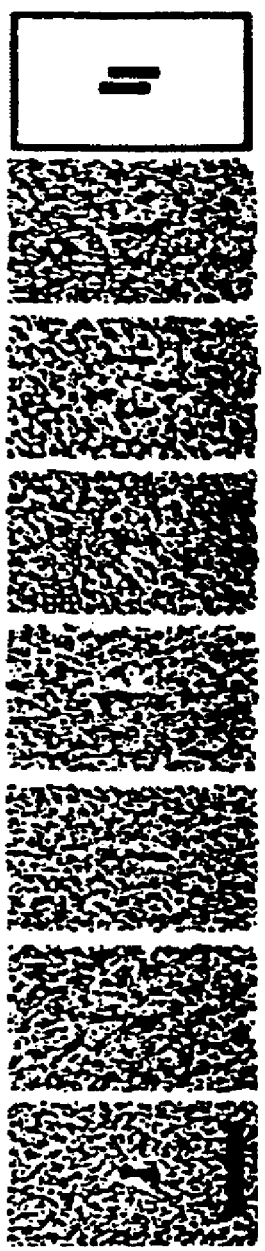
FIGURE 27A — K12 PDM Dimer
FIGURE 27B — K12 MBS Dimer

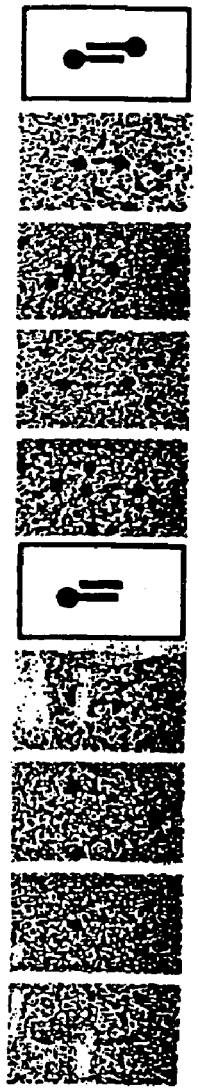
FIGURE 28A  Htau23 + AB2-4
FIGURE 28B  K12 + AB2-4
FIGURE 28C  K12 PDM dimer + AB2-4
FIGURE 28D  K12 MBS dimer + AB2-4

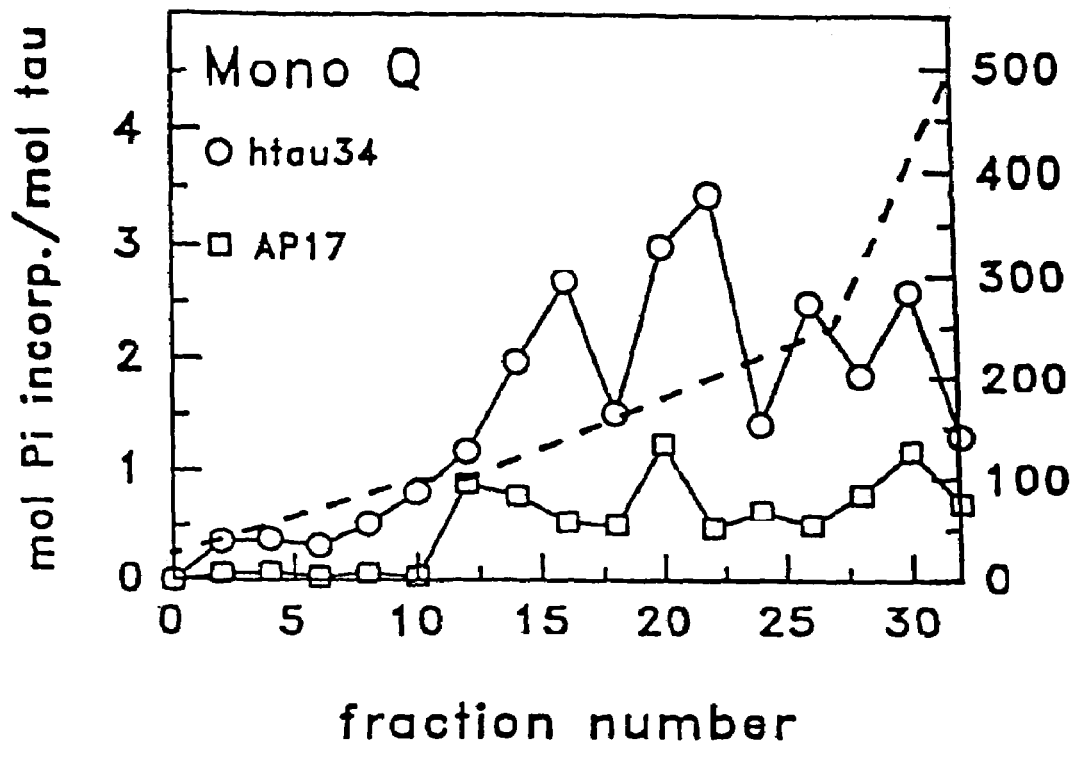
FIGURE 38A
FIGURE 38B
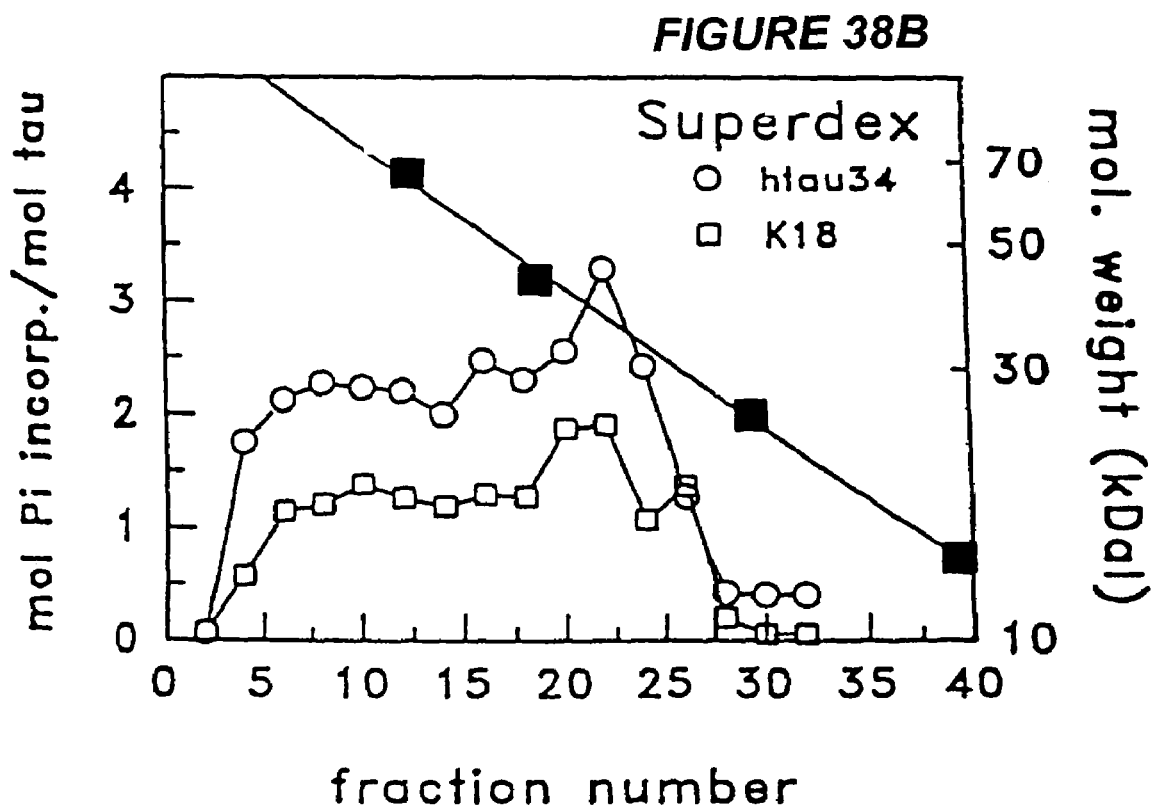

1 2 3 4

1 2 3 4 5 6

1 PAGE

2 AR

3 TAU-1

4 AT-8

| LANE | 1 | 2 | 3 | 4 | 5 | 6 | 7 | 8 | 9 |
|---|---|---|---|---|---|---|---|---|---|
| TIME (h) | 0 | 0.2 | 0.5 | 1.5 | 3 | 6 | 10 | 24 | 0 |

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 441 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

```
Met Ala Glu Pro Arg Gln Glu Phe Glu Val Met Glu Asp His Ala Gly
  1               5                  10                  15

Thr Tyr Gly Leu Gly Asp Arg Lys Asp Gln Gly Gly Tyr Thr Met His
             20                  25                  30

Gln Asp Gln Glu Gly Asp Thr Asp Ala Gly Leu Lys Glu Ser Pro Leu
         35                  40                  45

Gln Thr Pro Thr Glu Asp Gly Ser Glu Glu Pro Gly Ser Glu Thr Ser
     50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Gly
                 85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415
```

-continued

```
Ile Asp Met Val Asp Ser Pro Gln Leu Ala Thr Leu Ala Asp Glu Val
            420                 425                 430

Ser Ala Ser Leu Ala Lys Gln Gly Leu
        435                 440
```

TOOLS FOR THE DIAGNOSIS AND TREATMENT OF ALZHEIMER'S DISEASE

This is a Divisional of U.S. application Ser. No. 09/640,737, filed Aug. 17, 2000.

The invention relates to epitopes of the tau protein which are specifically occurring in a phosphorylated state in tau protein from Alzheimer paired helical filaments, to protein kinases which are responsible for the phosphorylation of the amino acids of the tau protein giving rise to said epitopes, and to antibodies specific for said epitopes. The invention further relates to pharmaceutical compositions for the treatment or prevention of Alzheimer's disease, to diagnostic compositions and methods for the detection of Alzheimer's disease and to the use of said epitopes for the generation of antibodies specifically detecting Alzheimer tau protein. Additionally, the invention relates to methods for testing drugs effective in dissolving Alzheimer paired helical filaments or preventing the formation thereof.

The brains of Alzheimer patients contain two characteristic types of protein deposits, the plaques and the tangles. These structures have been of peak importance in Alzheimer research during the last few years (for a recent review see Goedert et al., Current Opinion in Neurobiology 1 (1991), 441 to 447). A prominent component of the tangles are the paired helical filaments (PHFs). It seems now clear that the PHFs are largely made up of the microtubule-associated protein tau which is normally attached to the neuronal microtubule network and, furthermore, particularly enriched in the axons.

There are six isoforms of tau in human brain that arise from alternative splicing of a single gene. All these isoforms also occur in PHFs (Goedert et al., Neuron 3 (1989), 519–526). The main biochemical differences between normal and Alzheimer PHF tau protein known so far may be summarized as follows:

(1) PHF tau protein is, in contrast to normal tau protein, highly insoluble which makes a biochemical analysis difficult;

(2) PHF tau protein reacts with certain antibodies in a phosphorylation dependent manner, suggesting a special phosphorylation status (Grundke-Iqbal et al., Proc. Natl. Acad. Sci. USA 83 (1986), 4913–4917, Nukina et al., Proc. Natl. Acad. Sci. USA 84 (1987), 3415–3419);

(3) PHF tau protein has a lower electrophoretic mobility in SDS gels, suggesting a higher $M_r$ value which may be related to its phosphorylation pattern (Steiner et al., EMBO J. 9 (1990), 3539–3544);

(4) PHF tau protein forms paired helical filaments with a characteristic 78 nm crossover repeat (Crowther and Wischik, EMBO J. 4 (1985), 3661–3665).

Tau protein purified from brain has very little secondary structure (as judged by CD spectroscopy), and a sedimentation constant of 2.6S, pointing to a highly asymmetric shape (Cleveland et al., J. Mol. Biol. 1161 (1977), 227–247, in agreement with electron microscopic data (Hirokawa et al., J. Cell. Biol. 107 (1988), 1449–1459. The C-terminal half contains 3 or 4 internal repeats which are involved in microtubule binding and promoting their assembly (hence "assembly domain"). This domain can be phosphorylated by several protein kinases (Steiner et al., EMBO J. 9 (1990), 3539–3544), a point that may be significant in view of the abnormal phosphorylation of Alzheimer tau (see, e.g. Grundke-Iqbal et al., ibid.). Moreover, the repeat region also lies in the core of Alzheimer paired helical filaments (see, e.g. Goedert et al., ibid.; Jakes et al. EMBO J. 10(1991), 2725–2729).

It has been hypothesized that PHF tau protein has a lower affinity for microtubules compared to normal tau proteins since a similar effect has been found when normal tau is phosphorylated in vitro by some kinases (Lindwall and Cole, J. Biol. Chem. 259 (1984), 5301–5305). Lack or reduced binding to microtubules might therefore be a result of abnormal phosphorylation of the tau protein. This abnormal state might lead to microtubule disassembly and interfere with vital neuronal processes, such as rapid axonal transport. The abnormally phosphorylated tau proteins might then aggregate into PHFs. As a consequence thereof the neurons would eventually die thus setting the stage for the generation of the Alzheimer's disease.

Up to now, it was not known which protein kinases are responsible for the abnormal phosphorylation. Ishiguro et al. (Neuroscience Letters 128, (1991), 195–198) have isolated a kinase fraction from bovine brain extracts which contain a protein kinase recognizing the serine/threonine proline motif. This kinase phosphorylated residues Ser 144, Thr 147, Ser 177 and Ser 315 of the tau protein. These residues differed from the ones reported by others (Lee et al., Science 251 (1991), 675–678). Therefore, it remains unclear which protein kinase and which target amino acid residue(s) are involved in the generation of Alzheimer's disease, if at all.

It is, moreover, of utmost importance for the diagnosis of Alzheimer's disease, in particular at an early stage of the disease process, to develop antibodies which are specifically, directed to epitopes on the protein which are characteristic of the Alzheimer state. A monoclonal antibody, TAU1, has been isolated which is capable of distinguishing between phosphorylated and non-phosphorylated, forms of the tau protein (see, e.g., Lee et al., ibid.). However, this antibody specifically recognizes dephosphorylated tau protein which is seemingly not associated with the Alzheimer state. Another antibody, Alz 50 (Ksiezak-Reding et al., J. Biol. Chem. 263 (1988), 7943–7947) reacts with PHFs as well as with tau protein. Sternberger et al., Proc. Natl. Acad. Sci. USA 82 (1985), 4774–4776, have isolated an antibody, SMI 34, which recognizes a phosphorylated epitope common to Alzheimer tau protein and neurofilament protein. Finally, Lee et al. (ibid.) made antibodies directed to a phosphorylated peptide comprising the KSPV motif in the C-terminal region of the tau protein. All these antibodies known in the art have the disadvantage that for none of them it is known whether they recognize an epitope which is uniquely characteristic for the Alzheimer's disease state.

Furthermore, no reliable data on the fine structure of Alzheimer paired helical filaments, nor on the the mode or regulation of their formation from tau proteins is available so far. For the prevention of the formation of PHFs it would be highly advantageous if the mode of assembly of PHFs from tau protein and the regulatory mechanisms underlying said assembly were known.

Thus, the technical problem underlying the present invention was to provide a phosporylated epitope characteristic for the Alzheimer tau protein, a kinase activity which specifically catalyzes this phosphorylation, pharmaceutical compositions comprising inhibitors to said kinases, antibodies for recognizing said epitopes, diagnostic compositions containing said epitopes, methods involving kinases and/or antibodies for the in vitro diagnosis of Alzheimer's disease, methods for the in vitro conversion of normal tau protein into Alzheimer tau protein and methods for testing drugs effective in dissolving Alzheimer PHFs or preventing the formation thereof.

The solution to the above technical problem is achieved by providing the embodiments characterized in the claims.

Accordingly, the present invention relates to an epitope of the tau protein which is specifically occurring in a phosphorylated state in tau protein from Alzheimer paired helical filaments.

The term "phosphorylated state in tau proteins from Alzheimer paired helical filaments" refers to a state of the tau protein where tau shows an upward $M_r$ shift, has a reduced binding to microtubules and is phosphorylated at ser or thr followed by pro, or certain serines in the repeat region (see below).

Note: Amino acids are denoted by the one-letter or three-letter code; see e.g. Lehninger, Biochemistry, 2nd edition, Worth Publishers, New York, 1975, page 72.

There may be one or more epitopes of the tau protein which specifically occur in a phosphorylated state in Alzheimer paired helical filaments. These epitopes may, moreover, be phosphorylated by a single or different enzymes displaying phosphorylating activity.

In a preferred embodiment of the present invention, said epitopes are specifically phosphorylated by a protein kinase from mammalian brain having the following biochemical properties:
(a) it phosphorylates ser-pro and thr-pro motifs in tau protein;
(b) it has an $M_r$ of 42 kD;
(c) it is activated by ATP and has a $K_m$ of 1.5 mM;
(d) it is activated by tyrosine phosphorylation;
(e) it is recognized by an anti-MAP kinase antibody; and
(f) it is deactivated by phosphatase PP2a.

The term "ser-pro and thr-pro motifs" as used herein refers to a phosphorylatable ser or thr residue followed by a pro residue. These types of sites are phosphorylated by the isoforms of MAP kinase, GSK-3, and cdk2 (see below).

The term "anti-MAP kinase antibody" refers to an antibody which specifically recognizes a mitogen activated protein okinase (MAP kinase). This kinase probably belongs to a family of closely related enzymes which have been referred to in the art by different names, e.g. MAP2 (microtubule-associated protein 2, see e.g. de Miguel et al., DNA and Cell Biology 10 (1991), 505–514) kinase, MBP (myelin basic protein) kinase or ERK1 (for a review, see Hunter, Meth. Enzym. 200 (1991), 1–37). MAP kinase is similar with respect to its biochemical properties to functionally similar enzymes from a variety of sources (Hunter, ibid.).

In another preferred embodiment of the present invention said epitope includes the phosphorylatable serine residues 46, 199, 202, 235, 396, 404 and/or 422 and/or the phosphorylatable threonine residues 50, 69, 111, 153, 175, 181, 205, 212, 217 and/or 231; see FIG. 1a.

The numbering of the amino acids was done in line with the largest human tau isoform, htau 40, see Goedert et al. (1989 ibid.).

In a particularly preferred embodiment said epitope includes the phosphorylatable serine residue of amino acid position 262. This is phosphorylated by the brain extract and the 35 KD and 70 KD kinases prepared from it; see below. In accordance with the present invention it has been shown that phosphorylation of said residue significantly interferes with binding of tau protein to microtubuli. This epitope may be used for diagnostic in vitro methods to test for the onset of Alzheimer disease.

In another particularly preferred embodiment said epitope includes the phosphorylatable serine residues 262, 293, 324 and 409.

Accordingly, another object of the invention is to provide a method for testing the onset of Alzheimer disease by assaying the phosphorylation status of serine in position 262 and the other Ser-Pro or Thr-Pro motifs named above. This may e.g. be done by incubating a sample of cerebro-spinal fluid of a patient or a sample of nerve tissue after biopsy with a monoclonal or polyclonal antibody capable of distinguishing between a phosphorylated and a non-phosphorylated serine 262 comprising epitope.

The epitopes of the invention may comprise one or more of the residues enumerated above. Moreover, the epitopes of the present invention may comprise only one or more phosphorylated serine residues, one or more phosphorylated threonine residues or a combination thereof. The actual composition of the epitope may be determined by methods which are known in the art. It is also clear to the person skilled in the art that other amino acids of the protein may contribute to the epitope which is recognized by an antibody directed against the sites of tau protein which are phosphorylated by MAP kinase.

In a further preferred embodiment of the present invention, said epitope comprises the amino acid sequences KESPLQ (SEQ ID NO: 2), YSSPGSP (SEQ ID NO: 3), PGSPGT (SEQ ID NO: 4), YSSPGSPGTPGS (SEQ ID NO: 5), PKSPSS (SEQ ID NO: 6), YKSPVVS (SEQ ID NO: 7), GDTSPRH (SEQ ID NO: 8), MVDSPQL (SEQ ID NO: 9), PLQTPTE (SEQ ID NO: 10), LKESPLQTPTED (SEQ ID NO: 11), AKSTPTA (SEQ ID NO: 12), IGDTPSL (SEQ ID NO: 13), KIATPRGA (SEQ ID NO: 14), PAKTPPA (SEQ ID NO: 15), APKTPPS (SEQ ID NO: 16), PAKTPPAPKTPPS (SEQ ID NO: 17), SPGTPGS (SEQ ID NO: 18), RSRTPSL (SEQ ID NO: 19), SLPTPPT (SEQ ID NO: 20), RSRTPSLPTPPT (SEQ ID NO: 21), VVRTPPK (SEQ ID NO: 22), VVRTPPKSPSSA (SEQ ID NO: 23), KIGSTENLK (SEQ ID NO: 24), KCGSKDNIK (SEQ ID NO: 25), KCGSLGNIH (SEQ ID NO: 26), KIGSLDNITH (SEQ ID NO: 27).

Again, it is to be understood that not all of the amino acids of the peptide necessarily contribute to the specific site actually recognized by the antibody.

Another object of the present invention is to provide a protein kinase which is capable of specifically converting tau protein to Alzheimer tau protein by phosphorylation of the amino acid motif ser-pro or thr-pro.

Preferably, said protein kinase belongs to the class of MAP kinases. These kinases can be used for various purposes, e.g. for the in vitro conversion of tau protein into Alzheimer tau protein. The Alzheimer tau protein thus obtainable may be used to study e.g. substances which are capable of inhibiting its formation or the formation of PHFs. Moreover, they may be used for the development of drugs capable of dissolving said PHFs or for converting Alzheimer tau protein into normal tau protein. It is also conceivable that a system based on the ability of the protein kinase of the invention to convert normal into Alzheimer tau protein will provide a well defined in vitro system for Alzheimer's disease.

In a preferred embodiment of the invention, said protein kinase has the following biochemical properties:
(a) it phosphorylates ser-pro and thr-pro motifs in tau protein;
(b) it has an $M_r$ of 42 kD;
(c) it is activated by ATP and has a $K_m$ of 1.5 mM;
(d) it is activated by tyrosine phosphorylation;
(e) it is recognized by an anti-MAP kinase antibody; and
(f) it is deactivated by phosphatase PP2a.

The term "$M_r$" is defined as the relative molecular weight determined by SDS gel electrophoresis.

In still another preferred embodiment of the invention, said protein kinase is obtainable by carrying out the following steps:
(a) homogenizing porcine brain in 10 mM Tris-HCl, pH 7,2, 5 mM EGTA, 2 mM DTT and a cocktail of protease inhibitors (leupeptin, aprotinin, pepstatin A, α2-macroglobulin, PMSF (phenyl methyl sulphonyl fluoride));
(b) centrifugating the homogenate at 100,000×g for 30 minutes at 4° C.;
(c) removing the supernatant after centrifugation;
(d) precipitating the crude protein by ammonium sulfate precipitation;
(e) desalting the crude preparation by gel filtration;
(f) activating the crude enzyme by incubation in activation buffer;
(g) further purifying the crude preparation by ion exchange chromatography; and
(h) identifying the enzyme by Western blotting.

The term "activation buffer" is defined as a buffer comprising 25 mM Tris, 2 mM EGTA, 2 mM DDT, 40 mM p-nitrophenylphosphate, 10 μM okadaic acid, 2 mM MgATP, and protease inhibitors.

Another preferred embodiment of the present invention relates to a protein kinase which is capable of specifically converting tau protein to Alzheimer tau protein by phosphorylating IGS and/or CGS motifs in the repeat region of tau protein.

In a further preferred embodiment of the kinase of the invention, said kinase is obtainable by carrying out the following steps:
(A) Subjecting mammalian brain extract to ion exchange chromatography on Mono Q (Pharmacia);
(B) testing the fractions eluted for binding to microtubules and phosphorylation of the protein;
(C) further purifying the fractions binding to microtubules and capable of phosphorylating tau protein by gel chromatography;
(D) subjecting the fraction eluting at about 35 kDal to ion exchange chromatography on Mono Q;
(E) collecting the major peak eluting between 200 and 250 mM NaCl;
and has the following characteristics:
(a) it binds to Mono Q but not to Mono S;
(b) it has an acidic pI;
(c) it shows a major band (>95%) at 35 kDal and a minor band (<5%) at 41 kDal on silver-stained gels;
(d) it incorporates a phosphate amount of 3.2 Pi into htau34, 3.4 Pi into htau40, 3.3 Pi into htau23 and 2.8 Pi into mutant htau23 (Ser262→Ala); and
(e) it phosphorylates serine residues 262, 293, 324 and 409 of tau protein.

Said brain extract may e.g. be human or bovine brain extract.

In still another preferred embodiment, the kinase of the present invention is obtainable by the following steps:
(A) preparation of high spin supernatant of extract from mammalian brain;
(B) subjecting the brain extract to chromatography on ion exchange Q-Sepharose (Pharmacia);
(C) testing the fractions and flowthrough for phosphorylation of tau protein and influence on binding to microtubules;
(D) chromatography of flowthrough on S-Sepharose, wherein the kinase activity elutes at 250 mM NaCl;
(E) chromatography on heparin agarose, wherein the kinase activity elutes at 250 mM NaCl;
(F) gel filtration, wherein the kinase activity elutes at 70 kDal;
(G) chromatography on Mono Q, wherein the kinase activity elutes at 150 mM NaCl;
and has the following characteristics:
(a) it does not bind to Q-Sepharose but to S-Sepharose;
(b) it has an alkaline pI;
(c) it shows a major band around 70 kDal on SDS gels;
(d) it incorporates 3–4 phosphates into htau34, htau40, htau23, and the construct K19 (i.e., the four-repeat microtubule binding region);
(e) it does not phosphorylate a mutant of K19 where Ser 262, 293, 324, and 409 are mutated into Ala; and
(f) it phosphorylates Ser 262, 293, 324, and 409 or tau protein.

In another preferred embodiment of the invention, the 70 kDal kinase which phosphorylates the two IGS motifs and the two CGS motifs of tau protein (Serines 262, 293, 324, 409) may be obtained as follows:
(A) Preparation of high spin supernatant of brain extract;
(B) chromatography on Q-Sepharose;
(C) chromatography of flowthrough on S-Sepharose, wherein the kinase activity elutes at 250 mM NaCl;
(D) chromatography on heparin agarose, wherein the kinase activity elutes at 250 mM NaCl;
(E) gel filtration, wherein the kinase activity elutes at 70 kDal;
(F) chromatography on Mono Q, wherein the kinase activity elutes at 150 mM NaCl.

Figure 45A:
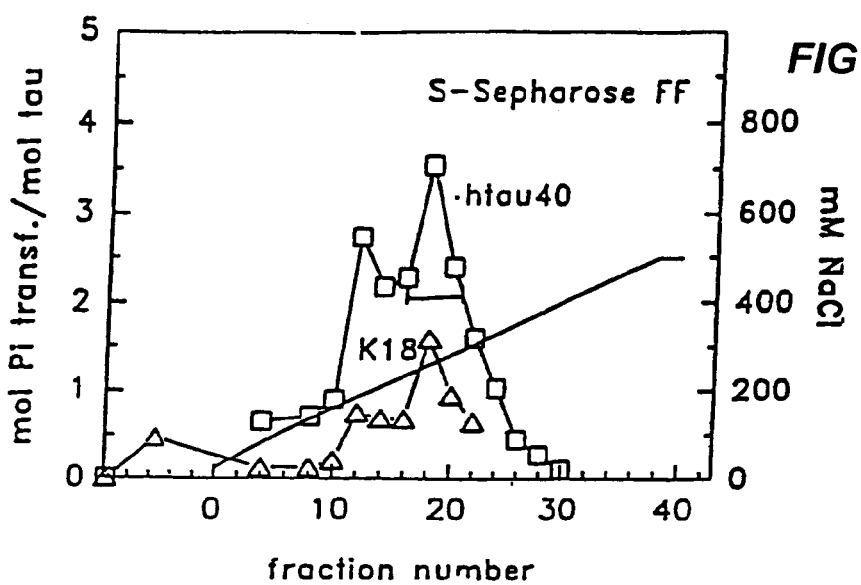
Figure 45B:
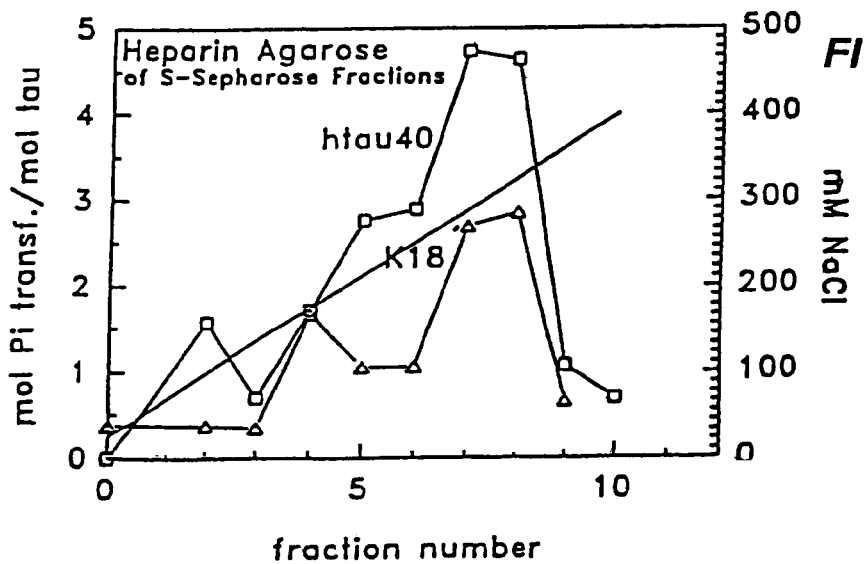
Figure 45C:
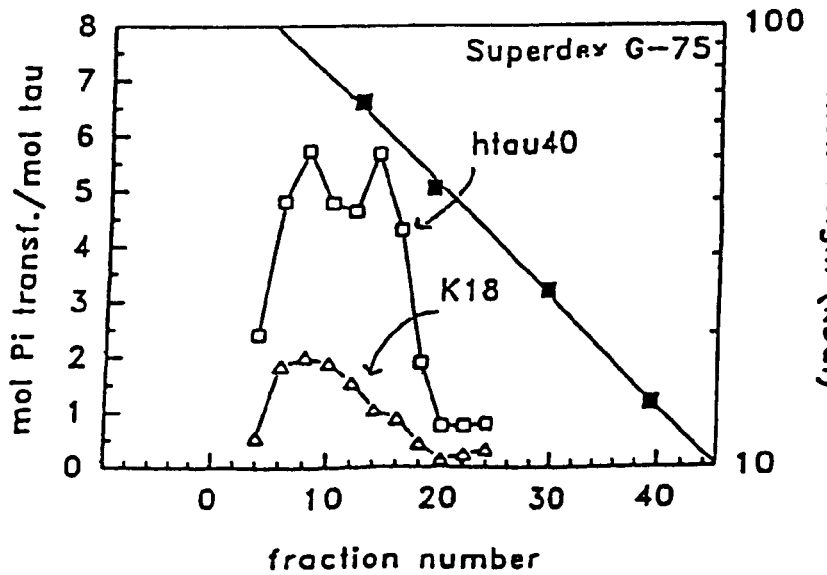
Figure 46A:
Figure 46B:
Figure 46C:
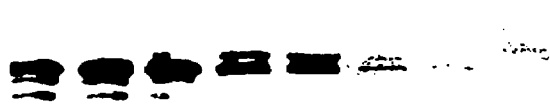
Figure 46D:

(See FIG. 45)

The brain extract in step A may be e.g. human or another mammalian brain extract.

The purification steps noted above are conventional ones known in the art as described throughout this specification. Thus, preparation of the brain extract was carried out as described in Example 11, whereas binding studies between tau and taxol-stabilized microtubules may be done as described in Example (6).

Furthermore, assays of tau-phosphorylation such as in-gel assays may be carried out as described in detail in Example 11.

Chromatography on Mono Q may be carried out as described in Example 11.

With respect to the actual conditions used for obtaining said kinase, a person skilled in the art will be able to deviate from the protocol outlined above and still obtain the kinase of the invention. Such a deviation may, e.g., concern the composition of the protease inhibitor cocktail of step (a): It is conceivable to use different inhibitors under the proviso that the kinase activity is not diminished or destroyed.

In a most preferred embodiment the present invention relates to a protein kinase which specifically phosphorylates serine residues 46, 199, 202, 235, 262, 396, 404, 422 and threonine residues 50, 69, 111, 153, 175, 181, 205, 212, 217, 231 of the tau protein.

In another most preferred embodiment, said kinase phosphorylates serine residue 262.

A further preferred embodiment relates to a protein kinase which is glycogen synthase kinase-3, that is, isoform α, 51 kD or β (45 kD) and/or cdk2-cyclin A (33 kD).

In another preferred embodiment of the present invention, said kinase is a protein kinase from human brain, porcine brain, or another source.

Another object of the invention is to provide pharmaceutical compositions containing a specific inhibitor for the protein kinase of the invention, optionally in combination with a pharmaceutically acceptable carrier and/or diluent.

The term "specific inhibitor for the protein kinase" refers to substances which specifically inhibit the enzymatic action of the protein kinase of the present invention. Inhibitors to enzymes such as protein kinases and their mode of action are well known in the art. For example, such an inhibitor may bind to the catalytic domain of the enzyme thus rendering it incapable of converting its substrate. Examples of such inhibitors are peptide inhibitors and deactivating phosphatases such as PP2a.

Another example is the deactivation of kinases by their phosphatases, e.g., PP-2a in the case of MAP kinase. Said pharmaceutical composition may be administered to a patient in need thereof by a route and in a dosage which is deemed appropriate by the physician familiar with the case. Pharmaceutically acceptable carriers and/or diluents are well known in the art and may be formulated according to the route of administration or the special disease status of the patient.

In a preferred embodiment the present invention relates to a pharmaceutical composition for use in the treatment of Alzheimer's disease.

Again, said pharmaceutical composition may be administered to a patient in need thereof by route and in a dosage which is deemed appropriate by the physician handling the case.

In another preferred embodiment of the present invention, said pharmaceutical composition contains as the specific inhibitor at least one oligo- or polypeptide comprising an epitope of the invention.

The term "oligo- or polypeptide comprising an epitope of the invention" refers to peptides which in their two- or three-dimensional structure reconstitute the epitope of the invention which is specifically recognized by an antibody directed thereto. Moreover, said oligo- or polypeptides may solely consist of the amino acids representing said epitope(s) or they may comprise additional amino acids. The construction of such oligo- or polypeptides is well known in the art.

Another object of the invention is an antibody which specifically recognizes an epitope of the invention.

Said antibody may be a serum derived or a monoclonal antibody. The production of both monoclonal and polyclonal antibodies to a desired epitope is well known in the art (see, e.g. Harlow and Lane, Antibodies, A Laboratory Manual, Cold Spring Harbor Laboratory, Cold Spring Harbor, 1988). Furthermore, said antibody may be a natural or an antibody derived by genetic engineering, such as a chimeric antibody derived by techniques which are well understood in the art. Moreover, said antibody also refers to a fragment of an antibody which has retained its capacity to bind the specific epitope, such as a Fab fragment.

In a preferred embodiment, the antibody of the present invention recognizes the protein kinase of the present invention.

The term "recognizes the protein kinase of the present invention" as used herein means that the antibody does not or insignificantly cross-reacts with other substances such as different protein kinases present in the same biological environment. Moreover, it means that the antibody does not or insignificantly cross-reacts with different protein kinases when tested in in vitro systems.

In another preferred embodiment, the antibody of the present invention is a monoclonal antibody.

Another object of the invention is to provide diagnostic compositions for the detection and/or monitoring of Alzheimer's disease comprising an epitope of the invention;

a kinase of the invention; and/or an antibody of the invention.

The diagnostic composition of the invention may comprise for example an antibody of the invention which specifically recognizes one of the kinases of the invention or an enhanced level of said kinases in a sample to be tested. In another embodiment, said diagnostic composition may comprise an antibody of the invention directed to one of the epitopes of the invention. Thus, an Alzheimer correlated disease state of a sample may be detected by treating said sample with an antibody recognizing the epitope of the invention. The antibody-epitope (hapten) complex may be visualized using a second antibody directed to the antibody of the invention and being labelled according to methods known in the art (see, e.g., Harlow and Lane, ibid.).

In still another embodiment of the present invention, said diagnostic composition may consist of an epitope of the invention and an antibody of the invention. Treatment of a sample with said antibody may give rise to conclusions with regard to the disease state of the corresponding patent, if the binding of said antibody to said sample is brought in relation to binding of said antibody to said epitope of the invention used as a reference sample.

In still another embodiment, the diagnostic composition may comprise an epitope of the invention, a kinase of the invention and an antibody of the invention. Kinase activity may be monitored with respect to phosphorylation of the sample as compared to the phosphorylation of the epitope of the invention. From the quantitated kinase activity the phosporylation state of the tau protein contained in said sample and therefore the disease state of the patient may be deduced. The kinase activity may e.g. be deduced by including a substrate analog in the same reaction, which is visually detectable upon enzymatic conversion. Such substrate analogs are widely used in the art. Alternatively, the amount of phosphorylated tau protein in the sample may be detected after treatment with the kinase of the invention by employing an antibody of the invention directed to the phosphorylated epitope and using the amount of antibody-epitope complex provided by the diagnostic composition as an internal standard, or by determining the amount of phosphate incorporated into tau protein by the kinase, e.g. by radioactive tracer methods which are well known in the art.

The person skilled in the art is in the position to design other test systems which combine any of the above objects of the invention. It is to be understood that all conceivable combinations fall within the scope of protection of the present invention.

Another object of the invention is to provide a method for the in vitro diagnosis and/or monitoring of Alzheimer's disease comprising assaying a cerebrospinal fluid isolate of a patient or carrying out a biopsy of nerve tissue for the presence of a phosphorylated Alzheimer tau protein containing an epitope of the invention;

for the presence of a protein kinase of the invention; or for the presence of phosphatases PP2a, PP1 and/or calcineurin.

The "cerebrospinal fluid isolate of a patient" is obtained by standard medical procedures.

An example for a nerve tissue suitable for said biopsy is the olfactory epithelium. The person skilled in the art may carry out said method employing e.g. the diagnostic tools illustrated in connection with the diagnostic compositions, supra.

In a preferred method of the present invention, the Alzheimer tau protein and the phosphorylation of serine residue 262 of tau protein, respectively, is detected by using an antibody of the invention.

Said antibody preferably is an antibody directed to an epitope of the invention.

In another preferred embodiment of the invention, the protein kinase is detected by using an oligo- or polypeptide comprising an epitope of the invention and/or by using an antibody of the invention.

Still another object of the invention is to provide a method for the in vitro conversion of normal tau protein into Alzheimer tau protein wherein normal tau protein is treated with a protein kinase of the present invention under conditions which allow the phosphorylation of said normal tau protein.

The term "Alzheimer tau protein" refers to tau protein that is abnormally phosphorylated (e.g. at ser-pro or thr-pro motifs) and recognized by Alzheimer-specific antibodies.

The term "conditions which allow the phosphorylation of said normal tau protein" refers to conditions allowing the activity, preferably the optimal activity, of protein kinase. This activity results in phosphorylation of the substrate at the ser-pro and/or thr-pro motifs. The phosphorylated substrate may then be recognized by Alzheimer-specific antibodies.

Normal tau protein may be derived from natural or recombinant sources. It is, for the purpose of carrying out the method of the present invention, however, expedient to use recombinant material.

The method of the present invention provides sufficient amounts of Alzheimer tau protein for a variety of purposes: With the method of the present invention an in vitro model for the study of the generation of the Alzheimer state of proteins may be established (see above). Moreover, inhibitors may be tested which prevent the conversion of normal to Alzheimer tau protein. These "inhibitors" may be specific for the epitope to be phosphorylated by e.g. blocking the epitope or may be directed to various domains on the protein kinase, as long as they prevent or disturb its biological activity. Another type of inhibition is the antagonistic action of phosphatases on tau or its kinases. Furthermore, the Alzheimer tau protein generated by the method of the present invention may be employed in binding studies to microtubule structures thus contributing to the elucidation of the molecular basis underlying Alzheimer's disease.

The person skilled in the art knows how to employ the method of the present invention for a variety of different purposes which all fall under the scope of protection of the present invention.

The present invention relates, moreover, to the use of an epitope of the invention for the generation of Alzheimer tau protein specific antibodies or antibodies to a tau protein specific for the onset of Alzheimer disease.

The methods for obtaining said antibodies are well known in the art; thus, the generation of polyclonal or monoclonal antibodies may be conducted using standard methods (see, e.g., Harlow and Lane, ibid.). If an oligo- or polypeptide is used for the generation of antibodies it is desirable to couple the peptide comprising the epitope to a suitable carrier molecule capable of inducing or enhancing the immune response to said epitope, such as bovine serum albumin or keyhole limpet hemocyanin. The methods of coupling hapten (comprising or being identical to the epitope) and carrier are also well known in the art (Harlow and Lane, ibid.). It is also to be understood any animal suitable to generate the desired antibodies may be used therefor.

In another aspect, the present invention relates to a pharmaceutical composition for use in the treatment or prevention of Alzheimer's disease comprising an inhibitor of the formation of Alzheimer paired helical filaments from tau protein dimers.

In accordance with the present invention, it was found that tau proteins form antiparallel dimers via assembly of their repeat units located in the C-terminal domain of the protein. Whereas dimerization of tau proteins appears to be a physiological process, the formation of higher order structures such as PHFs seems to be due to deregulation in the assembly process. Consequently, PHFs are formed from a number of tau dimers wherein the cross-linking of dimers may occur via intermolecular disulfide bridging.

Deregulation of the assembly process with subsequent formation of PHFs from tau dimers appears to be due to abnormal phosphorylation of tau proteins because, as has been found in accordance with the present invention, truncated tau proteins consisting merely of the repeat units are able to form PHFs, whereas tau proteins or tau-like proteins comprising the N-terminus and C-terminus as well are unable to do so.

An inhibitor useful in the composition of the present invention is therefore any inhibitor capable of inhibiting the formation of PHFs from tau dimers regardless of the molecular mechanism it interferes with. Such an inhibitor may be, for example, an inhibitor to a protein kinase responsible for abnormal phosphorylation of tau proteins as a compound interfering with the formation of intermolecular cross-links or association of tau dimers.

A further object of the present invention is to provide a method for testing drugs effective in dissolving Alzheimer paired helical filaments comprising the following steps:

(a) allowing the formation of Alzheimer paired helical filaments from polypeptides comprising tau-derived sequences under appropriate conditions;
(b) incubating the Alzheimer paired helical filaments with the drug to be tested; and
(c) examining the result of the incubation of step (b) with respect to the dissolution of the Alzheimer-like paired helical filaments.

The term "effective in dissolving Alzheimer paired helical filaments" as used herein is intended to also include partially dissolved PHFs. For the object of the present invention it is sufficient that the drug to be tested is effective in the reduction of the size or the break-up of PHFs, thus fulfilling a supplementary function in therapy, although a total dissolution by the drug is preferred.

The term "polypeptides comprising tau derived sequences" refers to any polypeptide which comprises sequences from tau protein capable of forming PHFs regardless of the length of said sequences or of mutations, deletions, insertions or heterologous sequences as long as the function of said polypeptides to form PHFs remains intact.

The term "appropriate conditions" in connection with the formation of Alzheimer PHFs refers to any condition which allows said formation. Said conditions may include the availability of a MAP kinase if natural tau protein is used.

In a preferred embodiment, the conditions applied in step (a) of said method comprise an environment of 0.3 to 0.5 M Tris-HCl and pH 5.0 to 5.5 without additional salts.

Still another object of the invention is to provide a method for testing drugs effective in the prevention or reduction of the formation of Alzheimer paired helical filaments comprising the following steps:

(a) incubating the drug to be tested with polypeptides comprising tau-derived sequences under conditions which allow the formation of Alzheimer paired helical filaments in the absence of said drug; and
(b) examining the result of the incubation of step (a) with respect to the presence or absence of Alzheimer paired helical filaments in the incubation mixture.

The term "conditions which allow the formation of Alzheimer paired helical filaments in the absence of said drug" refers to any condition which allows the formation of PHFs provided said drug is not included in the incubation mixture. A preferred example of such a condition is an environment of 0.3 to 0.5 M Tris-HCl and pH 5.0 to 5.5 without additional salts.

The term "presence or absence of Alzheimer paired helical filaments" as used herein is intended to include results wherein only a limited amount of PHFs has been formed as compared to control experiments where no such drug has been used.

In a preferred embodiment in the above methods, said polypeptides comprise essentially the repeats from the C-terminal part of the tau protein only.

In accordance with the present invention, it was found that the repeats comprised in the C-terminal domain of the tau protein are responsible for dimerization of the protein under physiological conditions and subsequent oligomerization leading to Alzheimer-like paired helical filaments. The term "Alzheimer-like paired helical filaments" is used here as opposed to "Alzheimer paired helical filament" solely to indicate that non-repeat unit parts of the tau protein normally present in PHFs are absent from PHFs generated by said polypeptides.

Accordingly, the polypeptides comprising essentially the repeat units only provide an ideal in vitro system to study PHF formation and studies on the fine structure of PHFs.

In a particularly preferred embodiment, said polypeptides are comprising mainly the repeat regions of tau, such as K11 and/or K12.

K11 and K12 are ideally suited for the above testing purposes because they are essentially comprised of repeat units from the tau protein only.

For the method of the invention, K11 and K12 may be used alone or in combination.

In a further aspect, the present invention relates to a method for testing drugs effective in dissolving Alzheimer paired helical filaments comprising the following steps:
(a) introducing a functional gene encoding a MAP kinase under the control of suitable regulatory regions into a cell expressing or overexpressing tau protein;
(b) allowing the formation of phosphorylated tau protein and of Alzheimer paired helical filaments;
(c) isolating said Alzheimer paired helical filaments;
(d) applying the drug to be tested to said paired helical filaments under appropriate conditions; and
(e) examining the effect of said drug on said paired helical filaments.

The term "cell expressing tau protein" as used in step (a), supra, refers to cells which endogenously express tau or which have the capacity to express tau and into which a functional tau gene has been introduced. In the latter case the person skilled in the art is aware of the fact that the sequence of the introduction of the genes encoding the MAP-kinase and tau is irrelevant for the purpose of the method of the invention.

The term "under appropriate conditions" in step (c), supra, refers to conditions which allow the drug to be effective in dissolving PHFs and are particularly optimal conditions.

Said method is particularly advantageous, since the system involved which is based on the use of continuously growing cell lines providing a close image of the in vitro situation provide an ample supply of phosphorylated tau protein.

In a preferred embodiment said cell expressing tau protein is a neuroblastoma or chromocytoma cell or a primary culture of nerve cells.

Such cells or cell lines are well known in the art. Preferred examples are the neuroblastoma cell lines N21 and PC12.

These cell lines are particularly preferred because they express tau endogenously.

A further object of the invention is a pharmaceutical composition for the treatment of Alzheimer disease comprising a PP2a and/or PP-1 and/or calcineurin phosphatase as the active or one of the active ingredients.

THE FIGURES SHOW

FIG. 1A: Amino acid sequence of tau (SEQ ID NO: 1)(isoform htau40, Goedert et al., 1989). The motifs SP, TP, IGS and CGS are highlighted.

FIG. 1B: (A) SDS gel of tau isoforms, (B) immunoblots of (A) and PHF tau with the AT8 antibody. (A) SDS gel. Lane 1, marker proteins. Lane 2: Tau from bovine brain, showing several isoforms in a mixed state of phosphorylation. Lane 3, bovine brain tau after dephosphorylation with alkaline phosphatase. Note that all isoforms shift to a lower $M_r$. Lanes 4 and 5: Tau from normal human brain, before and after dephosphorylation. Lanes 6–11: bacterially expressed human tau isoforms htau23, 24, 37, 34, 39, 40 (see Goedert et al., 1989, ibid.). These isoforms have either three or four internal repeats of 31 residues each in the C-terminal half (three: htau23, 37, 39; four: htau24, 34, 40). Near the N-terminus there can be zero, one, or two inserts of 29 residues (zero: htau23, 24; one: htau37, 34; two: htau39, 40).

(B) Immunoblots with the AT8 antibody. Lane 1, PHF tau, showing 4–6 isoforms in the range of 60–70 kD; all of them react strongly with ATS. Lanes 2–11, same preparations as in (A); none of the bovine or normal human tau isoforms show any reaction.

FIG. 2: Phosphorylation of bacterially expressed human tau isoforms with the kinase from brain. (A) SDS gels, (B) immunoblots with AT8.

(A) Lanes 1 and 2, SDS gel of htau23 before and after extract phosphorylation (note the upward shift in $M_r$.) Lanes 3–10 show analogous pairs for other isoforms (htau24, 34, 39, 40).

(B) Immunoblots of (A) with AT8 antibody. It reacts with all tau isoforms after phosphorylation (even lanes; including htau37, not shown here).

Figure 3:
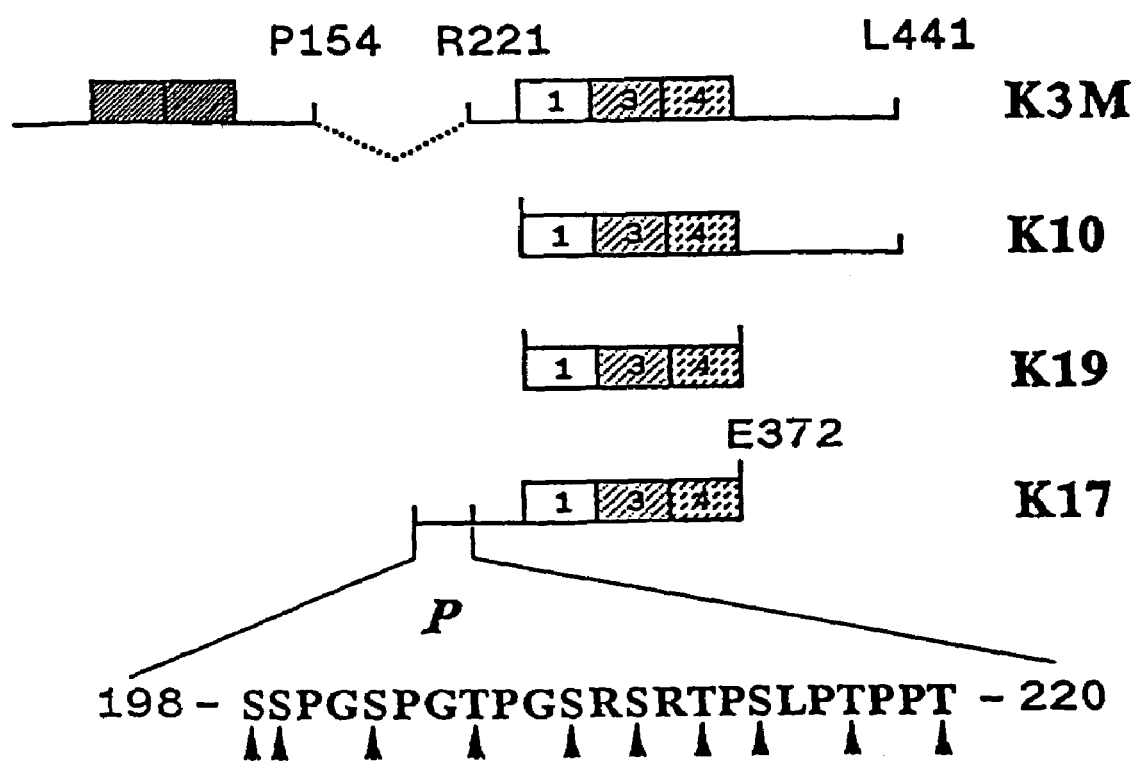

FIG. 3: Diagram of constructs K3M, K10, K19, and K17. K19 (99 residues) contains the sequence Q244-E372 (SEQ ID NO: 28) of htau23 plus an N-terminal methionine. This comprises three of the repeats (repeat 1, 3, and 4; repeat 2 is absent in htau23). K10 (168 residues) is similar, except that it extends to the c-terminus of htau23 (L441). K17 (145 residues) contains the sequence S198-E372 (assembly domain starting at the chymotryptic cleavage site, up to end of fourth repeat, but without the second repeat, plus an N-terminal methionine). K3M (335 residues) contains the N-terminal 154 residues of bovine tau4, plus the sequence R221-L441 of htau23 (without second repeat). The location of peptide S198-T220 is indicated in K17. By comparison of the constructs the epitope of AT8 must be in this region (see FIG. 4).

FIG. 4: Phosphorylation of htau40 and constructs K10, K17, K3M, and K19.

(A) SDS gel. Odd lanes, even lanes, after phosphorylation. Note the upward shift of the bands after phosphorylation. In lane 4 there are two bands because K10 is not completely phosphorylated.

(B) Immunoblot of (A) with AT8. The antibody reacts only with htau40 (lane 2) and K17 (lane 6), both in the phosphorylated state, but not with K10 (lane 4) or K3M (lane 8), although these constructs are also phosphorylated and show an $M_r$ shift.

(C) Construct K19 before and after incubation with the kinase. Lanes 1 and 2, SDS gel; there is no $M_r$ shift and no phosphorylation, confirmed by autoradiography (not shown). Lanes 3 and 4, inmunoblot with AT8, showing no reaction. This confirms that the epitope is not in the repeat region.

Figure 5:
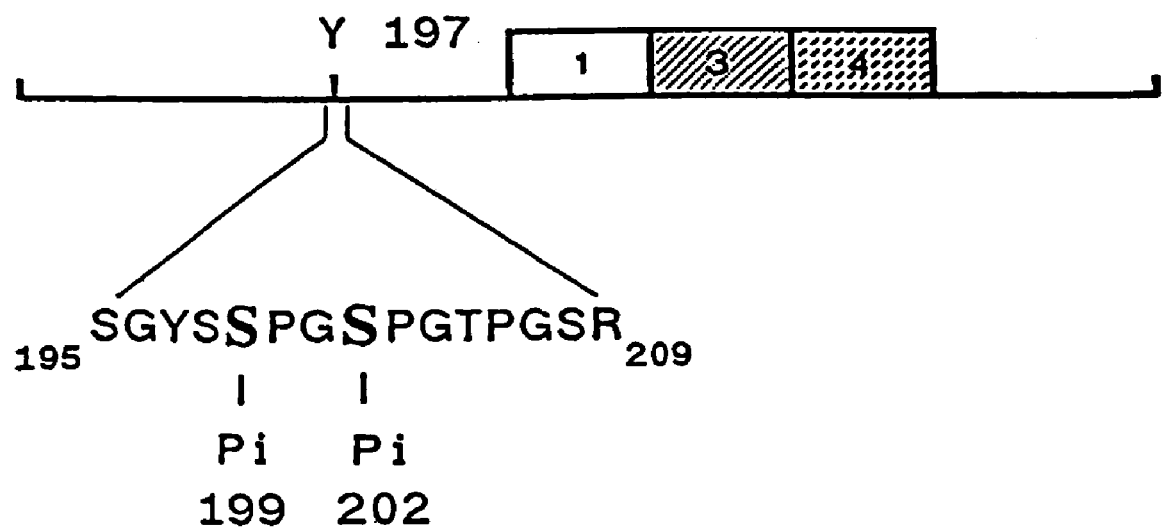

FIG. 5: Diagram of tryptic peptide S195-R209. The 15 residue peptide (SEQ ID NO: 29) (containing 5 serines and 1 threonine) was labeled with two radioactive phosphates at S199 and S202, as determined by sequencing.

Figure 6:
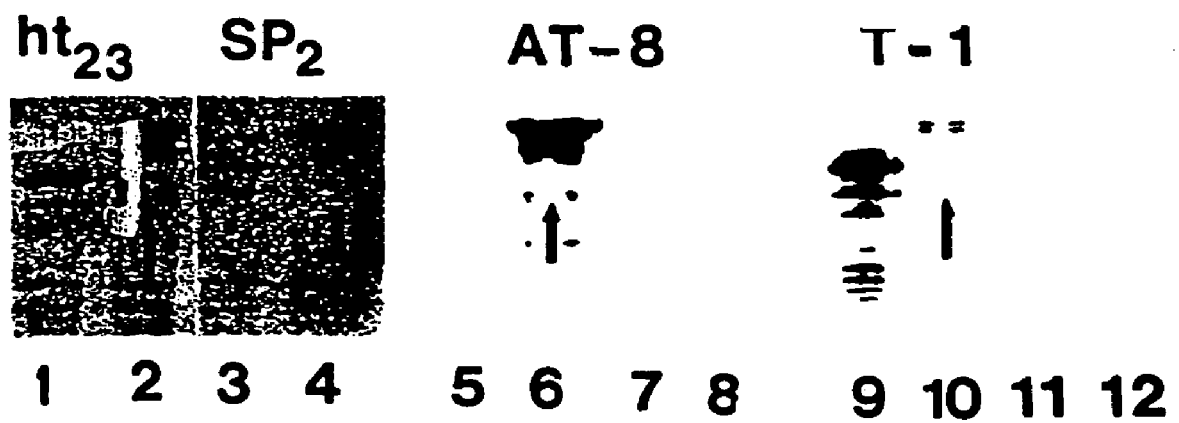

FIG. 6: Phosphorylation and antibody reactions of the D-mutant of htau23 (S199 and S202 changed into D). Lanes 1 and 2, SDS gel of htau23 before and after extract phosphorylation; lanes 3 and 4, D-mutant before and after extract phosphorylation. Note that the D-mutant runs slightly higher than htau23 (lanes 1,3), but after phosphorylation both proteins have the same position in the gel (lanes 2, 4).

Lanes 5–8, immunoblots of lanes 1–4 with AT8. The antibody reacts only with extract phosphorylated htau23 (lane 6), but neither with the unphosphorylated form (lane 5) nor with the D-mutant (lanes 7, 8), although it was phosphorylated as seen by the additional shift and autoradiography (not shown).

Lanes 9–12, immunoblots of lanes 1–4 with TAU1. This antibody reacts only with htau23 before phosphorylation (lane 9), but not with the phosphorylated form (lane 10) nor with the D-mutant (lanes 11, 12). The aspartic acid apparently mimicks a phosphorylated serine and thus masks the epitope. The minor reaction of htau23 with TAU1 in lane 10 shows that the protein is not completely phosphorylated.

FIG. 7: Time course of phosphorylation of bacterially expressed human isoform htau23 with the brain kinase activity and corresponding autoradiogram.

(A) SDS-PAGE of htau23 after incubation with the kinase between 0 and 24 hours, as indicated. The unphosphorylated protein is a single band of $M_r o=48$ kD (lane 1). Lanes 3–14 show that phosphorylation leads to a progressive shift to higher $M_r$ with well defined intermediate stages. The even lanes (numbered 4, 6, etc. below FIG. 1B) are observed in the presence of 10 μm okadaic acid (OA) (labeled "+" below FIG. 1A). The odd lanes (3, 5, etc. labeled "–") are without okadaic acid. The first stage takes about 2 hours (shift to a new $M_r1=52$ kD), the second is finished around 10 hours ($M_r2=54$ kD), the third is finished around time 24 hours ($M_r3=56$ kD); no further shift is observed during the subsequent 24 hours. Lane 2 shows a mutant that is not of significance in this context.

(B) Autoradiogram of (A). The quantitation of the phosphate incorporated (mol $P_i$/mol protein) in this experiment was as follows (–OA/=OA): 30 mm (0.5/1.0), 60 mm (0.7/1.4), 120 mm (1.0/2.0), 10 hours (2.0/3.0), 24 hours (3.2/4.0).

FIG. 8: (A) SDS gel showing the time course of phosphorylation of htau23 similar to that of FIG. 1A, but with 10 μM okadaic acid throughout; (B) immunoblot of (A) with the monoclonal antibody SMI34. The antibody recognizes the protein only in the second and third stage of phosphorylation, but not in the first.

Figure 9A:
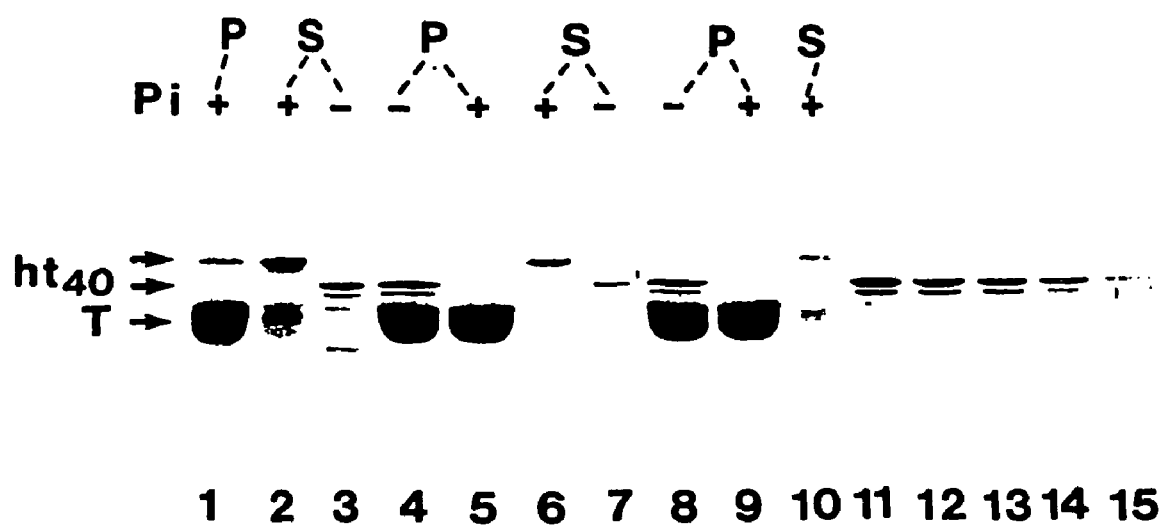
Figure 9B:
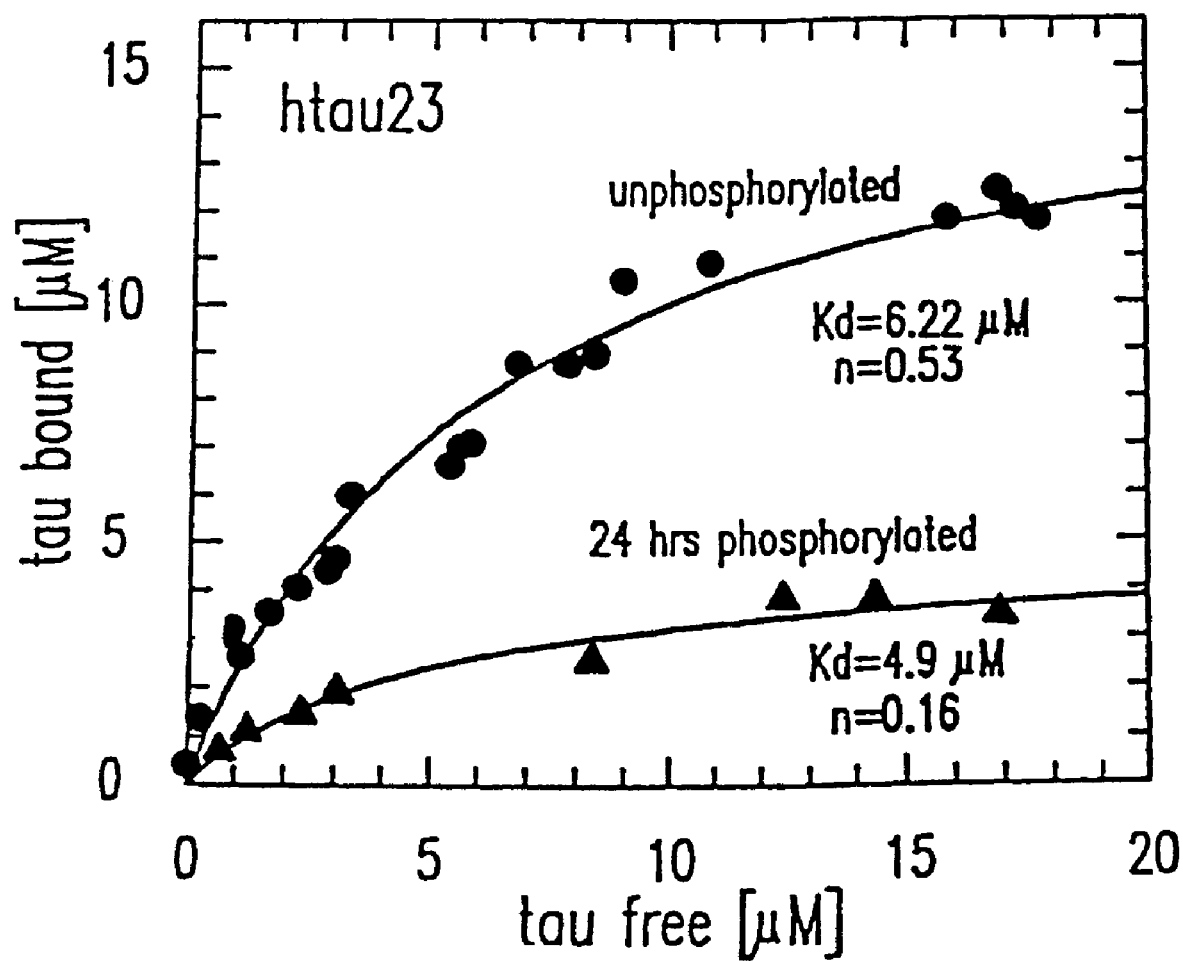

FIG. 9: Binding of tau isoforms to microtubules before and after phosphorylation.

(A) SDS gel of a binding experiment, illustrated for the case of the tau isoform htau40 (whose band is clearly separated from that of tubulin (T) so that both components can be shown simultaneously, without having to remove tubulin by a boiling step). The top line indicates pellets (P) or supernatants (S), with or without phosphorylation for 24 hours (+ or $-P_i$). Lanes 1–4, 20 μM tau protein (total concentration), phosphorylated (lanes 1, 2) or not (lanes 3, 4). The comparison of lanes 1 and 2 shows that most of the phosphorylated protein is free (S), while only a small fraction is bound to the microtubules (P). Lanes 3 and 4 show that in the unphosphorylated state about half of the protein is bound, the other half free (note also that the phosphorylated protein bands, lanes 1, 2, are higher in the gel than the unphosphorylated ones, lanes 3, 4, similar to FIG. 1). Lanes 5–8, similar experiment with 15 μM htau40. Lanes 9, 10 show the case of 10 μM phosphorylated protein. Lanes 11–15 are for density calibration with known amounts of htau40 (15, 10, 7.5, 5, and 2.5 μM, resp.).

(B) Binding curves of htau23 and (C) htau34 to microtubules before (circles) and after 24 hour phosphorylation (triangles); these curves were derived from SDS gels similar to that of FIG. 3A. Polymerized tubulin is 30 μM. Fitted dissociation constants $K_d$ and stoichiometries are as indicated. In each case the most dramatic effect is on the number of binding sites which decrease about three-fold upon phosphorylation, from around 0.5 (i.e. one tau for every two tubulin dimers) down to about 0.16 (one tau for six tubulin dimers). Note that the binding of unphosphorylated 4-repeat isoforms (such as htau34) is particulary tight ($K_d$ round 1–2 μM).

Figure 10:
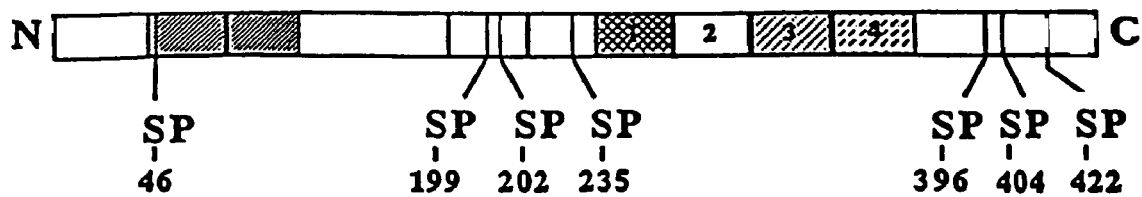

FIG. 10: Diagram of htau40, showing the location of the 7 ser-pro motifs phosphorylated by the kinase activity. The boxes labeled 1–4 are the internal repeats involved in microtubule binding; the second is absent in some isoforms (e.g. htau23). The two shaded boxes near the N-terminus are inserts absent in htau23 and htau24 so that these molecules have only 6 ser-pro motifs. The following radioactive tryptic peptides were found:

24–49: KDQGGYTMHQQQEGOTDAGLKES$_P$PLQ (SEQ D NO: 31)
191–209: SGDRGYSS$_P$PGS$_P$PGTPGSR (SEQ ID NO: 32)
231–240: TPPKS$_P$PSSAK (SEQ ID NO: 33)
396–405: SPVVSGDTS$_P$PR (SEQ ID NO: 34)
385–405: TDHGAEIVYKS$_P$PVVSGDTS$_P$PR (SEQ ID NO: 35)
407–428: HLSNVSSTGSIDMVDS$_P$PQLATL (SEQ ID NO: 36)
260–266: IGS$_P$TENL (SEQ ID NO: 37)

Figure 11:
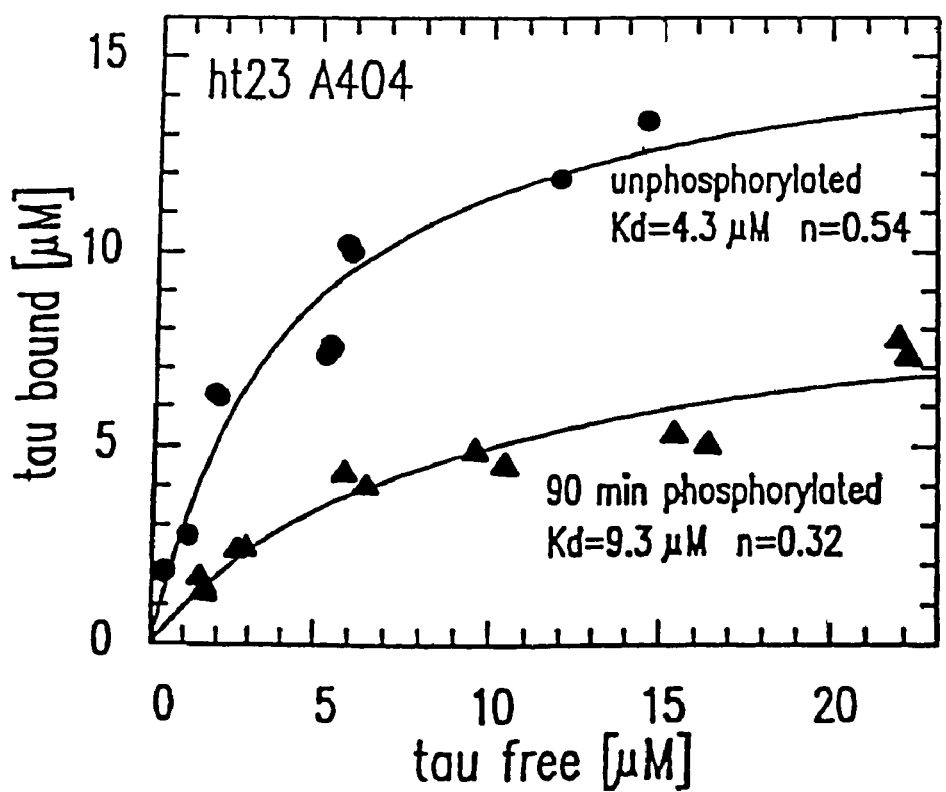
Figure 12A:
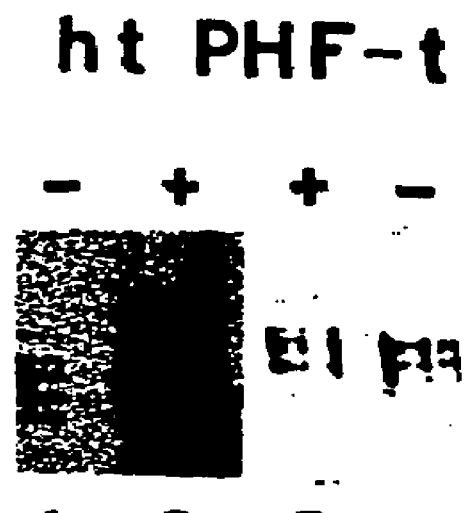
Figure 12C:
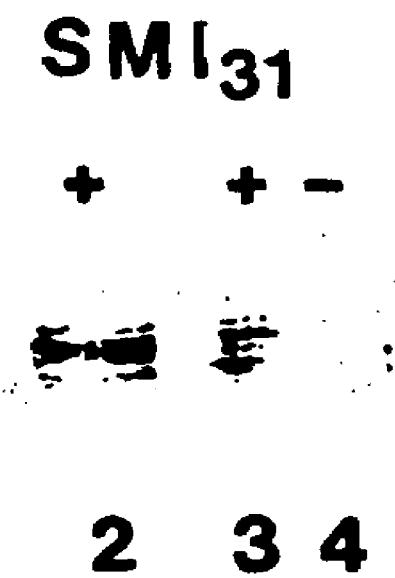
Figure 12B:
Figure 12D:

FIG. 11: Binding of htau34 to microtubules, before (circles) and after phosphorylation for 90 mm (stage 1, triangles). The reduction in binding capacity is very similar to that after 24 hours phosphorylation (compare FIG. 9B).

FIG. 12: SDS-PAGE and immunoblots of tau protein from Alzheimer and normal human brain with antibodies SMI33, SMI31, and SMI34.

(A) Lane 1, SDS-PAGE of tan protein from a normal human control brain, showing 5–6 bands between $M_r55$ and 65 kD (somewhat lower than the PHF tan of lane 3). Lane 2, normal human tau after phosphorylation with kinase activity, resulting in an upward shift of all bands. Lanes 3, 4, immunoblot of PHF tau with antibody 5E2 which recognizes all tau isoforms independently of phosphorylation (Kosik et al., Neuron 1(1988), 817–825). Lane 3, PHF tau as isolated from an Alzheimer brain; lane 4, after dephosphorylation with alkaline phosphatase. Note that the bands of the dephosphorylated protein are shifted down on the gel.

(B) Immunoblot of (A) with SMI33. The antibody recognizes normal human tau (lane 1), and PHF tau after dephosphorylation (lane 4).

(C) Immunoblot of (A) with SMI31. Note that the antibody recognizes normal human tau after phosphorylation, and PHF tau in its natural state of phosphorylation (lanes 2, 3).

(D) Immunoblot of (A) with SMI34. This antibody recognizes normal human tau only after phosphorylation (lane 2), and PHE tau (lane 3).

FIG. 13: Time course of phosphorylation of bacterially expressed human isoform htau23 (similar to previous figure) and immunoblots with antibodies SMI33, SMI31, SMI34, TAU1, and AT8.

(A) SDS-PAGE, phosphorylation times 0–24 hours, showing the successive $M_r$ shifts. (B–F) Immunoblots with SMI31, SMI34, SMI33, TAU1, and AT8. Antibodies SMI33 and TAU1 recognize htau23 fully up to the end of stage 1 (2 hours), but the epitope becomes blocked during the second stage. Antibodies SMI31, SMI34, and AT8 are complementary in that they recognize the protein only in the second and third stage of phosphorylation.

(G–H) Immunoblot of htau34 with SMI33 and SMI31 which recognize the protein from the stage 2 phosphorylation onwards, similar to SMI31.

FIG. 14: SDS-PAGE of tau and several constructs, and immunoblots with the antibodies SMI33, SMI31, and SMI34.

(A) SDS-PAGE. Lanes 1 and 2: Construct K10 before and after phosphorylation with the kinase for 24 hours. Lanes 3 and 4: Construct K17 before and after phosphorylation. Lanes 5 and 6: Construct K19 before and after phosphorylation. All constructs except K19 show a shift upon phosphorylation. With K10 one observes three shifted bands, with K17 there is only one shifted band.

(B) Immunoblot of (A) with SMI33: The antibody recognizes only K17 in the unphosphorylated form (lane 3), suggesting that the epitope lies before the repeats.

(C) Immunoblot of (A) with SMI34. The antibody recognizes K10 and K17 in the phosphorylated form (only top bands, lanes 2, 4). The antibody does not recognize K19 (the repeat region), but requires sequences on both the N-terminal and C-terminal side of the repeats. The epitope is therefore non-contiguous (conformation-dependent).

(D) Immunoblot of (A) with SMI31. The antibody recognizes only the top band of the phosphorylated K10 (lane 2), suggesting that the epitope lies behind the repeat region.

FIG. 15: (A–G) Diagram of point mutants of htau40 and htau23.

FIG. 16: SDS gel of htau40 and the point mutants of FIG. 15, and immunoblots with antibodies SMI33, SMI31, and SMI34.

(A) Lanes 1–8, SDS gel of htau40 and its mutants KAP235, KAP396, and KAP235/396 in the unphosphorylated and phosphorylated form (+). In each case phosphorylation leads to an upward shift in the SDS gel.

Blot of (A) with SMI33. The antibody response is strongly reduced when S235 is mutated, both in the dephosphorylated and phosphorylated state (lanes 3+4, 7+8). This indicates that the (dephosphorylated) first KSP motif is part of the epitope of SMI33. When S396 is mutated to A the behavior is similar to the parent molecule, i.e. strong antibody response in the dephosphorylated state, no reaction in the phosphorylated state, so that S396 does not contribute to the epitope of SMI33.

(C Blot of (A) with SMI31. The antibody recognizes htau40 and all mutants in the phosphorylated form (lanes 2, 4, 6, 8). This shows that phosphorylation of the two KSP motifs is not the main determinant of the epitope.

(D Blot of (A) with SMI34. The reaction is similar to SMI31 but more pronounced, again indicating that the two KSP motifs are not essential.

FIG. 17:: Deletion mutants of tau and their antibody response. (A) SDS gel of constructs containing only two repeats (K5-K7) or one repeat (K13-K1 5), before and after phosphorylation. (B) Immunoblot of (A) with SMI34. Note that the antibody recognizes all phosphorylated proteins (K7 only weakly). (C) Immunoblot of (A) with SMI31. Note that the antibody recognizes the phosphorylated two-repeat molecules (K5-K5), but not the one-repeat molecules (K13-K15). Lanes 7 and 8 show htau40 as a control. (D) SDS gel of constructs K2, K3M, and K4, before and after phosphorylation. (E) Blot of (D) with SMI34, recognizing only K4 phosphorylated. (F) Blot of (D) with SMI31, recognizing only K2 phosphorylated.

FIG. 18: (A–M) Diagram of htau40 and various mutants used in this study.

Figures 19A, 19B, 19C, 19D, 19E, 19F, 19G:
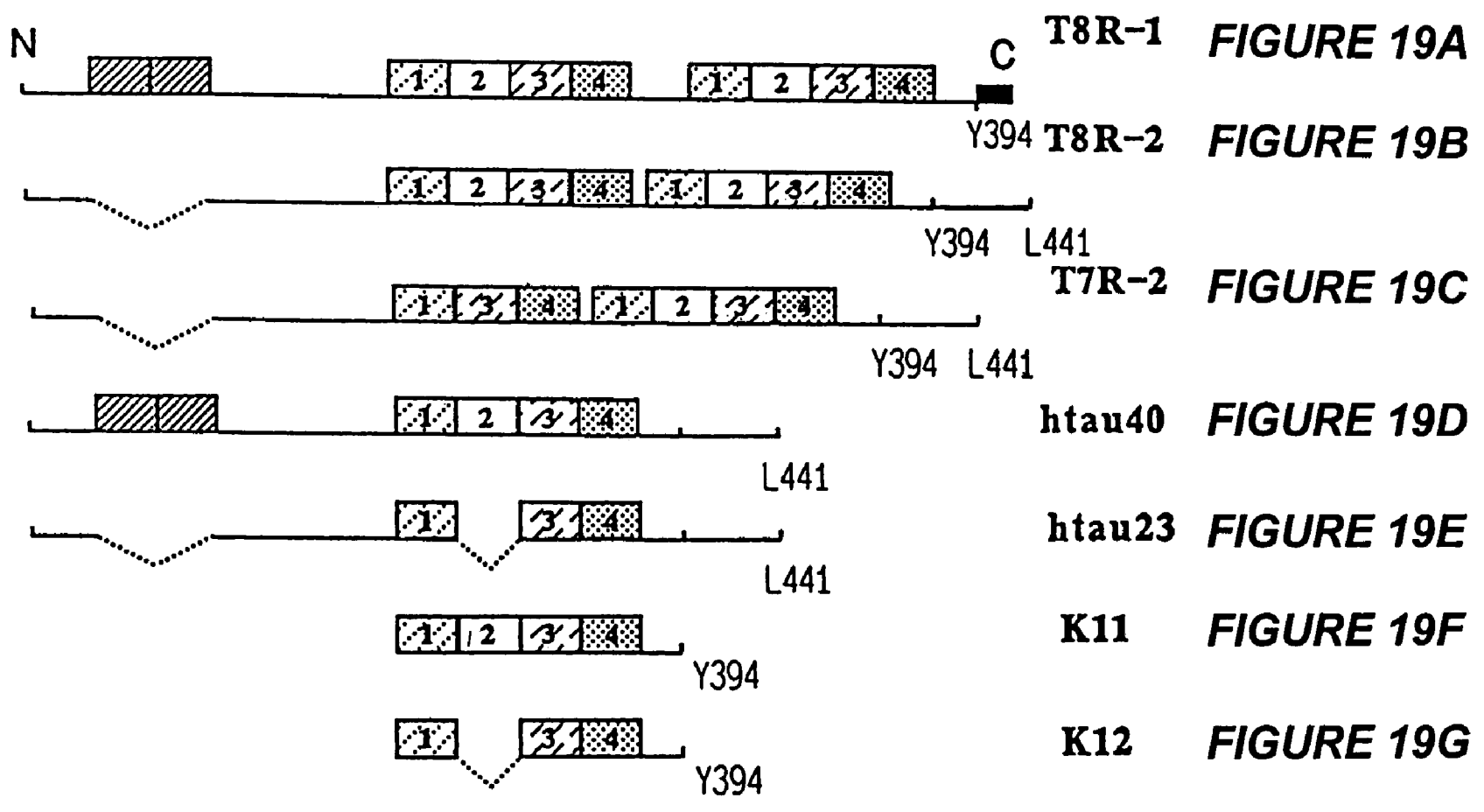

FIG. 19: Diagram of tan isoforms and constructs used in studies on tau dimerization and oligomerization (D) T8R-1,553 residues, MW 57743, derived from htau40 (see below). It has two inserts near the N-terminus (29 residues each, hatched), a repeat domain of four repeats (numbered 1–4) which is duplicated with a small spacer in between.

(B) T8R-2,511 residues, MW 53459; it lacks the N-terminal inserts, but has the four repeats duplicated.

(C) T7R-2,480 residues, MW 50212; similar to T8R-2, but without the second repeat sequence in the first repeat domain.

(D) Htau40,441 residues, MW 45850, the largest of the six human tau isoforms (Goedert et al.), with two N-terminal inserts and a repeat domain containing four repeats.

(E) Htau23,352 residues, MW 36760, the smallest of the human tau isoforms, without the N-terminal repeats and only three repeats.

(F) K11,152 residues, MW 16326, a repeat domain with four repeats plus a short tail.

(G) K12,121 residues, MW 13079, a repeat domain with three repeats plus a short tail.

FIG. 20: SDS PAGE (4–20%) and gel chromatography of tau constructs and cross-linked products. Gels a and c were run in reducing conditions (3 mM DTT in sample buffer), gel b in non-reducing conditions (except lane 1 with 3 mM DTT in sample buffer).

(D) Constructs T8R-1, Htau23 and K12. Molecular weight markers are given on the left.

(B) Construct K12 and cross-linked products. Cross-linking occurs spontaneously in the absence of DTT; it can be prevented by DTT, or induced by addition of PDM or MBS. Aggregation products are labeled on the right (monomers, dimers, trimers, tetramers etc.).

(C) Silver stained SDS gel of a Superose 12 gel filtration run of K12 cross-linked by PDM. The dimers (top band) elute before the monomers. Fractions 16 and 17 were used for electron microscopy.

(D) Elution profile of Superose 12 gel filtration of construct K12 monomers and dimers cross-linked with PDM.

The elution positions of calibration proteins are plotted against their effective hydrated Stokes radii on a logarithmic scale (right axis).

(E) CD spectrum of construct K12 (8 mg/ml in 40 mM HEPES pH 7.2, path length 0.01 mm). There is no significant α-helical or β-sheet structure. Similar spectra are obtained with other constructs as well as with full length tau.

Figure 21A:
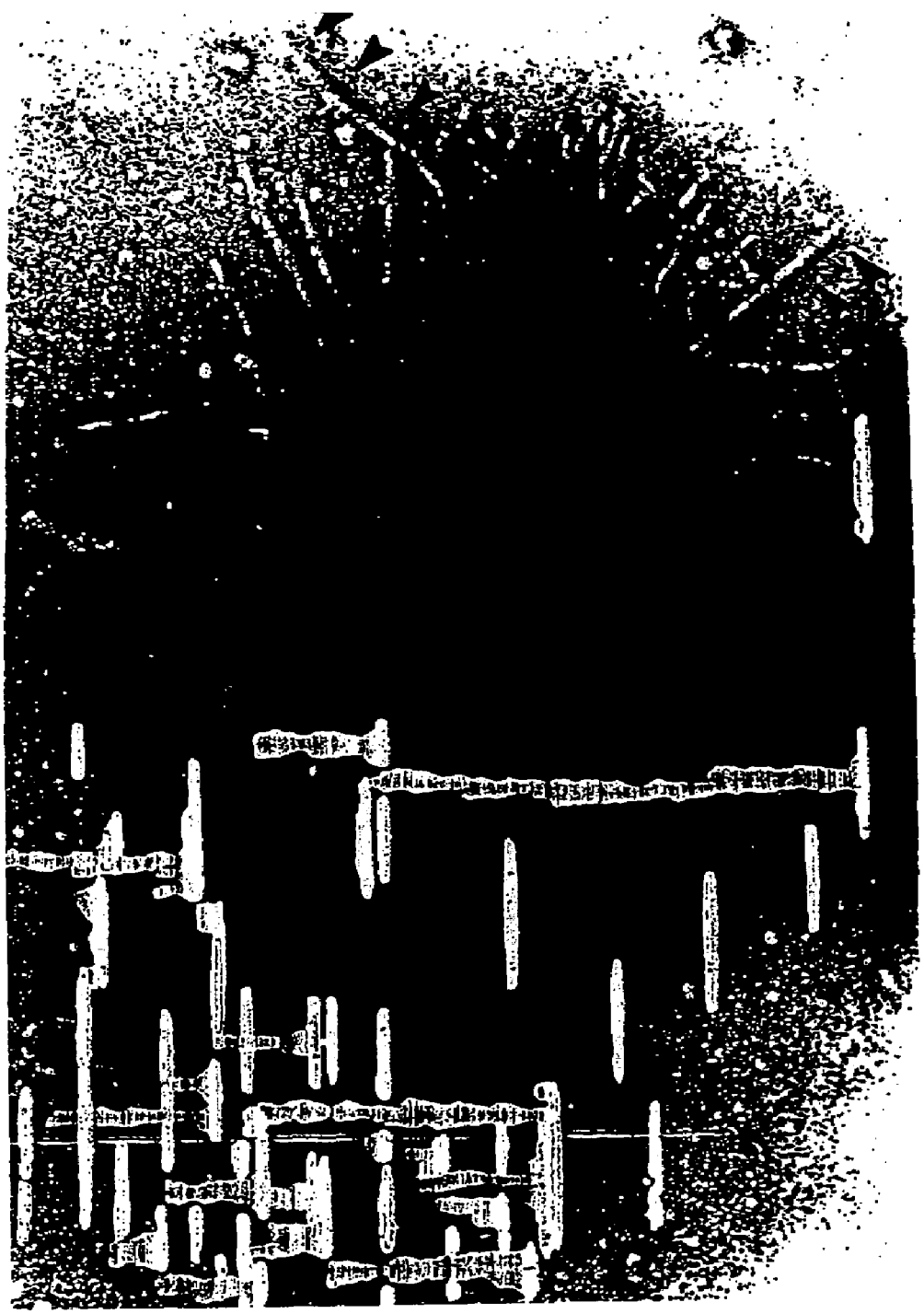
Figures 21B, 21C, 21D, 21E:
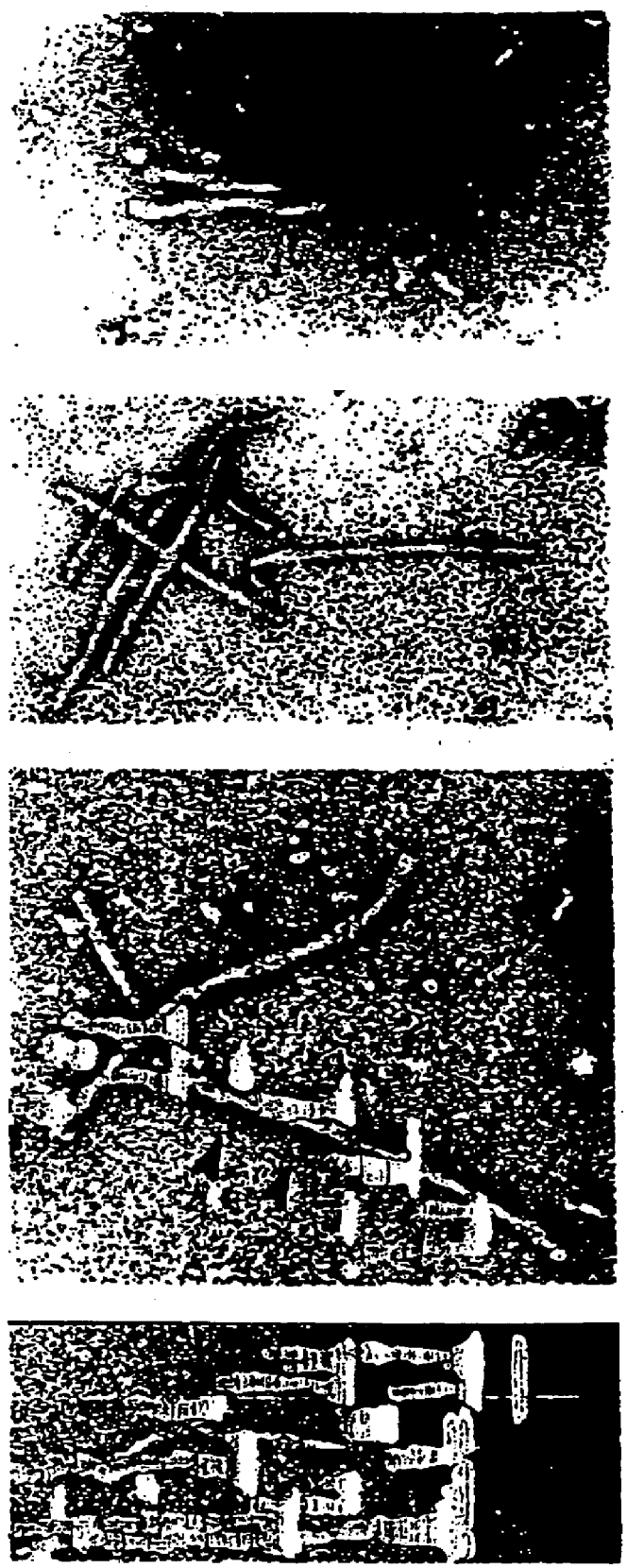

FIG. 21: Synthetic paired helical filaments from construct K12.

(A) A tangle of synthetic PHFs from K12 (crossover period of .approx. 70–75 nm indicated by arrowheads). The construct was expressed and purified by the methods described previously (Steiner et al.). It was dialysed against 0.5 M Tris-HCl, with pH values between 5.0 and 5.5. The solution was negatively stained with 2% uranyl acetate.

(B) and (C) Single fibers of synthetic paired helical filaments made from construct K12. Note the crossover repeats (arrowheads) and the rod-like particles of lengths around 100 nm (c, middle). Bar=100 nm.

FIG. 22(A–C): Synthetic paired helical filaments from K12 dimers cross-linked with PDM and negatively stained with 1% phosphotungstic acid (micrographs provided by M. Kniel). Bar=100 nm.

FIG. 23: Paired helical filaments from Alzheimer brain (micrographs provided by Dr. LichtenbergKraag).

(A) PHFs from neurofibrillary tangles prepared after Wischik et al., stained with 1% phosphotungstic acid. This preparation contains homogeneous long filaments which still retain their pronase sensitive "fuzzy coat." The crossover repeat is 75–80 nm, the width varies between a minimum of about 10 nm and a maximum of 22 nm.

(B) PHFs prepared after Greenberg & Davies. This preparation results in soluble filaments of shorter length than in (A) and is more heterogeneous. (1) is a paired helical filament with a 72 nm repeat and a width varying between 8 and 18 nm; (2) is a straight filament of 8 nm width; (3) is a twisted filament with a particularly wide diameter (up to 25 nm); (4) is a straight filament with a wide diameter (18 nm); (5) is a twisted rod-like particle about 80 nm long, equivalent to about one crossover period. In many cases the particles appear to have broken apart across the filament, e.g. the two rods labeled (4), the twisted filament of (3) and the short stub to the right of it, or the two straight rods above particle (3). Bar=100 nm.

FIG. 24: Electron micrographs of tau isoform htau23 and construct T8R-1 prepared by glycerol spraying and metal shadowing (A) monomers of htau23, (B) dimers of htau23, (C) monomers of T8R-1, (D) folded forms of T8R-1 (hair-pin folds showing intramolecular antiparallel association), (E) dimers of T8R-1. For lengths see Table 1 and FIG. 7. Interpretative diagrams are shown on the right. Bar=50 nm.

FIG. 25 (A–H): Length histograms of tau constructs and dimers.

FIG. 26: Electron micrographs of constructs K11 and K12.

(A) Monomers of K11, (B) dimers of K11, (C) tetramers of K11 formed by longitudinal association of two dimers.

(C) Monomers of K12, (D) dimers of K12, (E) tetramers of K12. Bar=50 nm.

FIG. 27: (A) K12 dimers cross-linked by PDM (i.e. Cys322 to Cys322);

(B) K12 dimers cross-linked by MBS (i.e. Cys322 to nearby Lys). Bar=50 nm.

FIG. 28: Antibody labeling of htau23, K12 and cross-linked products thereof.

(A) htau23 dimers with an antibody at one end (left) and with an antibody at each end (right) demonstrating the antiparallel dimerization of htau23;

(B) K12 diners with an antibody at one end (left), with antibodies at both ends (middle) and presumable tetramers with antibodies at the free ends (right) indicating that this type of association blocks the epitope;

(C) K12 dimers cross-linked with PDM, with an antibody at one end (left), with antibodies at each end (middle) and a tetramer with antibodies at the free ends (right);

(D) K12 dimers cross-linked by MBS with an antibody at one end (left), with antibodies at each end (middle) and a tetramer with antibodies at the free ends (right). Bar=50 nm.

Figures 29A, 29B, 29C, 29D, 29E, 29F, 29G:
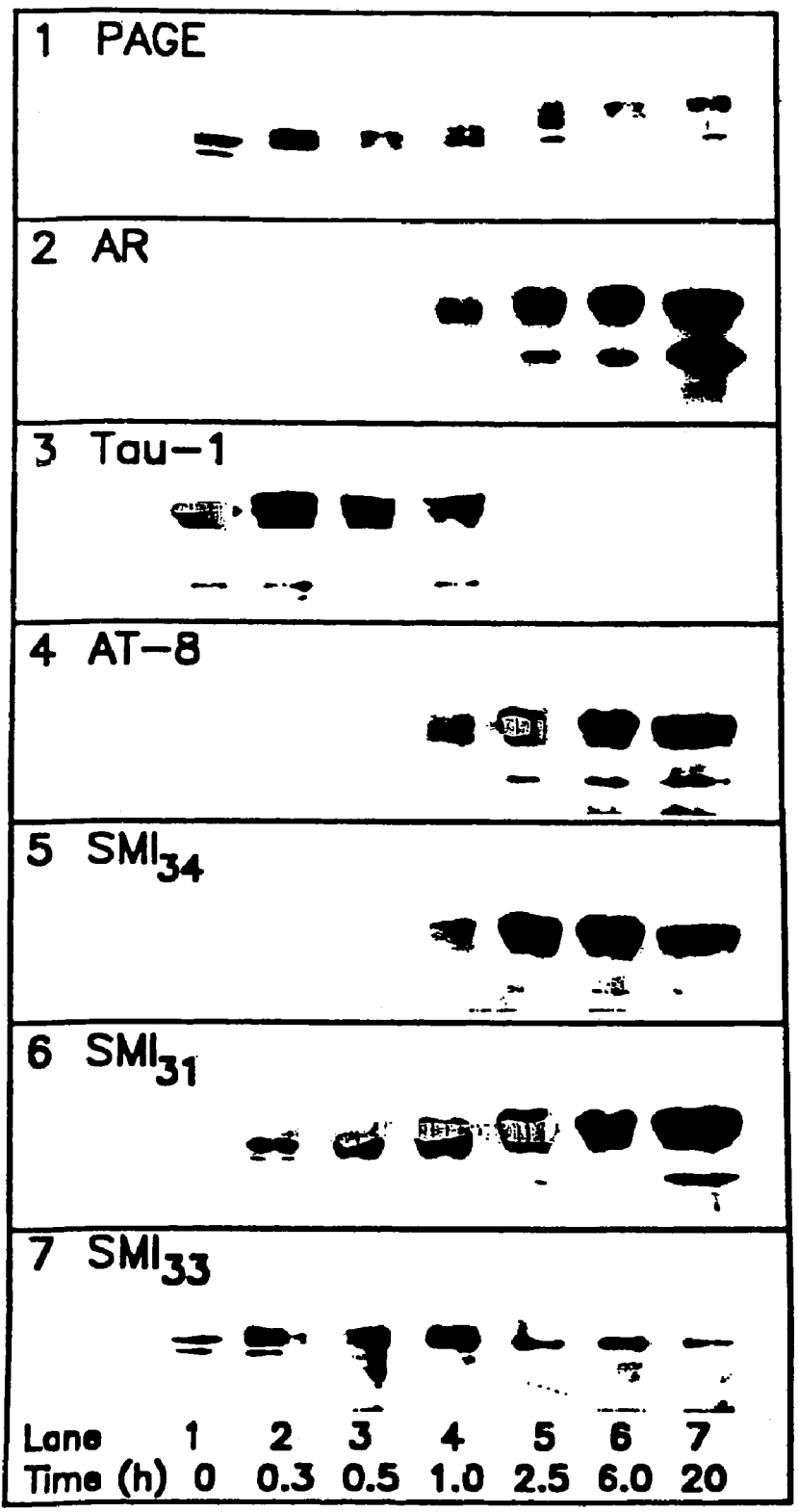

FIG. 29 (A–G): Time course of phosphorylation of htau40 by GSK3 and immune response. (A) SDS-PAGE of htau40 after incubation with the kinase between 0 and 20 hours at 37.degree. C. The minor lower band in lane 1 is a fragment. Note the progressive shift to higher $M_r$ values, similar to the effects of brain extract and MAP kinase. (B) Autoradiography. (C) Immunoblot with the antibody TAU1 whose reactivity is lost after .apprxeq. 2 h (following the phosphorylation of S199 and S202). (D) Immunoblot with antibody AT-8. (E) Immunoblot with antibody SMI34 (conformation sensitive and against phosphorylated Ser). (F) Blot with SMI31 (epitope includes phosphorylated S396 and S404). (G) Blot with antibody SMI33 which requires a dephosphorylated S235. There are some differences with respect to phosphorylation by MAP kinase or the brain extract. The SMI33 staining persists for a long period, suggesting that Ser235 is only slowly phosphorylated by GSK3. The staining of SMI31 appears very quickly, before that of ATS or SMI34, showing that S396 and S404 are among the earliest targets of GSK3.

Figure 30A:
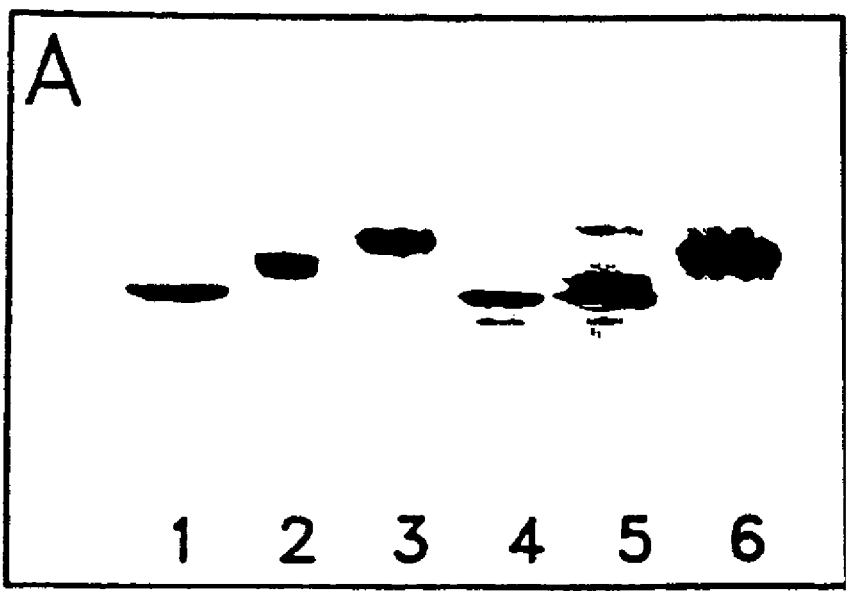
Figure 30B:
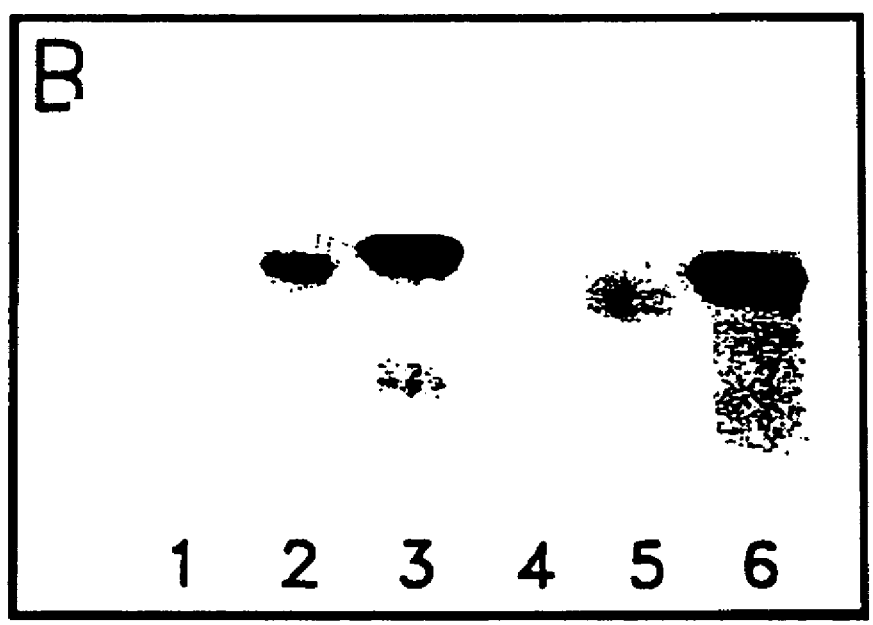

FIG. 30 (A–B): Mobility shift of htau23 versus mutant htau23/A404 upon phosphorylation with GSK3. Top, SDS gel, bottom, autoradiogram. Lanes 1–3, htau23 unphosphorylated and phosphorylated for 2 or 20 hours. Note the pronounced shift and the clear incorporation of phosphate. Lanes 4–6, mutant Ser404-Ala, unphosphorylated and phosphorylated for 2 and 20 hours. The shift after 2 hours is much smaller and the degree of phosphorylation much lower. This shows that the first strong shift and phosphorylation is at Ser404, similar as with MAP kinase and the brain extract kinase activity.

Figure 31:
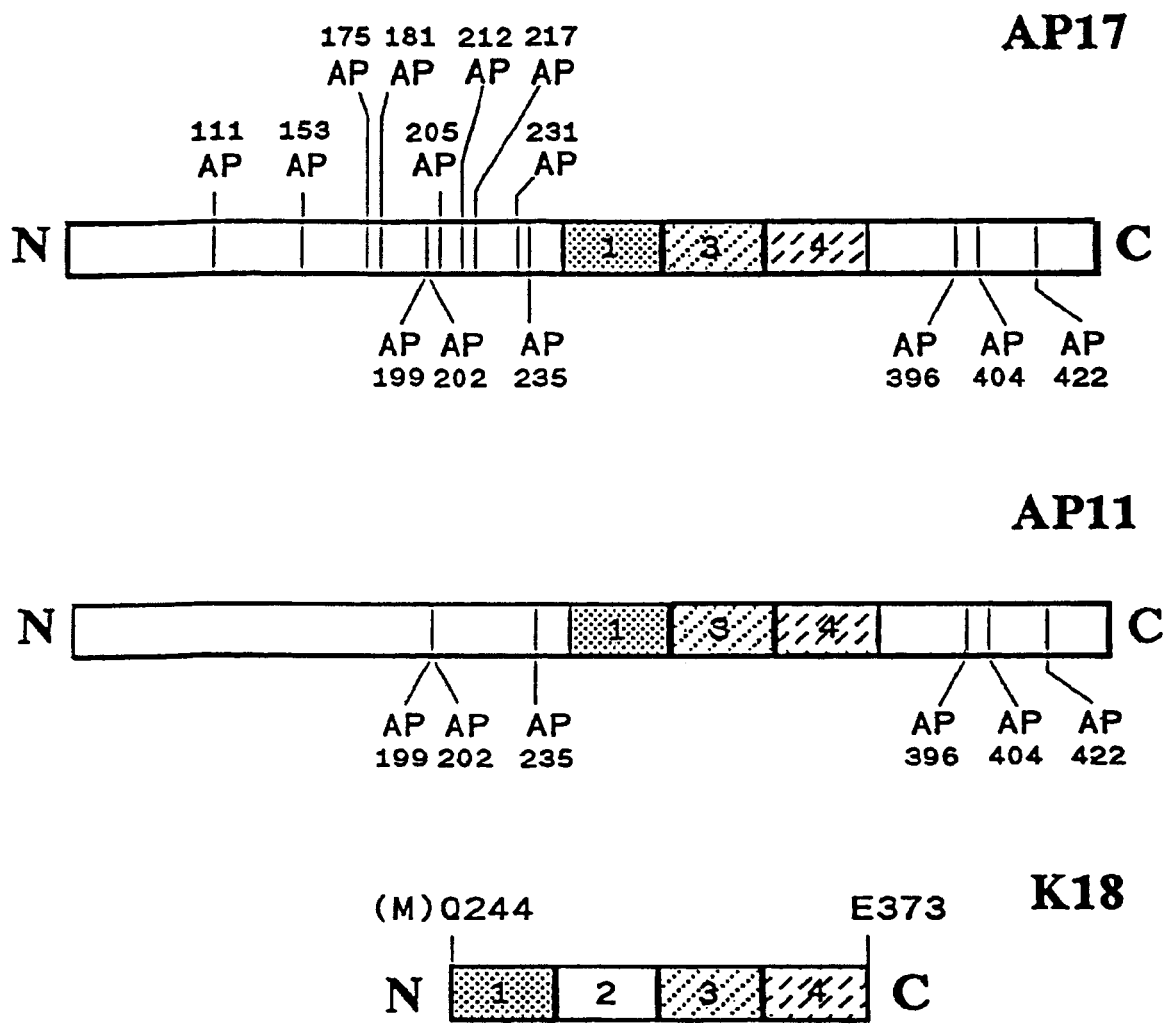

FIG. 31: Diagrams of tau constructs. Top, AP17, a derivative of htau23 with all Ser-Pro or Thr-Pro motifs altered into Ala-Pro. Middle, AP11, only Ser-Pro motifs changed into Ala-Pro. Bottom, K18, only 4 repeats of tau (derived from htau40).

FIG. 32: Copolymerization of MAP kinase and GSK3 with porcine brain microtubules. (A) SDS gel of microtubule purification stages. Ex=brain extract, supernatant after first cold spin. S=supernatant of first hot spin=tubulin and MAPs not assembled into microtubules after warming to 37.degree. C.; P=pellet of redissolved microtubules. The other lanes (S, P) show two further cycles of assembly and disassembly by temperature shifts (last pellet of microtubule protein was concentrated). (B) Blot with anti-MAP kinase, showing mainly the p42 isoform and some of the p44 isoform. (C) Blot with anti-GSK3B; note that this antibody shows some cross-reactivity with GSK3α. (D) Blot with anti-GSK3α. The blots show that both kinases and their isoforms co-purify with the cycles of microtubule assembly.

Figure 33A:
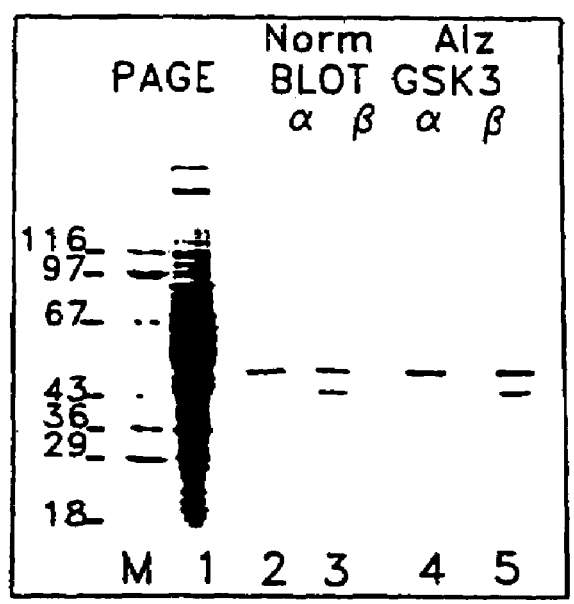
Figure 33B:
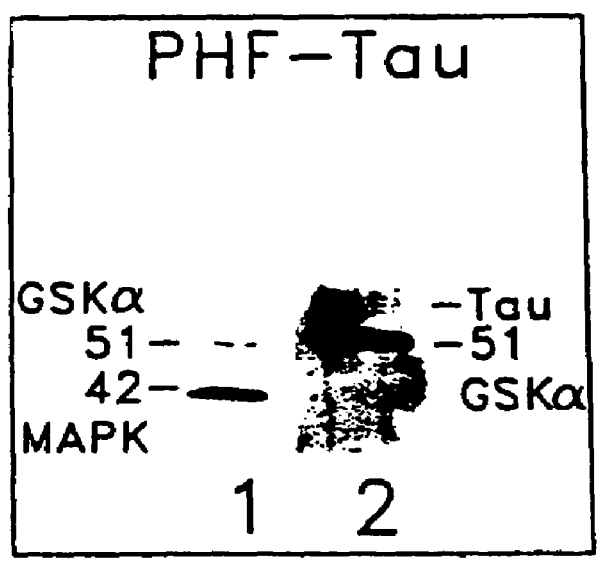

FIG. 33: (A) Identification of GSK3α and β in normal and Alzheimer brain extracts. M=markers, lane 1, SDS gel of normal brain extract, lane 2, immunoblot with anti-GSK3α; lane 3, immunoblot with anti-GSK3 β (with some cross-reactivity to α). Lanes 4 and 5, same blots with Alzheimer brain extracts. (B) Identification of GSK3 in association with PHF from Alzheimer's tau.

Figure 34:
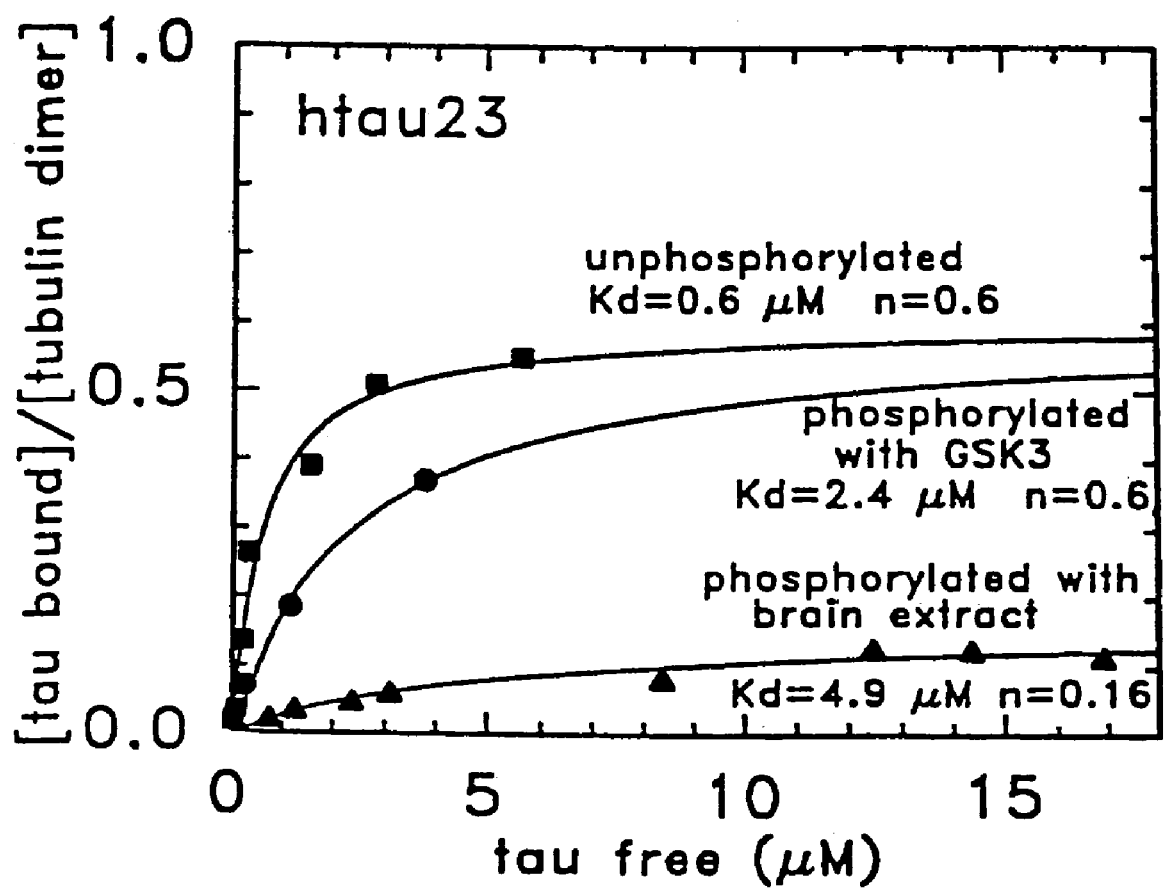

FIG. 34: Binding curves of htau23 to microtubules (made from 10 µM tubulin in the presence of 20 µM taxol). Top curve (squares), htau 23 unphosphorylated. Middle (circles), htau23 phosphorylated with GSK3, showing a comparable stoichiometry as the unmodified tau protein (saturating 0.6 per tubulin dimer). Bottom curve (triangles), control of htau23 phosphorylated with the brain kinase activity, showing a pronounced decrease in stoichiometry. The solid lines show the best fits assuming independent binding sites.

Figure 35A:
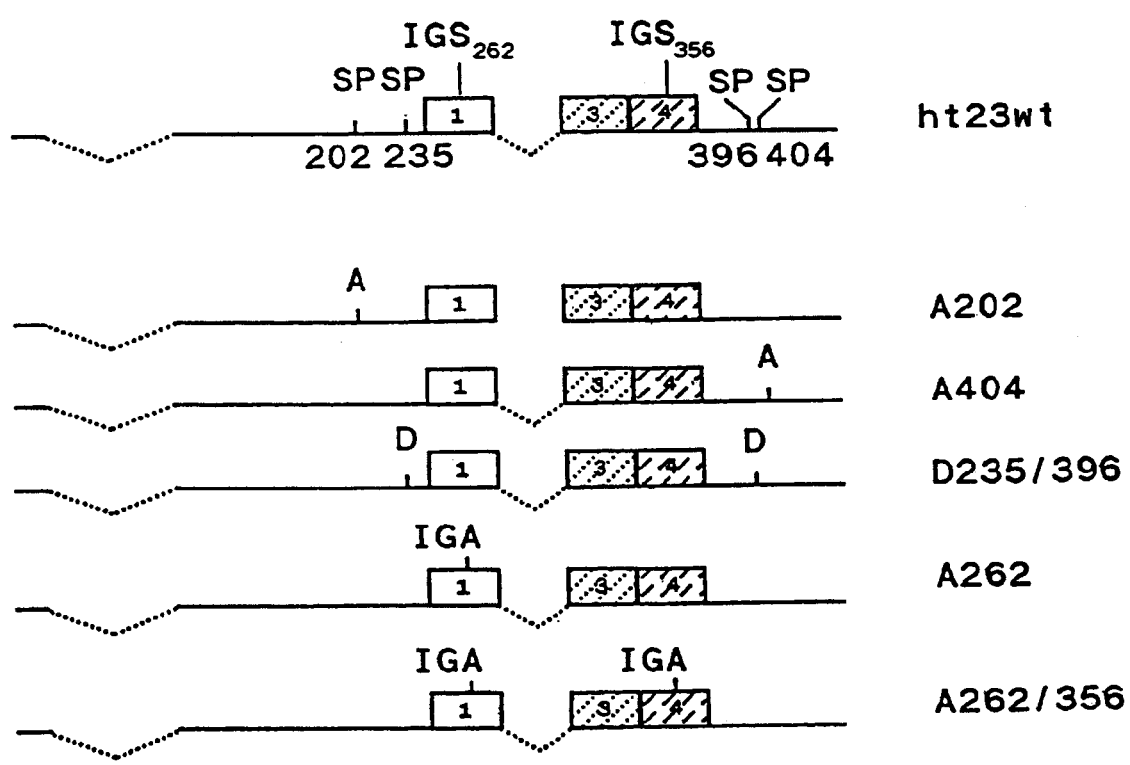

FIG. 35: (A) Diagram of htau23 and point mutants used in this invention. (B) Binding curves of htau23 and its point mutants to microtubules, unphosphorylated and phosphorylated with brain extract. The top and bottom curves show unphosphorylated and phosphorylated wild type htau23, the other curves are after phosphorylation. Mutants are (from top to bottom): Ser262-Ala, Ser235-Asp/Ser396-Asp, Ser404-Ala, Ser202-Ala. The mutation at Ser262 nearly eliminates the sensitivity of the tau-microtubule interaction to phosphorylation. These curves were derived from quantitating SDS gels by densitometry (see Example 6). Polymerized tubulin is 30 µM. The fitted stoichiometries n (=tau/tubulin dimer) and binding constants $K_d$(µM) are:

htau23wt non-phos. (n=0,49,$K_d$=2.5); A262 phos. (n=0.45,$K_d$=5.3); D235/D396 phos. A202 phos. (n=0.31,$K_d$=9.4); htau23wt phos. (n=0.16, $K_d$=4.9).

Figure 36:
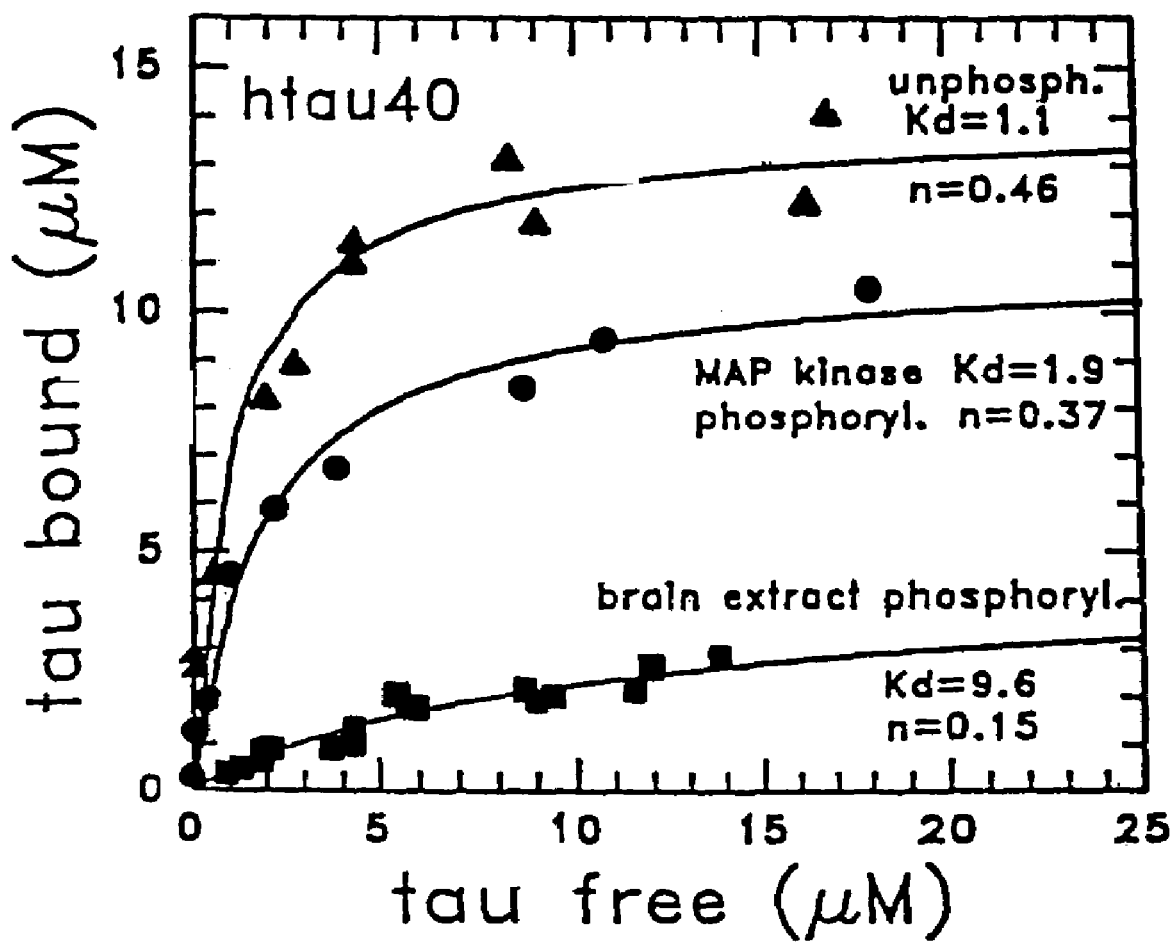

FIG. 36: Binding curves of htau40 to microtubules. Top, unphosphorylated htau40 (triangles); middle, htau40 phosphorylated with MAP kinase (circles); bottom, htau40 phosphorylated with brain extract (squares). Fitted dissociation constants $K_d$ and stoichiometries are as indicated.

FIG. 37: (A) Diagram of total mutant AP18. All Ser-Pro Thr-Pro are replaced by Ala-Pro. In addition, Ser262 and 356 are mutated into Ala. In the mutant AP17 Ser262 and Ser356 remain unchanged. (B) Binding curves of htau 23 and the "total" mutants AP17 and AP18 to microtubules without or with phosphorylation by brain extract. Top, unphosphorylated htau23 (filled triangles); middle, phosphorylated AP18 (circles), the two bottom curves are phosphorylated AP17 (open squares) and htau23 (open triangles). The difference in behavior between AP17 and AP18 is due to the phosphorylation of Ser262 in AP17. Fitted stoichiometries and binding constants are:

htau23wt non-phos. (n=0.49,$K_d$=2.5); AP18 phos (n=0.48, $K_d$=6.); AP17 phos (n=0.18,$K_d$=6.6); htau23wt phos. (n=0.16, $K_d$=4.9).

FIG. 38: Preparation of the kinase from porcine brain by chromatographic steps. (A) Mono Q HR 10/10 FPLC. The phosphorylation of recombinant human tau 34 and construct AP17 is shown on the y-axis as moles $P_i$ transferred per mole of tau. Fractions which decrease the binding of tau to MT elute around fraction 12, 20 and 30, the peaks around fractions 20 and 30 being the most effective. (B) Fractions 28–32 from Mono Q were gel filtrated on a Superdex G-75 HiLoad 16/60 column. The column was calibrated with standard proteins as shown by the filled symbols: Ribonuclease, 14 kDal; chymotrypsinogen A, 25 kDal; ovalbumin, 43 kDal; bovine serum albumin, 67 kDal. Molecular weight is indicate on the right y-axis on a logarithmic scale. The phosphorylation of htau34 and construct K18 is shown on the left y-axis. The highest activity elutes at a Mr of approx. 35 kDal. (C) Fractions 17–23 from the gel filtration column were pooled and rechromatographed on a Mono Q HR 5/5 column. Fraction 10 was used for binding studies. (D) SDS-gel showing the main purification stages. M: Marker proteins; lane 1, whole brain extract, lane 2, Mono Q HR 10/10 FPLC, fraction 30; lane 3, Superdex gel filtration, fraction 22; lanes 4–5, Mono Q HR 5/5 FPLC, fractions 10 and 9. Lane 5 shows the purified 35 kDal band and a trace at 41 kDal.

Figure 38C:
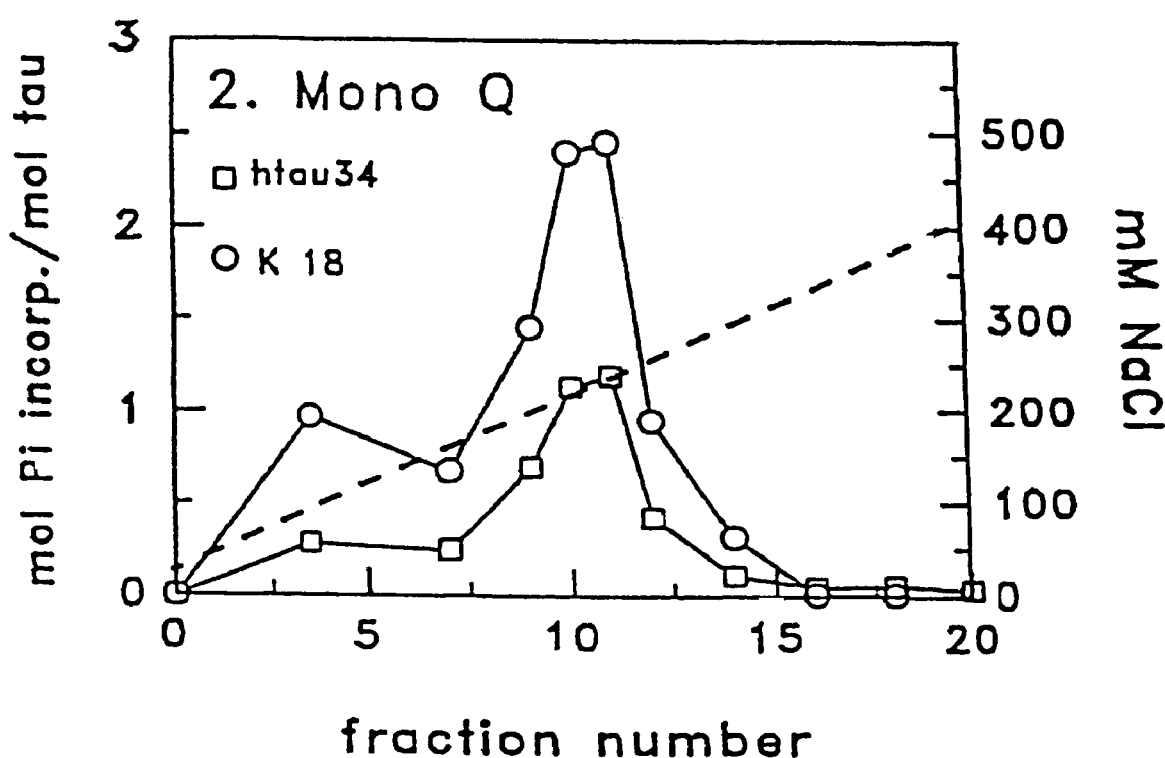
Figures 39A, 39B, 39C:
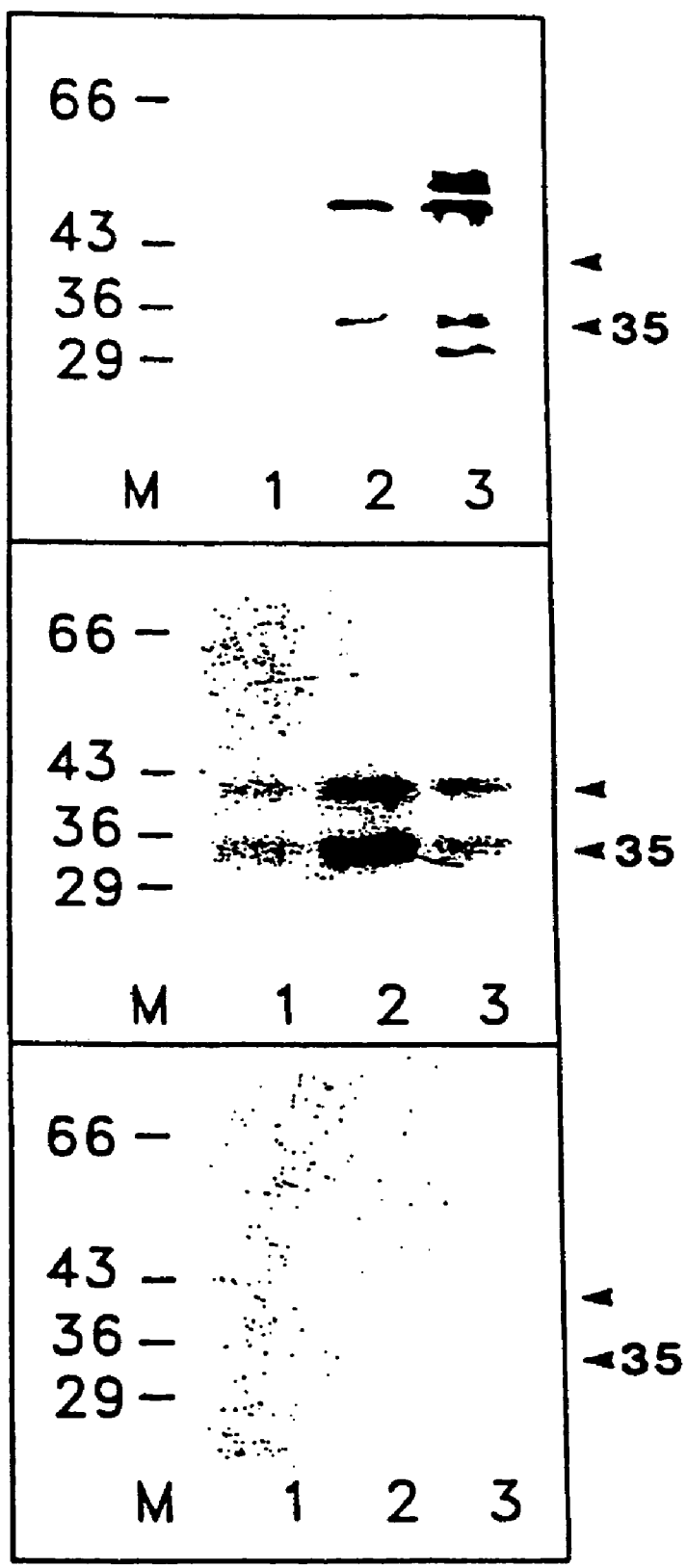

FIG. 39: SDS gel and in-gel assay of kinase activity (for details see Example 11). (A) 7–15% silver stained SDS gel of fractions 9–11 (lanes 1–3) of second Mono Q run (see FIG. 38c). (B) Autoradiogram of an in-gel experiment, with tau construct K9 (=four repeats plus C-terminal tail of tau) in the gel and 5 µl each of fractions 9–11 (lanes 1–3). (C) Autoradiogram of control gel containing no tau protein and showing no autophosphorylation of the Mono Q fractions. Note that specific kinase activities are difficult to quantify from these gels since the renatured protein tends to diffuse out of the gels; this is especially true of the 35 kDal band.

FIG. 40: Effect of phosphorylation of tau by 35 kDal kinase on gel shift and microtubule binding. (A) SDS gel of htau23 and constructs phosphorylated by several kinases. M, marker proteins. Lanes 1 and 2, htau23 without and with phosphorylation by 35 kDaI kinase. Lanes 3 and 4, same experiment with point mutant htau23(Ser409-Ala) (no shift); lanes 5 and 6, point mutant htau23(Ser416-Ala) (only part of the protein phosphorylated, but otherwise same shift as in lane 2); lanes 7 and 8, point mutant htau23(Ser404-Ala) (same shift as lanes 2 and 6). The mutants show that the 35 kDal kinase induces a shift by phosphorylating Ser4O9. Note that Ser404 is the target of MAP kinase, Ser416 of CaM kinase (Steiner et al., 1990, ibid.), and Ser409 and Ser416 of PKA, each of which induces a shift. Lanes 9–11 show a comparison of the shifts induced in htau23 by the different kinases (CaM kinase, PKA and MAP kinase). The shifts induced by PKA (lane 10) is the same as that of the 35 kDal kinase, and that MAP kinase produces by far the largest shift, typical of the Alzheimer-like state of tau. The bars on the right indicate the shift level; from bottom to top, unphosphorylated htau23 (control), CaM kinase shift level, PKA shift level, MAP kinase shift level. All shift sites are near the C-terminus. (B) Binding curves of htau23 and the mutants Ser262-Ala to microtubules without or with phosphorylation by the 35 kDal kinase (Mono Q fraction 10, 20 hours). Top, unphosphorylated htau23 (open circles, n=0.49, $K_d$=2,5 µM); middle, phosphorylated mutant (squares, n=0.44, $K_d$=11.6 µM); bottom, phosphorylated htau23 (filled circles, n=0.21, $K_d$=8.8 µM). In the absence of Ser262 the reduction in stoichiometry is 0.05; with phosphorylated Ser262 it is 0.28.

Figure 41:
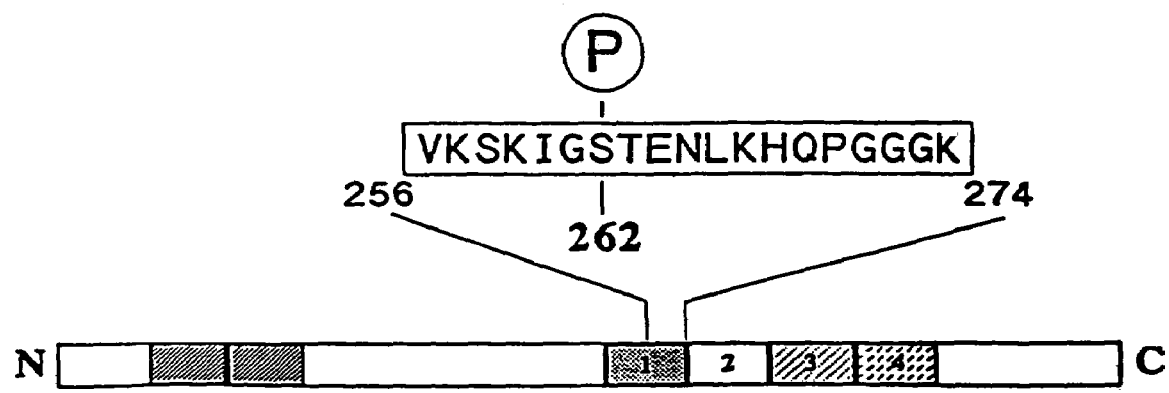

FIG. 41: Diagram of htau40, highlighting the first microtubule-binding repeat (SEQ ID NO: 30) and the Ser262 that is important for microtubule binding.

FIG. 42: 1. Dephosphorylation ("dephos.") of p32-marked htau40 ("ht40.sup.32P") with different PPases. Autodiagraphs of 7–15% SDS gradient gels. FIG. 1: Autoradiographs of 7–15% SDS gradient gels.

A. Dephos. with PP2a H-isoform (10 µg/ml) Lane 1: ht40P before dephos. Lane 2: 10 mm dephos. Lane 3: 30 mm dephos. Lane 4: 120 mm dephos.

B. Dephos. with PP2a M-isoform (10 µg/ml), Lanes 1–4: see A.

C: Dephos. with PP2a L-isoform (10 µg/ml), Lanes 1–4: see A.

D: Dephos. with catalytic subunit of PP1(500 U/ml), Lanes 1–4: see A.

FIG. 43: 2. Dephosphorylation with PP2a-H: disappearing of phosphorylation dependent antibody epitopes A. SDS-PAGE (7–15%). Lane 1: ht40P before dephos. Lane 2: 10 mm dephos. Lane 3: 30 mm. phos. Lane 4: 120 mm dephos. Lane 5: 5 h dephos. Lane 6: 16 h dephos.

B. Autoradiographs
C. Immunoblot AT-8
D. Immunoblot Tau-1A
E. Immunoblot SMI-33

Figure 44A:
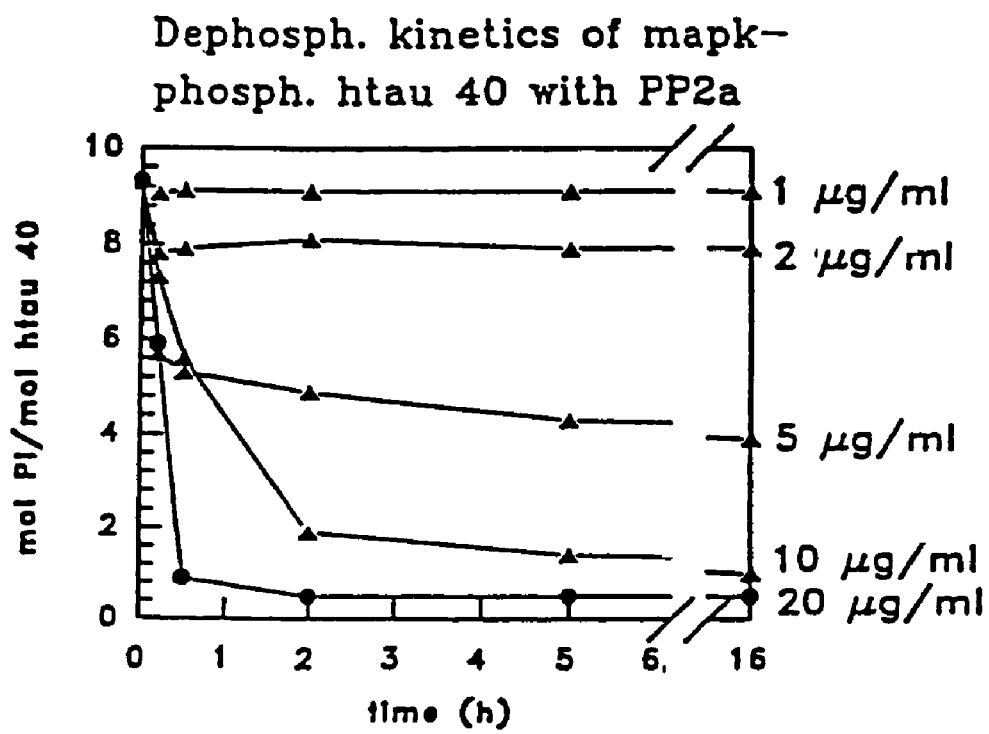
Figure 44B:
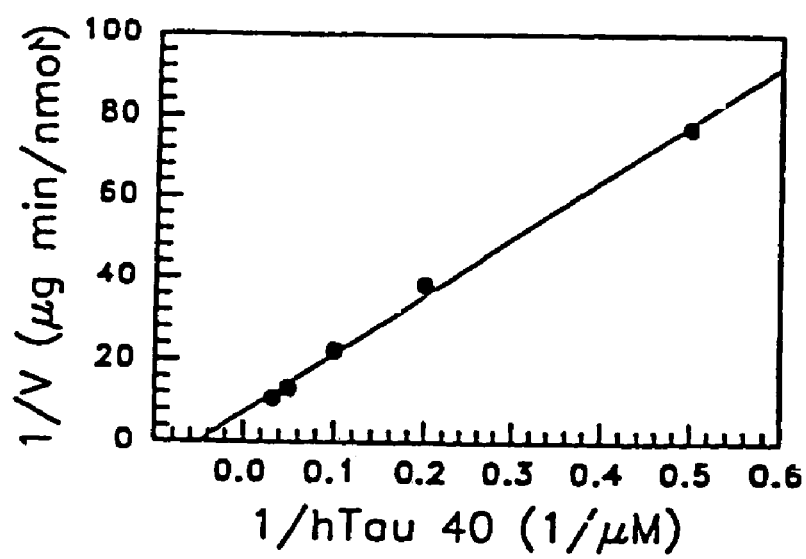

FIG. 44: Kinetics of dephos. with PP2a-H

A. time course of dephos. of ht40P with different concentrations of PP2a

B. variation in the ht40P-concentration: Michaelis-Menten-Diagramm.

FIG. 45: Preparation of the 70 kDal kinase which phosphorylates the two IGS motifs and the two CGS motifs of tau protein (Serines 262, 293, 324, 409). The kinase strongly reduces the affinity of tau for microtubules.

(A) Chromatography on S-Sepharose. Kinase activity elutes at 250 mM NaCl.

(B) Chromatography on heparin agarose. Kinase activity elutes at 250 mM NaCl.

(C) Gel filtration on Superdex G-75. Kinase activity elutes at 70 kDal.

FIG. 46: Time course of phosphorylation of htau40 with cdk2/cyclin A. Lanes 1–9 correspond to time points 0, 10, 30, 90 min, 3, 6, 10, 24 hours, and 0 mm (the 0 min lanes are the control).

(A) SDS polyacrylamide gel electrophoresis, showing the shift of the protein upon phosphorylation.

(B) Autoradiogram showing increasing incorporation of phosphate.

(C) Immunoblot with TAU-1 antibody which recognizes only unphosphorylated Ser199 nd Ser202.

(D) Immunoblot with AT-8 antibody which recognizes these two serines in a phosphorylated state, as well as Alzheimer tau.

EXAMPLE 1

Preparation of Tau Protein

Preparation of tau from normal brains: The procedures of tau preparation from human, bovine, or porcine brain, dephosphorylation, and rephosphorylation were essentially as described by Hagestedt et al., J. Cell. Biol. 109 (1989), 1643–1651.

Preparation of tau from Alzheimer brains: Human brain tissues from neuropathologically confirmed cases of Alzheimer's disease were obtained from various sources. The autopsies were performed between 1 and 25 hours post mortem.

The brain tissue was kept frozen at −70° C. Tau from paired helical filaments (PHF) was prepared according to Greenberg & Davies, Proc. Natl. Acad. Sci. USA 87 (1990), 5827–5831.

EXAMPLE 2

Characterization and Partial Purification of the Tau Phosphorylating Activity (Protein Kinase) of Porc Brain Extract Porc brain extract supernatant was fractionated by ammonium sulphate precipitation. The main kinase activity precipitated at 40% saturation. This fraction was desalted by gel filtration, diluted fivefold and incubated in activation buffer (25 mM Tris, 2mM EGTA, 2mM DTT, 40mM p-nitrophenylphosphate, 10 µM okadaic acid, 2 mM MgATP, protease inhibitors) for 2 hours at 37° C. During this incubation a phosphorylation of a 44 kD protein at tyrosine residue(s) occurs as shown by Western blotting with anti-phosphotyrosine mAb. The 44 kD protein could be identified as MAP2 kinase by a second mAb.

The crude enzyme activity was further purified by ion exchange chromatography (Mono Q FPLC, Pharmacia). Fractions containing the activated MAP-Kinase, as shown by Western blotting, exerted the most prominent tau phosphorylating activity (Peak I). A second tau phosphorylating activity (Peak II) did not induce comparable SDS-gel shifts and Alzheimer-specific antibody reactivity in tau.

EXAMPLE 3

Construction of Plasmids Carrying Genes Encoding Recombinant Tau Polypeptides for the Determination of Alzheimer Tau Protein Specific Epitopes Cloning and expression of tau constructs: Plasmid preparations and cloning procedures were performed according to Sambrook et al. (Molecular Cloning Laboratory Handbook, 2nd edition, Cold Spring Harbor Laboratory, Cold Spring Harbor, 1989). Amplifications by the polymerase chain reaction (PCR, Saiki et al., Science 239 (1988), 487–491) were carried out using Taq polymerase as specified by the manufacturer (Perkin Elmer Cetus). The tau genes and their constructs were expressed in the expression vector pNG2, a derivative of pET-3b (Rosenberg et al., Gene 56 (1987), 125–135), modified by removal of PstI, HindIII, NheI and EcoRV restriction sites for convenient engineering of the tau gene. For the expression the BL21 (DE3) *E. coli* system (Studier et al., Meth. Enzym. 185 (1990), 60–89) was used. Most constructs were derived from the human isoform htau23 which contains 352 residues and three internal repeats in the C-terminal microtubule binding region (Goedert et al., Proc. Natl., Acad. Sci. USA 85 (1988), 4051–4055). The numbering of residues used here refers to the sequence of htau40, the largest of the human isoforms (441 residues, Goedert et al., ibid.). For the isolation of the constructs use was made of the heat stability of the protein; they were separated by FPLC Mono S (Pharmacia) chromatography according to the procedure described by Hagestedt et al., J. Cell. Biol. 109 (1989), 1643–1651.

K10: This represents the carboxy part of the htau23 isoform consisting of 168 residues (Q244-L441 plus start methionine, but without the second repeat V275–S305). The K10 tau cassette was generated in the pNG2/htau23 vector by deletion of the NdeI-PstI fragment and replacing it with a chemically synthesized hexamer 5'TATGCA3'. After religation the NdeI endonuclease site was restored and PstI site was damaged.

Constructs K11 and K12 were made by a combination of fragments derived from the htau23 and htau24 genes. K11 is a tau derivative containing 4 repeats and consists of 152 amino acids (Q244-Y394 plus start methionine). K12 is a tau derivative containing 3 repeats and consists of 121 amino acids (Q244-Y394 plus start methionine, but without the second repeat V275-S305, htau40 numbering).

Htau23 and htau40 are human tau isoforms consisting of 352 and 441 amino acids, respectively (8).

K17: The K17 tau cassette (145 residues) is a shorter derivative of K16. It was made in two steps: First K16 was constructed using PCR to engineer the htau24 gene. The 5' "add on" of restriction sites on both ends of the amplified fragment was applied to facilitate the insertion of the PCR products into the cloning vector. The start primer (JB50) had the sequence GGCG ("G/C clamp"), the CATATG recognition site for the NdeI nuclease (containing the universal ATG start codon), followed by coding information for amino acids S198-T205. The stop primer (JB51) had a "G/C clamp" and the GGATCC recognition sequence for BamHI followed by a stop anticodon and anticoding sequence for the C terminal amino acids P364-E372. The K16 tau cassette consists of 176 residues, 175 from htau40 (S198-E372) plus a start methionine. This fragment represents part of the assembly domain consisting of 46 residues between S198 and the beginning of the first repeat following by the sequence of four repeats finished at E372. In the second step, a BstXI-BstXI fragment from the newly constructed tau K16 cassette was exchanged against the similar BstXI-BstXI fragment from the htau23 gene containing only three repeats and causing the generation of the tau cassette K17. Thus K17 represents the analogous part of the projection domain like K16 but missing the second tau repeat.

K3M (355 residues) is a chimera consisting of 145 residues from the amino terminus of bovine Tau4 (from the plasmid pETNde43-12, Himmler et al., Mol. Cell. Biol. 9 (1989), 1381–1388) and 190 residues from carboxy part of human htau23 (from the plasmid pUC18/htau23, Goedert et al., 1988 ibid.). It is a molecule with three repeats and two amino terminal inserts, consisting of 29 residues each. K3M was constructed by excision of XmaI-BclI fragment from pETNde42-12 and replacing it with analogous XmaI-BclI fragment originated from the htau23 gene. This manipulation removed 64 residues (XmaI-XmaI segment from bTau4) and replaced the 4 repeats carboxy terminus against three repeats carboxy terminus.

K19 represents the three repeats of htau23 and consists of 99 residues (Q244-E372, plus start methionine, without repeat 2). The K19 molecule was constructed from K17 by replacing the 144 nt long NdeI-PstI fragment with the synthetic hexamer 5'TATGCA3'. This modification retains the intact NdeI restriction site in the beginning of the molecule and removes the PstI site.

Construction of the D-mutant of htau23: In order to replace S199 and S202 by D in htau23, a double stranded DNA cassette encoding the amino acids G164-P219 was designed. This DNA segment was assembled from 8 oligonucleotides (30 to 60 nucleotides in length) and contained SfiI and XmaI sticky ends. The insertion of the assembled cassette into linearized pNG2/htau23 vector with removed native SfiI-XmaI fragment created the required gene.

Construction of htau23/A404: htau23/A404 is a mutated htau23 molecule where Ser404 was replaced by the Ala in order to remove this phosphorylation site. For convenient manipulation of the htau23 gene, an artificial NcoI restriciton site in the position 1161 (htau40 numbering) was introduced. This mutation was done using PCR-SOE (splicing by overlap extension, Higuchi et al., Nucl. Acids. Res. 16, (1988), 7351–7367). The new NcoI does not influence the amino acid sequence of tau protein. For the introduction of the Ala residue in the position 404 a synthetic DNA cassette was used, representing the 120 bp DNA fragment between NcoI and NheI restriction sites and encoding the amino acids His388-Thr427. This DNA segment was assembled from 4 oligonucleotides (54 to 66 nucleotides in length) and contained NcoI and NheI sticky ends. The insertion of the assembled cassette into the linearized pNG2/htau23/NcoI vector with removed native NcoI-NheI fragment created the htau23/A404 gene. The mutation of Ser396 to Ala was created in similar way like that in the position 404.

K2 (204 residues) is a chimera consisting of 36 residues from the amino terminus of bovine Tau4 and 168 residues from the carboxy part of htau23; it contains three repeats. K4-K7 are deletion mutants of htau23 containing only two repeats: K4 has repeats No. 1 and 3 (270 residues, D345-A426 excised); K5 has repeats No. 1 and 3 (310 residues, D345-T386 excised); K6 has repeats No. 3 and 4 (322 residues, T245-K274 excised); K7 has repeats No. 1 and 4 (321 residues, V306-Q336 excised); note that repeat No. 2 is always absent in htau23. K13-K15 are deletion mutants of htau23 containing only one repeat: K13 has repeat No. 4 (291 residues, T245-Q336 excised); K14 has repeat No. 3(279 residues, T245-S305 and D345-D387 excised); K15 has repeat No. 1 (278 residues, D345-D387 excised).

EXAMPLE 4

Determination of Alzheimer Specific Epitope in the Tau Protein

A panel of antibodies against PHFs from Alzheimer brain was closely examined for their reactivity and one (AT8) was found that was specific for PHF tau. FIG. 1 shows the reactivity of the antibody AT8 against different tau species. In the case of tau from Alzheimer paired helical filaments (PHF) the antibody recognizes all isoforms (FIG. 1b, lane 1). When the mixture of tau isoforms from normal bovine or human brain was tested (known to be in a mixed state of phosphorylation, FIG. 1a, lanes 2–5), reactivity with the AT8 antibody (FIG. 1b) was detected. The same is true for the six individual human isoforms expressed in E. coli (unphosphorylated, FIGS. 1a and 1b, lanes 6–11). It is concluded that AT8 is indeed specific for Alzheimer tau; in particular, it reacts with a phosphorylated epitope that occurs only in PHFs, but not in normal tau. Moreover, there is a correlation between the AT8 reactivity, phosphorylation, and electrophoretic mobility; it appears as if there was an Alzheimer-like phosphorylation that caused an upward shift in the SDS gel.

Figure 2A:
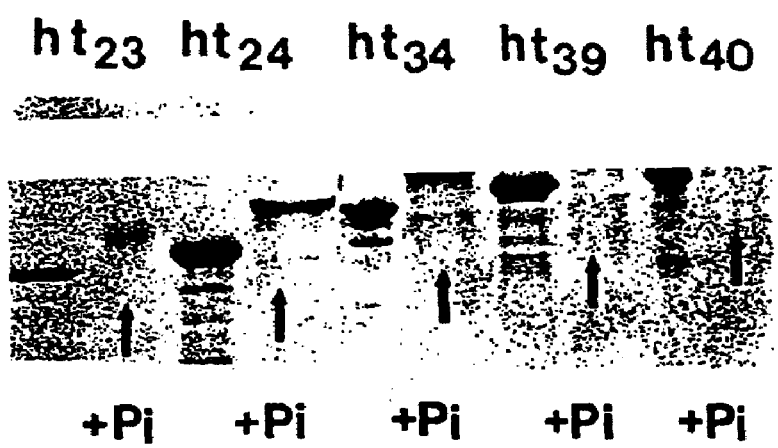
Figure 2B:
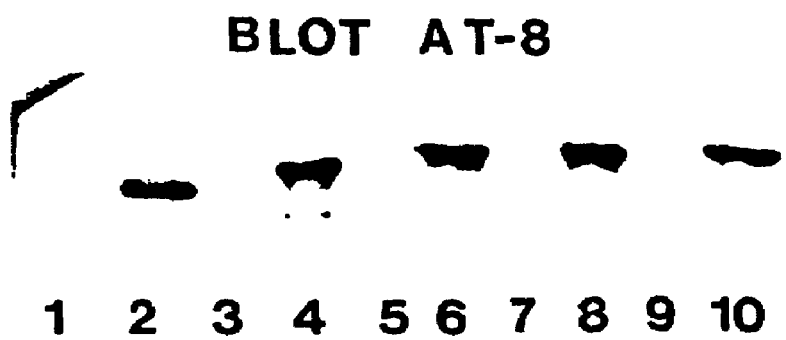

In order to identify the kinase(s) that were responsible for this behavior, and the corresponding phosphorylation sites, a kinase activity from porcine brain extract was prepared as described in Example 2. The six human isoforms expressed in E. coli were phosphorylated according to standard procedures with this activity in the presence of okadaic acid, a phosphatase inhibitor. FIG. 2a shows that each isoform changes considerably its electrophoretic mobility in the gel (upward shift) and shows a strong immunoreactivity with the AT8 antibody (FIG. 2b). These results show that the phosphorylation of tau by this kinase activity is analogous to that of the Alzheimer state. Moreover, since all isoforms are affected in a similar way the phosphorylation site(s) must be in a region common to all of them.

Figure 4A:
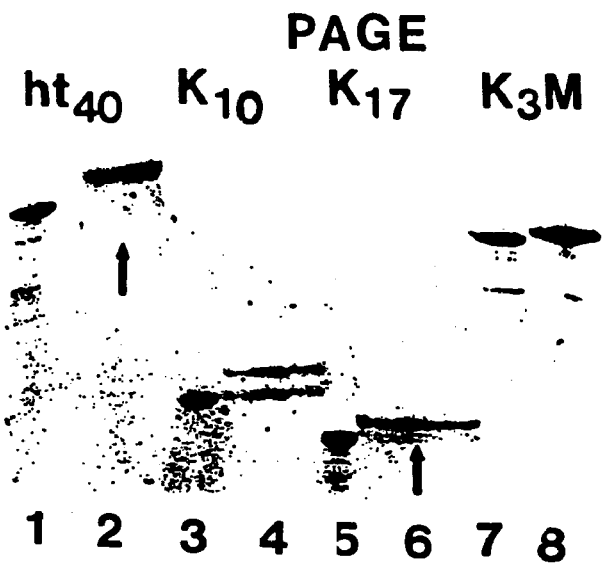
Figure 4B:
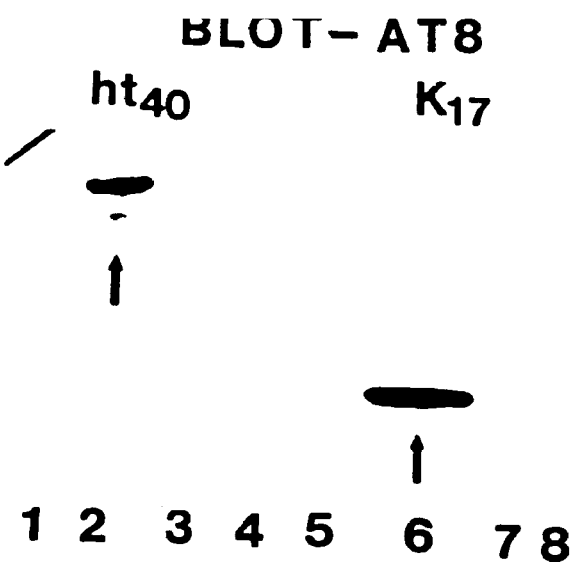
Figure 4C:
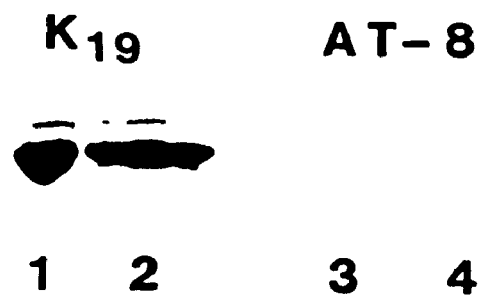

The strategy to identify said common region was to use first the engineered mutants prepared as described in Example 3 in order to narrow down the site, and then to determine it by direct sequencing. FIG. 3 describes some of the mutants used, K19, K10, K17, and K3M (see also Example 3). Except for K19, all of these mutants are phosphorylated by the kinase activity and show an upward $M_r$ shift in the SDS gel (FIG. 4a). K19 is a construct that comprises just three repeats of 31 or 32 residues. It does not become phosphorylated by the kinase activity and therefore does not show an $M_r$ shift in the SDS gel (FIG. 4c).

This means that the phosphorylation site(s) are outside the region of the repeats. Phosphorylation can take place on either side of the repeats and induces an upward shift in the gel; the shift is larger for phosphorylation after the repeats. The antibody AT8 recognizes none of the unphosphorylated forms (as expected); after phosphorylation it reacts only with the construct K17 (FIG. 4b, lane 6), not with K10 or K3M (FIG. 4b, lanes 4 and 8). In other words, K17 retains the epitope, while K10 and K3M have lost it. By reference to FIG. 3 it is concluded that the epitope is not in the region of the pseudo-repeats nor in C-terminal tail where we found a CaM kinase site previously (since K10 and K19 are non-reactive), but rather it has to be between S198 and T220 (FIG. 3, peptide P), i.e. in the region following the major chymotryptic cleavage site (behind Y197) in the "assembly" domain of tau.

Next a total tryptic digest of radioactively labeled htau34, an isoform with 4 internal repeats (Goedert et al., 1989, ibid.) was carried out. The peptides were isolated by HPLC and sequenced. One of them was in the area of interest, S195-R209 (FIG. 5). This peptide contained two phosphates at S199 and S202. Both are followed by a proline, suggesting that the enzyme active in the extract was a proline-directed kinase.

These results suggested that the phosphorylation sensitive AT8 epitope might be in the vicinity of residue 200. This was tested by engineering a mutant of htau22 (3 repeats, no N-terminal insert) where S199 and S202 were both changed to D. This choice was made in order to rule out the phosphorylation of these residues by a kinase, but also to mimick in part the "phosphorylated" state in terms of negative charges. On SDS gels this mutant showed a small upward shift to higher M (FIG. 6, lane 4). The immunoblots show that only the parent protein htau23 reacted with the antibody after phosphorylation (FIG. 6, lane 6), but not the unphosphorylated htau23 (as expected) nor the mutant, whether phosphorylated or not (lanes 7, 8).

It is concluded that the epitope of AT8 is in the region S199-S202 and depends on the phosphorylation of these two serines. They can be phosphorylated by a proline-directed kinase present in brain extract which turns the protein into an Alzheimer-like state. The region is perfectly conserved in all tau variants known so far and explains why all of them respond to phosphorylation and to the antibody in the same way.

EXAMPLE 5

Characterization of the Protein Kinase Activity

Phosphorylation of tau proteins was carried out in the following way: Tau protein (0.5 mg/ml) was incubated for various times (up to 24 hours) at 36° C. with the brain extract in 40 mM HEPES containing 2 mM $MgCl_2$, 1 mM DTT, 5 mM EGTA, 1.5 mM PMSF, 2 mM ATP, 20 µg/ml protease inhibitor mix (pepstatin, leupeptin, alpha-macroglobulin, aprotinin), with or without 1 mM okadaic acid. After that 500 mM DTT were added, the solution was boiled for 10 min and centrifuged for 15 min at 15000 g at 4° C. The supernatant was dialyzed against reassembly buffer (RB, 100 mM Na-PIPES pH 6.9, 1 mM EGTA, 1 mM GTP, 1 mM $MgSO_4$, 1 mM DTT) and used for binding studies.

Radioactive labeling was done with gamma-[$^{32}$P]ATP (NEN Du Pont) at 10 mCi/ml, 3000 Ci/mmol, diluted to 15–30 Ci/mol ATP for autoradiography on SDS gels. The phosphate incorporated into the protein was quantified as follows: 1 µg of phosphorylated protein was applied to SDS gels, the bands were cut out and counted in the scintillation counter in Cerenkov mode. The counter was calibrated with known samples of $^{32}$p (detection efficiency about 50% in Cerenkov mode). The corrected counts were translated into moles of $P_i$ per mole of tau on the basis of the known specific activity of radioactive ATP used during phosphorylation.

A remarkable feature found for this kinase is that it shifts the $M_r$ of all tau isoforms in three distinct stages (see FIGS. 7a and 8a for the case of htau23). During the first two hours of phosphorylation the protein is converted from a $M_{r0}$=48 kD protein to a slower species, with an $M_{r1}$ of about 52 kD. Upon completion of this first stage, a second one sets in which is finished around 6.10 hours ($M_{r2}$=54 kD), The third stage takes about 24 hours ($M_{r3}$=56 kD), after that no more shift is observed.

During the initial stage each band of the tau doublet incorporates phosphate (e.g. at a level of about 0.5 $P_i$ per molecule in the presence of OA at 30 min, see FIG. 7b, lane 4). This means that there must be at least two distinct phosphorylation sites, one that is responsible for the shift (the "shift site", upper band), and one that has no effect on the $M_r$ (lower band). The lower band gradually disappears, and at two hours each tau molecule contains about 2 $P_i$. In other words, the upper band contains tau molecules in which the "shift site" is phosphorylated, irrespective of the other site(s); whereas the lower band contains only molecules where the shift site is not phosphorylated. The effect of OA is seen mainly in the lower band, indicating that the phosphatase operates mainly on the non-shift site(s). These considerations apply to the first stage of phosphorylation; during the second and third stages there are further shifts, but a detailed analysis of shift sites and non-shift sites is not possible because of the overlap of bands. Overall about two additional phosphates can be incorporated in every stage, giving a maximum of 6 for htau23 and 7 for htau34. These values refers to the presence of OA; without it we usually find ≈1–2 $P_i$ less. When the purified kinase is used, one finds 12–14 $P_i$.

Since the major shift occurs during the first stage, and since a large shift is considered a hallmark of Alzheimer tau, it was suspected that the first stage phosphorylation might induce an Alzheimer-like state. This was checked by immunoblotting according to standard procedures with Alzheimer-specific antibodies. FIG. 8a shows a similar phosphorylation experiment as above (with 10 µM OA throughout), FIG. 8b is the immunoblot with the monoclonal antibody SMI34 which reacts with a phosphorylated epitope in Alzheimer tangles (Sternberger et al., ibid.). The antibody recognizes the bacterially expressed tau phosphorylated by the kinase, but only from stage 2 onwards. A similar behavior is found with other Alzheimer-specific antibodies tested. The result from these studies is that the major phosphorylation-dependent $M_r$ shift (stage 1) is distinct from the ones that generate the Alzheimer-like antibody response (stages 2, 3).

EXAMPLE 6

Tau Protein in Microtubule Binding Studies.

Another point of interest with respect to the correlation between abnormal phosphorylation of tau proteins and Alzheimer's disease was whether the phosphorylation had an influence on tau's affinity for microtubules. This was tested using a microtubule binding assay. Accordingly, PC tubulin was incubated at 37° C. in the presence of 1 mM GTP and 20 µM taxol. After 10 min tau protein was added in different concentrations and incubated for another 10 min. The suspensions were centrifuged for 35 min at 43000 g at 37° C. The resulting pellets were resuspended in CB buffer (50 mM PIPES PH 6.9, 1 mM EGTA, 0.2 mM $MgCl_2$, 5 mM DTT, 500 mM NaCl). In the case of htau 23 and htau 34 the pellets and supernatants were boiled for 10 min and recentrifuged for 10 min at 43000 g at 4° C. (this step served to remove the tubulin component which otherwise would overlap with these tau isoforms on SDS gels). Pellets and supernatants (containing the bound and the free tau, respectively) were subjected to SDS PAGE (gradient 7–15% acrylamide) and stained with Coomassie brilliant blue R250. The gels were scanned at 400 dpi on an Epson GT 6000 scanner and evaluated on a PC 368AT using the program GelScan (G. Spieker, Aachen). The protein concentration on the gel was always within the linear range (up to 1.5 optical density). The intensities were transformed to concentrations using calibration curves and used in the binding equation.

$\text{Tau}_{bound} = n[\text{Mt}][\text{Tau}_{free}]/\{K_d+[\text{Tau}_{free}]\}$, from which the dissociation constand $K_d$ and the number n of binding sites per dimer were obtained by fitting. [Mt] is the concentration of tubulin dimers polymerized in microtubules (usually 30 μM).

Figure 9C:
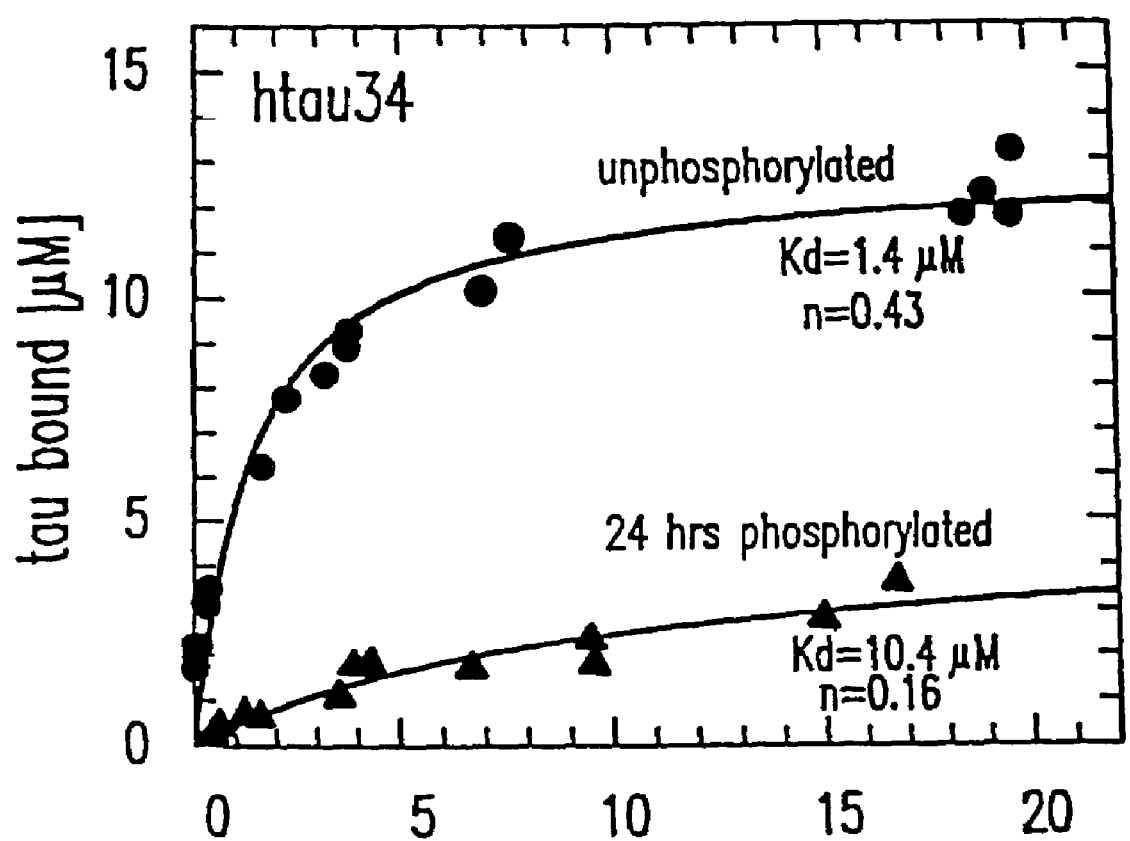

With fully phosphorylated protein (stage 3, 24 hours) a dramatic decrease in binding capacity of htau23 was observed (FIG. 9b), from about one tau per two tubulin dimers to one tau per six tubulin dimers. In other words, it appears that unphosphorylated tau packs tightly onto a microtubule surface, whereas fully phosphorylated tau covers the microtubule surface less densely, as if it occupied more space. FIG. 9c shows the same experiment with htau34. The results are similar, i.e. there is a threefold reduction in binding capacity. Tau isoforms with four repeats, such as htau34, bind to microtubules particularly tightly in the unphosphorylated state ($K_d$ 1–2 μM).

Since the major $M_r$ shift (see Example 5) occurs during the initial two hours it was of interest to find out which residues become phosphorylated during the first stage, and how they affected microtubule binding. As mentioned above, there are about two phospates incorporated during this period, one of which causes the shift from $M_{r0}$ to $M_{r1}$. FIG. 10 illustrates the binding of htau34 to microtubules after 90 min of phosphorylation. The striking result is that the limited phosphorylation decreases the affinity as efficiently as the full phosphorylation. This means that the reduction in microtubule affinity precedes the Alzheimer-like immunoreactivity (FIG. 8).

The analysis of tryptic peptides after 90 min showed four major peaks of radioactivity, with phosphates on serines 202, 235, 404, and 262. Three of these are SP sites that are not in the repeat region, but rather flank that region in nearly symmetric positions (FIG. 11); the fourth (S262) is a non-SP site in the first repeat. It is in particular note-worthy that S396 was not among the phosphorylated residues. This was unexpected since Lee et al. (1991, ibid.) had shown that S396 (the center of a KSP motif) was phosphorylated in tau from paired helical filaments. Thus S396 must become phosphorylated during the second or third stages of phosphorylation, concomitant with the immunoreactivity (FIG. 8b).

Several point mutants were generated according to standard procedures to find out which site(s) were responsible for the initial $M_r$ shift. When ser404 was turned into ala the $M_r$ shift during the first stage disappeared, whereas it remained visible when ser199, 202, 235, or 396 were mutated. This means that the phosphorylation of ser404 accounts for the one $P_i$ present in the upper band of FIG. 7a or 8a. The additional ≈$P_i$ present after 2 hours is distributed among serines 202, 235, and 404.

Whereas the results on the "shift site" S404 of tau are clear cut, the factors responsible for the reduction of microtubule binding are more complex. The S404-A mutant binds to microtubules similarly as the parent htau34; after 90 min of phosphorylation the stoichiometry decreases about 2-fold, i.e. less than the factor of 3 observed with the parent molecule. If S404 were the only residue whose phosphorylation was responsible for the loss of microtubule binding we would not expect any decrease in the mutant. The fact that a decrease is observed means that other factors play a role as well; these factors are presumably related to the incorporation of more than one $P_i$ at one or more of the other sites before or at the beginning of the repeat region (e.g. 202, 235, 262). However, these residues cannot by themselves be responsible for the full decrease of affinity either. In fact, point mutations at positions 202 or 235 show a similar effect as that of 404, i.e. only a partial reduction of binding. One possible explanation is that different phosphorylation sites interact in a cooperative manner and generate a new confirmation.

Example 7

Time Course of Phosphorylation as Determined by Stage Specific Antibodies

Neurofilament specific antibodies SMI31, SMI34, SMI35 and SMI310 against a phosphorylated epitope and SMI33 against a non-phosphorylated epitope [(Sternberger et al., Proc. Natl. Acad. Sci. USA 82 (1985), 4274–4276)] were used to detect stage specific phosphorylation of tau protein. SMI33 recognizes normal human brain tau (FIG. 12, lane 1) but does not recognize PHF tau, except when it is dephosphorylated (lane 4). This suggests that the epitope of SMI33 is specifically blocked by some phosphorylation in the Alzheimer state which does not. occur in normal brain tau. SMI31 and SMI34 both react in a complementary fashion to SMI33: Only PHF tau is recognized (FIG. 12c and 12d, lane 3), but not when it is dephosphorylated (lane 4), nor the normal tau control (lane 1).

The testing of the various antibodies during the time course of phosphorylation shows that SMI33 loses reactivity during the second stage of phosphorylation (see FIG. 7).

Figure 13E:
Figure 13F:
Figure 13G:
Figure 13H:
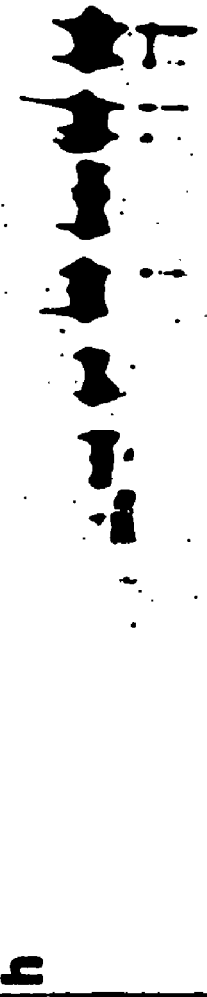

For antibody SMI31 no reactivity is observed with the unphosphorylated protein (time 0) or during the first stage, but the reactivity appears gradually during the second stage and remains throughout the third. A similar time course is found with antibody SMI34 (FIG. 13c and compare FIG. 12d, lane 3), SMI35, and SMI310 (FIG. 13g,h). For comparison the blots with AT8 (FIG. 13f), a phosphorylation sensitive Alzheimer tangle antibody (Binder et al., J. Cell. Biol. 101 (1985), 1371–1379 are included) and TAU1, an antibody against dephosphorylated tau. AT8 reacts similarly to SMI31, SMI34, SMI135, and SMI310, while TAU1 is similar to SMI33. The striking feature of the blots is that in each case it is the stage 2 phosphorylation that determines the antibody response.

These experiments could be interpreted by assuming that the antibodies react with the same region of tau in a dephosphorylated or phosphorylated form; but this assumption is too. simple, as shown later. Two other features should be pointed out, however: One is that the largest gel shift (stage 1) is not the one that causes the Alzheimer-like immunoreactivity (appearing in stage 2). Thus not every gel shift of tau is diagnostic of the Alzheimer state, although conversely the Alzheimer state always shows a gel shift secondly, there is a surprisingly precise relationship between gel shift, phosphorylation, and immunoreactivity with several different antibodies.

The major phosphorylated motifs of neurofilaments are repeated sequences of the type KSPV (SEQ ID NO: 38) where S is the phosphate acceptor; see e.g. Geisler et al., FEBS Lett. 221 (1987), 403–407. Tau has one such motif, centered at S396, and another KSP motif is centered at S235. The two KSP sites lie on either side of the repeat region and are conserved in all tau isoforms. By analogy one may suspect that these sites are involved in the reaction with the SMI antibodies that were raised against neurofilaments. We tested this in three ways, by mutating one or two of the serines, by making smaller tau constructs, and by direct sequencing of tryptic peptides.

Constructs K10, K17, and K19 were examined before or after phosphorylation with the kinase (FIG. 14a). K10 and K17 show an $M_r$ shift, but not K19. Note also that K10 and K17 are only partly converted to the higher $M_r$ form in this experiment, indicating that their phosphorylation is less efficient. K10 shows three shifted bands, indicating that there are three phosphorylation sites in the C-terminal region. K17 shows only one shifted band so that there is only one shift-inducing site in the region before the repeats. FIGS. 14b–d show the immunoblots with SMI33, SMI31, and SMI34; the data on SMI35 and SMI310 are similar to SMI31 (not shown). Antibody SMI33 reacts only with K17 in the dephosphorylated state, but not with K10 and K19 (FIG. 14, lane 3). This suggests that the epitope is in a region before the repeats, between S198 and Q244, outside the sequences covered by the other constructs. This would be consistent with an epitope at the first KSP site. Antibody SMI31 reacts with K10 in its phosphorylated form, but not K17 or K19 (FIG. 14). Using similar arguments as before, the epitope is in the region T373-L441, consistent with the second KSP site. Finally, antibody SMI34 labels htau23, K10 and K17, but not K19 (FIG. 14c). The latter property would argue against the repeat region as an epitope, but the remaining reaction with K10 and K17 would seem mutually exclusive. Our interpretations is that SMI34 has a conformational epitope that depends on tails on either side of the repeats and becomes fully stabilized only when at least one tail is present. However, the phosphorylation dependence is in each case the same as that of the intact molecule.

Since it was suspected that the two KSP motifs were phosphorylated by the kinase, it was tried to prove this directly. Radioactively labeled tryptic peptides of htau34 were identified by HPLC and protein sequencing, and phosphorylated residues were determined. There are two major phosphorylated tryptic peptides in these regions; peptide 1 (T231-K240, TPPKS$_P$PSSAK (SEQ ID NO: 33)) contains the first KSP motif, phosphorylated at S235, peptide 2 (T386-R406, TDHGAEIVYKS$_P$PVVSGDTS$_P$PR (SEQ ID NO: 35)) contains the second KSP site, phosphorylated at S396 and S404. S416, the single phosphorylation site of CaM kinase described earlier (Steiner et al. EMBO J. 9 (1990), 3539–3544, S405 in the numbering of htau 23 used earlier) is not phosphorylated by the kinase used here.

Next point mutants of the phosphorylated residues 235 and 396 (FIG. 15) were made and analysed in terms of gel shift and antibody reactivity (FIG. 16). The parent protein htau40 and its KAP mutants have nearly identical $M_r$ values, and they all shift by the same amount after phosphorylation (FIG. 16, lanes 1–8). The reactivity of SMI33 is strongly reduced when S235 is mutated to A (FIG. 16, lanes 3, 7) and obliterated after phosphorylation (FIG. 16, lanes 2, 4, 6, 8). This means that the epitope of SMI33 is around the first KSP site, but phosphorylation at other sites have an influence as well (perhaps via a conformation). The mutation at S396 (second KSP site) has no noticeable influence on the SMI33 staining (FIG. 16b, lanes 5, 6).

As mentioned above, the epitope of SMI31 depends on the phosphorylation of sites behind the repeat region. When S396 is mutated to Ala the antibody still reacts in phosphorylation dependent manner so that this serine is not responsible for the epitope by itself (FIG. 16c, lane 6). Mutation S404 to Ala yields the same result. However, if both serines are mutated, the antibody no longer reacts upon phosphorylation (not shown). This means that the epitope includes the two phosphorylated serines. The binding of this antibody also has a conformational component: constructs with only one repeat (K13-K15) are not recognized (FIG. 17, lanes 10, 12, 14).

SMI34 shows the most complex behavior because its reactivity depends on phosphorylation sites before and after the repeat region. This antibody recognizes all KAP mutats, so that S235 and S396 cannot play a major role. However, the fact that SMI34 recognizes phosphorylated K17, K10, but not K19 (FIG. 17) suggests that the regions before and/or behind the repeats must cooperate with the repeats to generate the epitope. One possibility would be that the epitope is noncontiguous, another one is that it may depend on the number and conformation of the repeats. In order to check these possibilities constructs with different combinations of two repeats (K5, K6, K7, FIG. 18), and constructs with one repeat only (K13, K14, K15) were done. All of these showed a shift upon phosphorylation, and all of them were recognized by SMI34 (the reaction is less pronounced when the third repeat is absent, indicating that this repeat is particularly important for the conformation, FIG. 17, lane 6). This means that the epitope of SMI34 does not depend on the number of repeats. However, the nature of the region just before the repeats seems to be important and in particular sensitive to charges. This can be deduced from constructs such as K2 or K3M where charged sequences have been brought close to the repeat region, resulting in a loss of SMI34 reactivity. In other words, it seems as if the charged sequences are capable of masking the epitope, independently of the phosphorylation itself (FIG. 17, lanes 2, 4). The interactions between the constructs and the antibodies are summarized in Table 1.

EXAMPLE 8

Cloning and expression of tau constructs: Plasmid preparations and cloning procedures were performed according to Sambrook et al. PCR amplifications were carried out using Taq polymerase as specified by the manufacturer (Perkin Elmer Cetus) and a DNA TRIO-Thermoblock (Biometra).

Tau cDNA clones and their constructs were subcloned into the expression vector pNG2 (a derivative of pET-3b, Studier et al., modified in the laboratory by removal of PstI, HindIII, NheI and EcoRV restriction sites for convenient engineering of the tau clones), or in expression vector pET-3a. For the expression, the BL21 (DE3) *E.coli* system was used (Studier et al.). All residue numbers refer to the sequence of htau40, the largest of the human isoforms (441 residues, Goedert et al.). For the isolation of the constructs the heat stability of the protein was used; they were separated by FPLC Mono S (Pharmacia) chromatography (for details see Hagestedt et al.).

Construction of T8R-1: This is a tau derivative containing 8 repeats. It was constructed on the basis of the bovine tau4 isoform (Himmler et al.). Two plasmids, pETNde43–12 (containing the btau4 gene) and pET-K0 (containing K0 which consists mainly of the four repeats plus leading and trailing sequences from the vector, Steiner et al.) were used for the construction of T8R-1. The NdeI-RsaI DNA fragment from btau4 was connected with "filled in" XmaI-BamHI fragment of K0 leading to chimeric molecule consisting of 553 amino acids. The T8R-1 gene encodes MetI-BaI393 connected through the artificially introduced Ser residue with the Gly248-Tyr394 tau fragment, followed by a 23 residue tail from the bacteriophage T7 sequence (htau40 numbering).

Construction of T7R-2 and T8R-2: T7R-2 is a tau derivative containing 7 repeats, T8R-2 contains 8 repeats. Both molecules were constructed on the basis of the human htau23 and htau24 isoforms (Goedert et al.). For the engineering of the T7R-2 and T8R-2 molecules, PCR repeat cassettes A1 (encoding 4 repeats), A2 (encoding the whole carboxy part of the tau24 molecule including the four repeat sequence and the tau sequence behind them) and A3 (encoding 3 repeats) were prepared. The T8R-2 molecule was generated by combination of A1 and A2 with NdeI-PstI DNA fragment isolated from htau23. This tau derivative consists of 511 amino acids, the first 311 N-terminal residues of htau24 (MetI-Lys369, containing 4 repeats), followed by Gly-Thr link, then by 198 residues of the C-terminus of htau24 (Gln244-Leu441, four more repeats). The T7R-2 gene was generated similarly to T8R-2 but the A3 cassette was used instead of A1. The T7R-2 protein consists of 480 amino acids, the first 280 N-terminal residues of htau23 (Met1-Lys369, including 3 repeats), followed by Gly-Thr link, then by 198 residues of the carboxy terminal part of htau 24 (gln244-Leu441, containing 4 repeats, htau40 numbering)

EXAMPLE 9

Conformation of Tau Protein and Higher Order Structures Thereof (a) Conformation and Dimerization of Tau Constructs FIG. 19 illustrates the types of constructs used in this example. Three types of molecules were used: (i) tau isoforms occurring in brain ranging from htau23 (the smallest isoform, 352 residues) to htau40 (the largest 441 residue, see Goedert et al.). They differ mainly by the number of internal repeats in the C-terminal domain (3 or 4) and the number of inserts near the N-terminus (0, 1, or 2). The internal repeats are involved in microtubule binding and in the formation of paired helical filaments; attention was then focused on the those constructs which would presumably yield information on the structure of the repeat region; (ii) engineered constructs with an increased number of repeats, e.g. seven or eight (T7, T8); (iii) constructs containing essentially the repeats only (e.g. K11, K12).

Figures 20A, 20B, 20C:
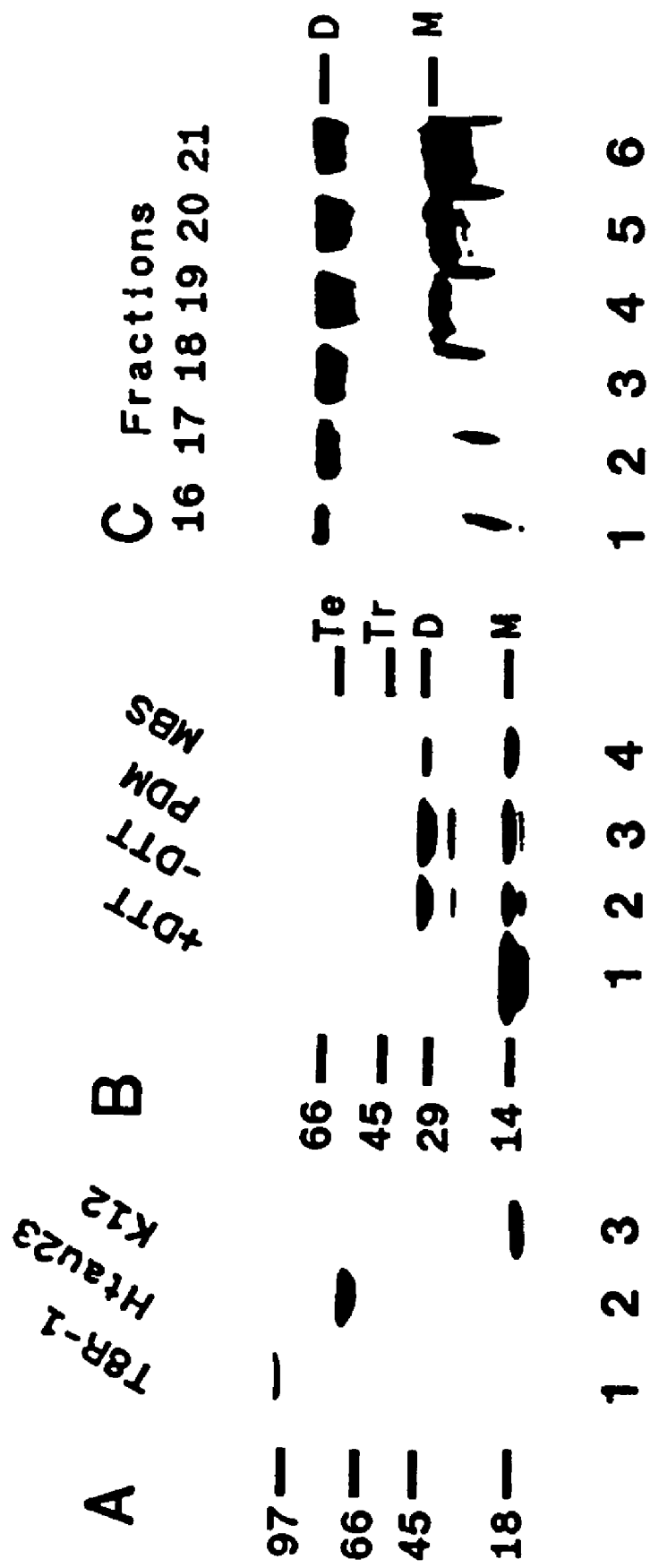
Figure 20D:
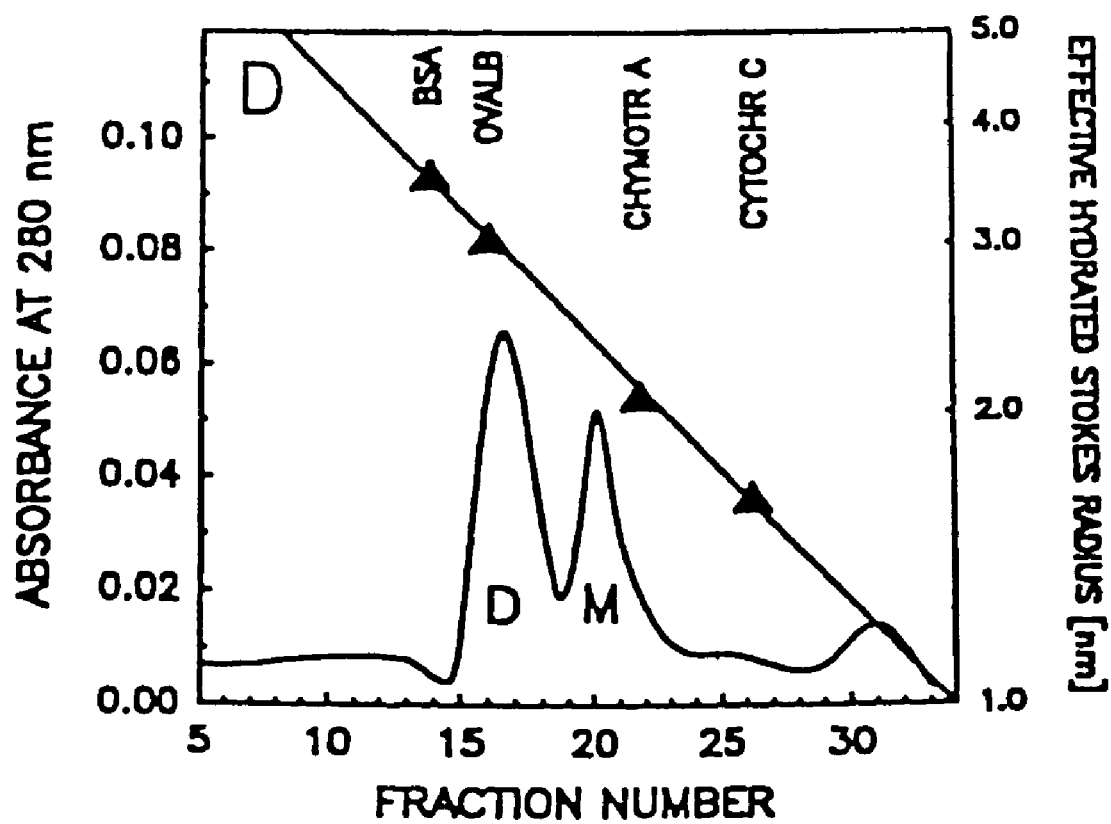
Figure 20E:
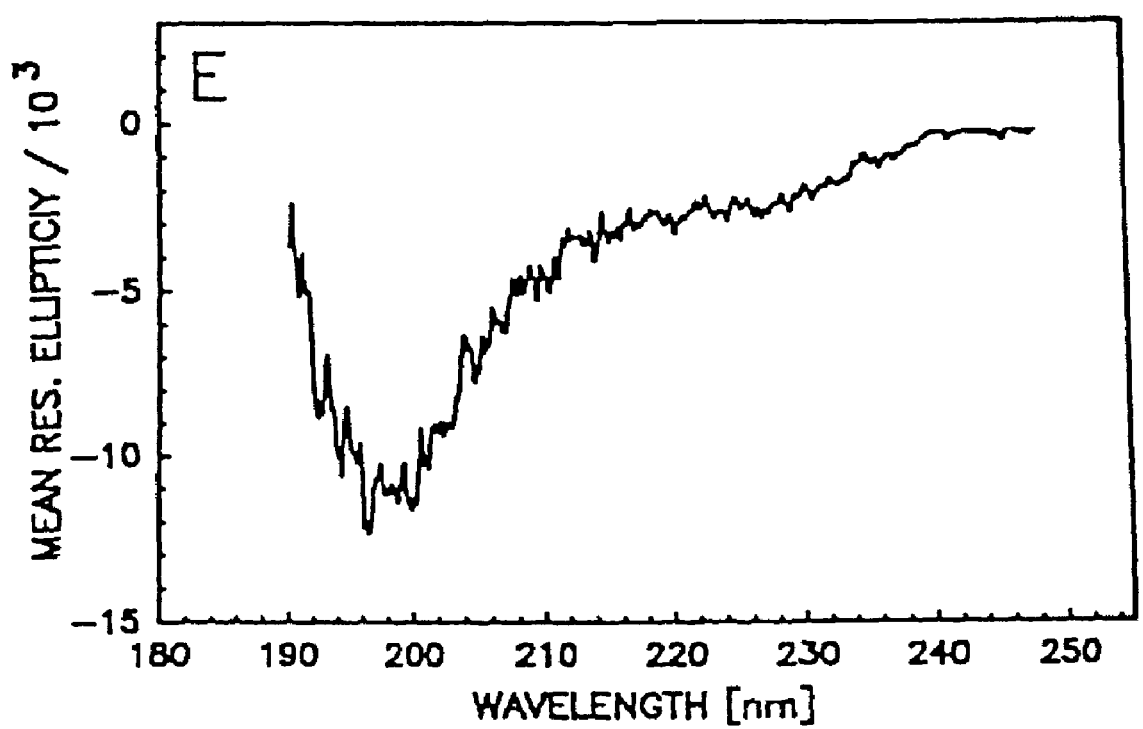

The SDS gels of FIG. 20 illustrate some of these proteins. Most tau constructs have $M_r$ values larger than expected from their actual mass (FIG. 20a). A notable feature is the tendency to form dimers and oligomers. This is particularly pronounced with some constructs, for example K12 (FIG. 20b). The formation of dimers can already be observed by letting the protein stand for some time (FIG. 20b, lane 2), presumably because the dimers become fixed by a disulfide bridge; this can be prevented by DTT (lane 1). To test this, the cross-linker PDM which predominantly links cysteines was used. This generates essentially the same products as in the absence of DTT (lane 3). Chemical cross-linking of construct K12 (2–5 mg/ml) was carried out by incubation in 40 mM HEPES pH 7.5 with 0.5 mM DTT for 30 min at 37° C. and followed by reaction for 30 min at room temperature with 0.7 mM PDM (Sigma) or 1.5 mM MBS (Pierce) added from freshly prepared stock solutions in DMSO. The reactions were quenched by addition with 5 mM DTT or 5 mM DTT and 5 mM ethanolamine, respectively. Finally, dimers and higher oligomers can also be generated by MBS, which links cysteines and lysines (lane 4). The cross-linked species can be separated by chomatography on a Superose 12 column (FIG. 20c), allowing the study of a homogeneous population of dimers. For this purpose, the covalently cross-linked dimers were separated from the monomers by gel filtration on a Pharmacia Superose 12 FPLC column equilibrated and eluted with 50 mM Tris-HCL pH 7.6 containing 0.5 M NaSCN, 0.5 M LiCl and 2 mM DTT operated at a flow rate of 0.3 ml/min. Column fractions were analysed by SDS-PAGE, pooled and concentrated by centrifugation through centricon 3 microconcentrators (Amicon). The column was calibrated with the proteins from the Pharmacia low molecular weight gel filtration calibration kit. Effective hydrated Stokes radii (r) of the calibration proteins were taken from the kit's instruction manual and partition coefficients ($\sigma$) were determined from the elution volumes and fitted to an equation of the form $\sigma=-A \log r+B$, yielding the Stokes radii for the tau construct monomers and dimers. The axial ratios were calculated following Perrin (for further details, see Cantor & Schimmel, Biophysical chemistry, Part II: Techniques for the study of biological structure and function. Freeman & Co, San Francisco, 1980) The elution profile (FIG. 20d) yields Stokes radii of 2.5 nm for the monomer of K12, and 3.0 nm for the dimer. Given the molecular weights of 13 and 26 kDal this yields axial ratios of 10 and 8, consistent with the rod-like shape observed by electron microscopy (the equivalent lengths of prolate ellipsoids would be 6.8 and 8.5 nm which underestimates the actual lengths; see below).

Other tau species show similar cross-linking results, but they are somewhat more complex for the following reason: Tau has cysteines only in repeats 2 and 3 (residues Cys291 and Cys322). Repeat 2 is absent from some isoforms, for example htau 23 or construct K12, leaving only the lone Cys322. With Cys-Cys cross-linkers such as PDM, these molecules can only form dimers, but no higher aggregates (FIG. 20b, lane 3). In contrast, bivalent molecules with two cysteines (such as htau40, K11) can form intramolecular cross-links, dimers and higher oligomers. This diversity is similar to what is found after cross-linking K12 with MBS (FIG. 20b, lane 4) because tau contains many lysines.

The conformation of several tau constructs in solution was probed by analytical ultracentrifugation and CD spectroscopy according to standard procedures. For example, htau40 had a sedimentation constant of 2.6S on the mixture of tau from brain. For a globular particle of the mass of htau40 (45.8 kDal) one would expect $\approx$4.2S; the lower observed value indicates an elongated structure with a hydrodynamic axial ratio of $\approx$15. The CD spectra of htau40 and construct K12 (FIG. 20e) were indistinguishable; they showed very little secondary structure. This means that both the N-terminal and C-terminal domains of tau lack internal regularity such a $\alpha$-helix or $\beta$-sheet.

(b) Synthetic Paired Helical Filaments.

Figure 23B:
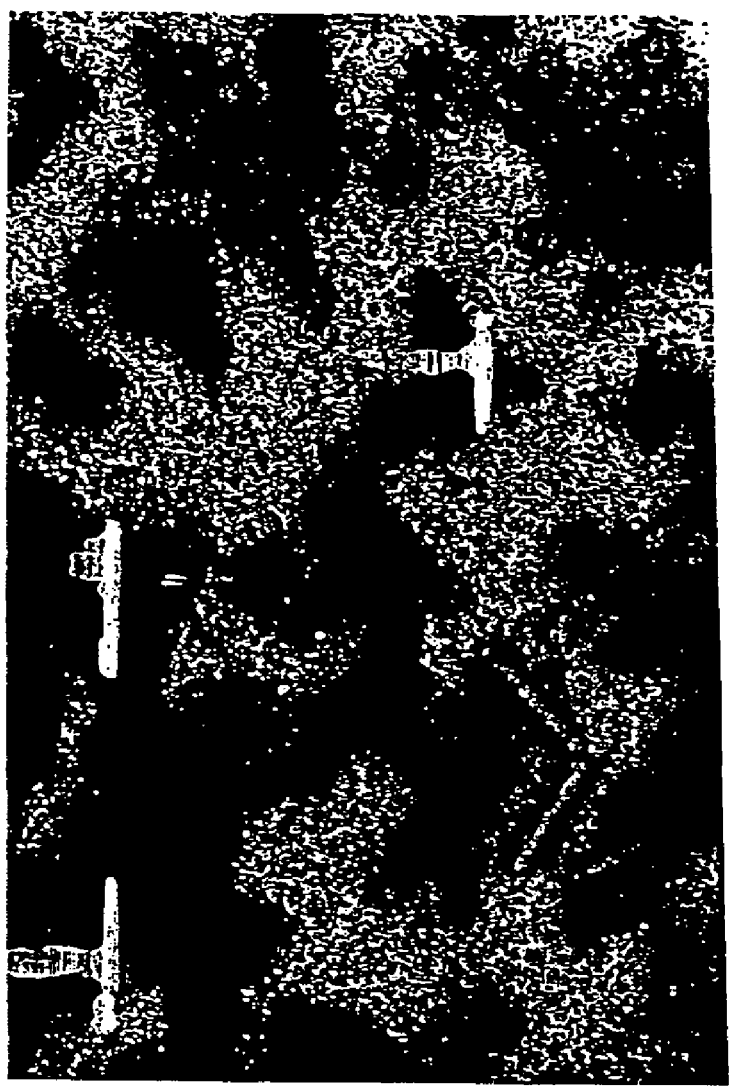
Figure 23A:
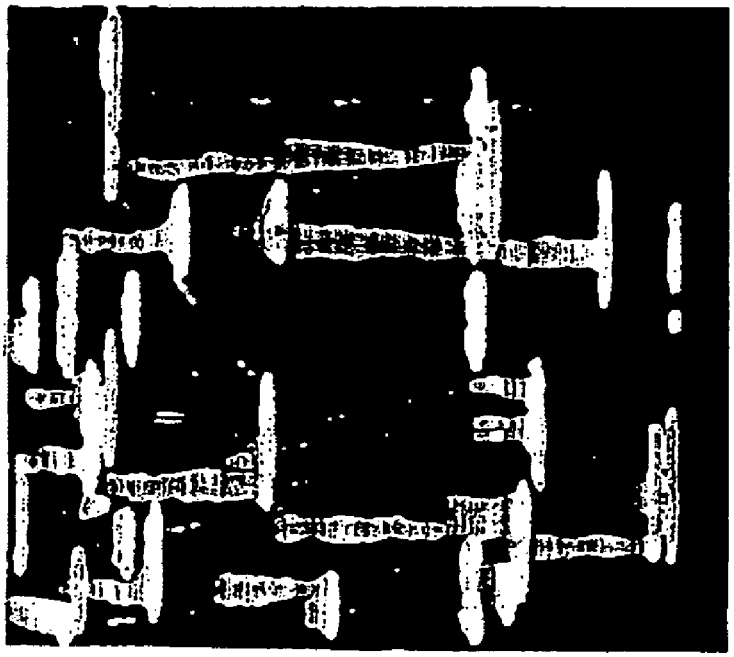

Tau isolated from brain tissue can self-assemble into fibrous structures (see e.g. Montejo de Garcini & Avila, J. Biochem. 102 (1987), 1415–1421; Lichtenberg-Kraag & Mandelkow, J. Struct. Biol. 105 (1990), 46–53). This property became particularly interesting in view of the fact that tau is one of the main components of the neurofibrillary tangles of Alzheimer's disease. In the earlier studies the relationship of the filaments formed in vitro to the Alzheimer PHFs remained ambiguous, especially since the protein was heterogeneous. It was therefore desirable to check if recombinant tau constructs were capable of self-assembly. This was tested in a variety of conditions of pH, salt buffer type, etc. Typically, solutions of tau constructs or chemically cross-linked dimers were dialyzed against various buffers (e.g. ≈50–500 mM MES, Tris-HCl, Tris-maleate, pH values 5–9, 5–30 mM $MgCl_2$, $CaCl_2$, $AlCl_3$) for 12–24 hours at 4° C. The solution was briefly centrifuged (Heraeus Biofuge A, 1 min, 10,000 g) and the pellet was stored for several days at 4° C. and then processed for negative stain electron microscopy (2% uranyl acetate or 1% phosphotungstic acid). Alternatively the solution was used for grid dialysis on gold grids following Van Bruggen et al., J. Microsc. 141 (1986), 11–20. of the constructs tested only K11 and K12 yielded filaments resembling PHFs. The optimal conditions were 0.3–0.5 M Tris-HCl and pH 5.0–5.5, and without any additional salts. The results obtained with construct K12 are illustrated in FIG. 21. In the pH range of 5.0–5.5 there was extensive formation of filaments. Their length was variable, but typically in the range of 200–1000 nm. Most appeared rather smooth, others showed a regular variation of width, with axial periodicities around 70–75 nm (arrowheads). The minimum diameter was about 8 nm and the maximum around 15 nm. Short rod-like particles, about 80–150 nm in length were also observed, which appeared to represent just one or two crossover periods of the filaments (FIG. 21, middle). It was not possible to discern reliably any axial fine structure that might indicate an arrangement of protein subunits. This was therefore either below the resolution limit of negative stain, and/or due to lack of contrast. In general the filaments tended to be bundled up in clusters, as if they had a high affinity for one another (FIG. 21a). Similar PHF-like filaments were also obtained with K12 dimers cross-linked with PDM (FIG. 22). This suggests that the dimer might be an intermediate stage in filament assembly. Many of these features are similar to those of paired helical filaments isolated from Alzheimer's disease brains, shown for comparison in FIG. 23. Their appearance depends somewhat on the isolation procedure. FIG. 5a shows "insoluble" filaments prepared from neurofibrillary tangles after Wischik et al., J. Cell Biol. 100 (1985), 1905–1912. These filaments are long, straight, and have a homogeneous ultra-structure characterized by the distinct ≈75 nm repeat. By contrast, when the filaments are "solubilized" by sarkosyl following Greenberg & Davies, Proc. Natl. Acad. Sci. USA 83 (1990), 5827–5831, they are shorter and less homogeneous (FIG. 23b). In particular, this preparation includes very short particles (equivalent to about 1–2 crossover periods), and smooth filaments that do not have the twisted appearance (reminiscent of straight filaments). There is a striking similarity between the synthetic PHFs based on the repeat domain (e.g. K11, K12, K12 dimers, FIG. 21, 22) with the soluble PHFs from Alzheimer brains (FIG. 23b), judged by three different criteria: (i) The filaments are shorter than the insoluble PHFs of FIG. 23a; (ii) they are less homogeneous in their periodicity, and some lack the twisted appearance altogether (straight filaments), (iii) they include very short rod-like particles, down to the length of one crossover period.

Thus far, synthetic PHF-like fibers have only been observed with constructs such as K12 and K11 containing essentially the repeat domain (3 or 4 repeats, FIG. 19), but not with larger tau isoforms. These data are all consistent with the assumption that the repeat domain is the basic unit that is capable of self-assembling into PHFs very similar to those of Alzheimer neurofibrillary tangles. This also agrees with experiments in several laboratories showing that the pronase-resistant core of Alzheimer PHFs contains the repeat region (e.g. Goedert et al., ibid., Jakes et al., EMBO J. 10 (1991), 2725–2729). It was also noted that the filament-forming constructs were not phosphorylated so that this does not, in contrast to the genuine Alzheimer PHF, play a role in self-assembly here.

(c) Electron Microscopy of Tau Monomers and Dimers.

The results on the synthetic PHFs suggested that the repeat region had a special role in the interaction between tau molecules. It was therefore desirable to define their structure in more detail by comparing different constructs in the electron microscope. The method of choice was metal shadowing at a very shallow angle, combined with glycerol spraying; this helps to make the particles visible which otherwise would not be seen because of their low contrast. Spraying was done following Tyler & Branton, J. Ultrastruct. Res. 71 (1980), 95–102. The samples were diluted 1:10 in spraying buffer (50 mM ammonium acetate pH 8.0, 150 mM NaCl, 1 mM $MgCl_2$, 0.1 mM EGTA), made up to 70% glycerol and sprayed onto freshly cleaved mica. The sprayed samples were vacuum dried for 2 hours, shadowed with platinum/carbon (thickness about 1.5 nm, shadowing angle 4°) using a BAE 080T shadowing unit (Balzers Union), followed by 20–30 nm carbon. Finally the replicas were floated off on doubly distilled water and picked up with 600 mesh copper grids.

Molecules of htau23 (352 residues, FIG. 24a) are rod-like and have a mean length of 35±7 nm (lengths summarized in Table 2 and FIG. 25). This value is less than that reported by Hirokawa et al., J. Cell Biol. 107 (1988), 1449–1459, but this might be due to differences in the experimental approach (freezing vs. glycerol spraying; a mixture of all isoforms vs. the smallest isoform). The apparent width of the metal shadowed htau23 molecules is about 3–5 nm, and the contrast is low—much less than that of control samples (single and double stranded DNA, α-helical proteins). Careful inspection of the micrographs reveals a population of particles with enhanced contrast, somewhat larger diameter (5–7 nm), sometimes split into two parts, and lengths similar or slightly more than the monomer (around 40 nm). These particles are interpreted as (nearly) juxtaposed monomers forming dimers (FIG. 24b), consistent with the results on cross-linked dimers and antibody decoration shown later.

Figures 25B, 25D, 25F, 25H:
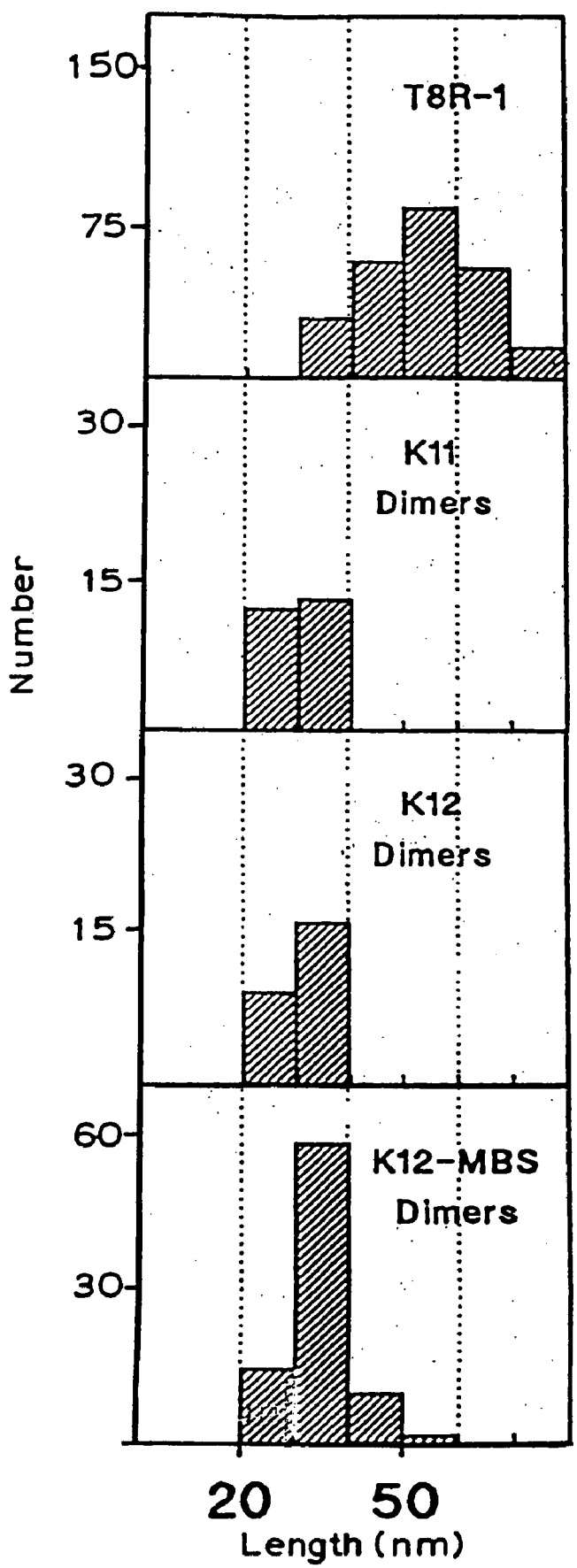

Clearly longer particles are obtained with the construct T8R-1 which average 58+15 nm, 23 nm more than htau23 (FIGS. 24c, 25b). This construct contains eight repeats (a duplication of the four basic ones, FIG. 19), that is five repeats more than htau23, plus the two 29-mer inserts near the N-terminus. T8R-2 has a similar length (61±17 nm), even though it lacks the N-terminal inserts. Construct T7R-2 also has a similar length of 60±16 nm, even though it has only seven repeats (3+4) and no N-terminal inserts. At first sight these results appear puzzling: on the one hand, larger constructs become longer, but on the other hand certain parts of the sequence do not affect the length. Anticipating the results below, the contradiction can be explained by a unifying hypothesis: The length of the tau constructs is determined mainly by the repeat region; by comparison, the N-terminal domain and the C-terminal tail are only of minor influence. The repeat region itself must be considered a unit, roughly 20–25 nm long, whose length is approximately independent of the second repeat. The hypothesis implies that the N-terminal inserts have only a minor influence on the length. It predicts that constructs with 3 or 4 repeats have roughly the same length (e.g. T7R vs. T8R), and that the addition of one repeat domain adds about 20–25 nm in length (as in htau23 vs. T7R or T8R).

T8R and other constructs also form particles folded into a hairpin (FIG. 24d), as if the two "units" (of four repeats each in this case) could interact; this is suggestive of an antiparallel arrangement, supporting the antibody data described infra. T8R particles were also observed whose width and contrast indicate dimers similar to htau23 (FIG. 24e).

Figure 26A:
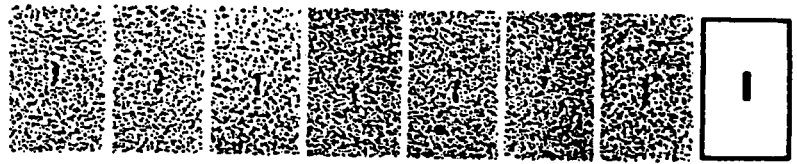
Figure 26B:
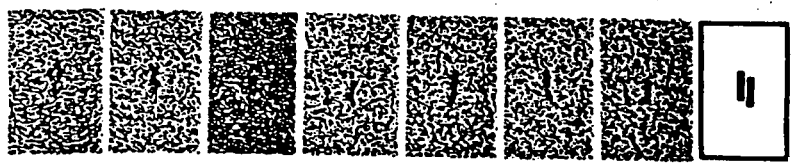
Figure 26C:
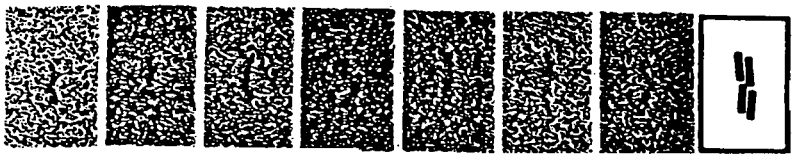
Figure 26D:
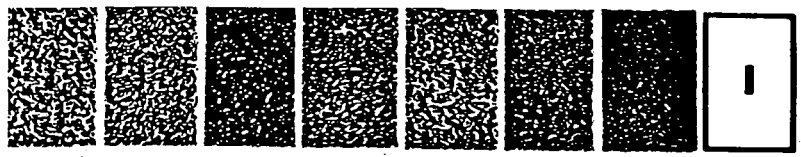
Figure 26E:
Figure 26F:
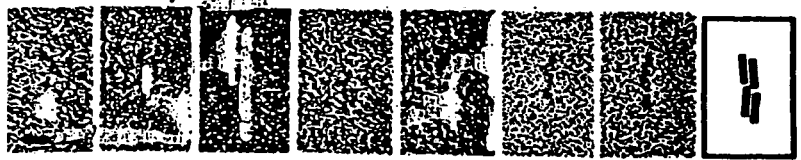

As in the previous cases, the repeat domain constructs that form the PHF-like fibers formed by K11 and K12 described above (FIG. 26) are rod-like. Using the criteria of thickness or contrast and the comparison with the dimers, K11 displays a population of low contrast monomers with a mean length of 26±5 nm (FIG. 26a), and a population of more contrasty dimers, about 32±6 nm (FIG. 26b). This means that the two molecules must be juxtaposed for most of their length. For K12, monomers of length 25±4 nm, (FIG. 26d), and dimers of about 30±4 nm (FIG. 26e) are found. The monomers have about 70–75% of the length of htau23, although they contain only a third of the residues (FIG. 25c, e). With both constructs, longer particles are found which are interpreted as dimers associated into tetramers (FIG. 26c, f).

Thus far the classification into monomers and dimers was judged by relating the width and contrast of the particles to model structures. However, it is possible to isolate the covalently cross-linked dimers by gel chromatography and study them directly by electron microscopy and other methods. As an example, dimers of K12 cross-linked by PDM via the single Cys322 (FIG. 27a) are shown. In the electron microscope, their contrast is similar to the dimers described above; but more importantly, they are only slightly longer than the monomers (29±6 nm FIG. 27a, FIG. 25e, g). This means that the PDM dimers are formed by two molecules lying next to one another and nearly in register. The dimers of K12 induced by MBS (34±6 nm) are also similar, except that they tend to be somewhat longer (by ≈5 nm) than those obtained with PDM, probably because a greater variety of Cys-Lys bonds are possible (FIGS. 27b, 25h).

Taken together, the results obtained with K11 and K12 (and other constructs containing essentially the repeat domain) are consistent with the hypothesis that the repeat domain forms a folding unit of rather uniform length, independently of whether it contains 3 or 4 repeats.

For all constructs tested, the glycerol spray experiments show a certain tendency to form fibrous structures. In most cases, they are rather uniform in diameter, they show no obvious relationship to paired helical filaments and may result from a distinct pathway of self-assembly.

(d) Antiparallel Alignment of Dimers

It is clear from the above data that tau and its constructs tend to align laterally into dimers. This raised the question of polarity: Are the particles parallel or antiparallel? First indications came from the hairpin fold observed with the 8-repeat constructs (e.g. FIG. 24d), suggesting antiparallel orientations of the two halves. Direct evidence for this was obtained by labeling with the monoclonal antibody 2–4 whose epitope is on the last repeat and therefore close to the C-terminus in terms of the sequence (Dingus et al., J. Biol. Chem. 266 (1991), 18854–18860). FIG. 28a (left) shows particles of htau23 with one antibody molecule bound. The antibodies bind at or near one end, showing that one of the physical ends of the rod coincides roughly with the C-terminus. The lengths of the rod portions shown are similar to those of unlabeled htau23; in terms of apparent width, they could be monomers or dimers. In the same fields, one also finds doubly labeled particles (FIG. 28a, right). The antibodies bind at opposite ends, proving that the two subunits of a dimer have opposite polarities.

The same features are found with construct K12; rodlike stubs with an antibody at one end (FIG. 28b, left); dumbells, i.e. antiparallel dimers (FIG. 28b, middle). Finally, there are particles with two antibodies and two stubs, with a kink in the middle (pairs of "cherries," FIG. 28b, right). Each of the arms has roughly the length of a unit stub so that the particles appear equivalent to the tetramers of FIG. 26c and f. The interaction between the diners at the center appears to prevent the binding of an antibody which could otherwise be expected there.

PDM dimers of construct K12 (formed by Cys322-Cys322 crosslinks) are shown in FIG. 28c. Particles with one antibody label are on the left, doubly labeled ones in the middle, showing that the chemically crosslinked dimer consists of antiparallel monomer. A presumptive tetramer is on the right. Essentially the same data are obtained with MBS crosslinked dimers (Cys322 to nearby Lys, FIG. 28d).

Based on the knowledge described in this Example, in vitro methods for testing drugs effective in dissolving Alzheimer paired helical filaments as for testing drugs effective in the reduction or prevention of the formation of Alzheimer paired helical filaments may be developed, as is described above.

EXAMPLE 10

Effect of Glycogen Synthase Kinase-3 (GSK-3) and cdk2-cyclin A on Phosporylation of the Tau Protein Experiments described in Examples 4 and 5 were repeated using GSK3 (also referred to as phosphatase activating factor $F_A$, Vandenheede et al., J. Biol. Chem. 255 (1980), 11768–11774) as the phosphorylating enzyme.

GSK3 ($\alpha$ and $\beta$ isoforms) were purified from bovine brain as described in Vandenheede et al., ibid., with an additional Mono S chromatography step which separates the two isoforms. Most experiments described here were done with immunoprecipitates of GSK-$\alpha$ on TSK beads (following Van Lint et al., Analyt. Biochem. 1993, in press), but control experiments with the $\beta$ subunits showed the same behavior.

Polyclonal anti-peptide antibodies to the $\alpha$ and $\beta$ isoforms of GSK3 were raised in rabbits and affinity purified on peptide columns. Immunoprecipitates of GSK3 were prepared from PC-12 cytosols in 20 mM Tris-HCl, 1% NP-40, 1 mM PMSF, 2 µg/ml aprotinin, 1 µg/ml leupeptin and 0.2 µg/ml pepstatin. 100 µl of cytosols were incubated with 1 µl of $\alpha$- or $\beta$-GSK antibodies (1 mg/ml) or control rabbit antibodies and incubated for 4 h at 4° C., 5 µl of TSK-protein A beads were added and incubated for another hour, and finally the beads were washed with 10 mg/ml BSA in 20 mM Tris-HCl, 0.5 M LiCl in Tris buffer, and 20 mM Hepes pH 7.2 with 10 mM $MgCl_2$ and 1 mM DTT. In phosphorylation assays, 2 µl of pellets were incubated with 8 µl of substrate (3 µM) in 40 mM Hepes pH 7.2, 10 mM $MgCl_2$, 2 mM ATP, 2 mM EGTA, 0.5 mM DTT and 1 mM PMSF.

(a) Time Course of Phosphorylation and Antibody Response Induced by GSK3

FIG. 29 shows a time course of phosphorylation of htau40 with GSK3, and the corresponding autoradiogram and immunoblots. In most respects the behavior is similar to that obtained with the brain kinase activity or with purified MAP kinase. Phosphorylation induces a gel shift in three main stages; it incorporates ≈4 P$_i$; it induces the reactivity of antibodies AT8, SMI34, and SMI31, but reduces the reactivity of TAU1 and SMI33.

(b) Phosphorylation Sites of GSK3 on Tau

The main phosphorylation sites can be determined from antibody epitopes and point mutants (FIG. 29). TAU1 requires that both Ser199 and Ser202 are unphosphorylated, AT8 requires them both phosphorylated. Thus when only one of the two serines is phorphorylated these antibodies do not react. This means that Ser199 and Ser202 both become phosphorylated during stage 2 (FIG. 29, panels 3,4). Similarly, antibody SMI31 requires the phosphorylation of both Ser396 and Ser404, which means that both serines become phosphorylated rapidly during stage 1 (FIG. 29, panel 6). SMI33 reacts only when Ser235 is unphosphorylated so that the gradual loss of reactivity means that this residue becomes phosphorylated only slowly (panel 7). Together these residues would account for 5 Pi, but only ≈4 Pi were observed by autoradiography, indicating that not all of these serines are phosphorylated at 100%. There are some subtle differences in the time course of immune response, compared to MAP kinase. For example, the SMI31 reactivity sets in early and precedes that of AT8 and SMI34, while the reactivity of SMI33 persists for a longer time, indicating that the mode of action of GSK3 is not identical to that of MAP kinase.

Additional information can be obtained by point mutations. As shown in Examples 5 and 6, the initial strong mobility shift induced by the kinase activity from brain extracts and by MAP kinase is due to the phosphorylation of Ser404. The same is true for GSK3, as illustrated in FIG. 30 (lanes 1–3). When Ser404 is mutated into Ala, the initial rapid shift disappears, and initial phosphorylation is reduced to a low level (FIG. 30, compare lanes 2 and 5).

Another conclusion from the immunoblots is that GSK3 strongly prefers Ser-Pro motifs, in contrast to MAP kinase which also affects Thr-Pro. This follows since the ≈4 Pi incorporated are needed to account for the phosphorylated epitopes. To test this construct AP11 was prepared, a derivative of htau23 where all 6 Ser-Pro are replaced with AlaPro (FIG. 31, middle). AP11 is phosphorylated only to a minimal extent, <0.1 Pi per molecule, confirming that the Thr-Pro motifs remain largely unphosphorylated. The same result is obtained with construct AP17 (all 6 Ser-Pro and 8 Thr-Pro replaced by Ala-Pro, FIG. 31, top). Another construct, K18 containing only the four repeats (FIG. 31, bottom), is also not phosphorylated, indicating that no major sites are within the microtubule binding region. Thus, GSK3 and MAP kinase are similar in that they are both proline directed, but MAP kinase is also active with respect to Thr-Pro motifs.

(c) GSK3 and MAP Kinase are Associated with Microtubules and with PHPs

Figures 32A, 32B, 32C, 32D:
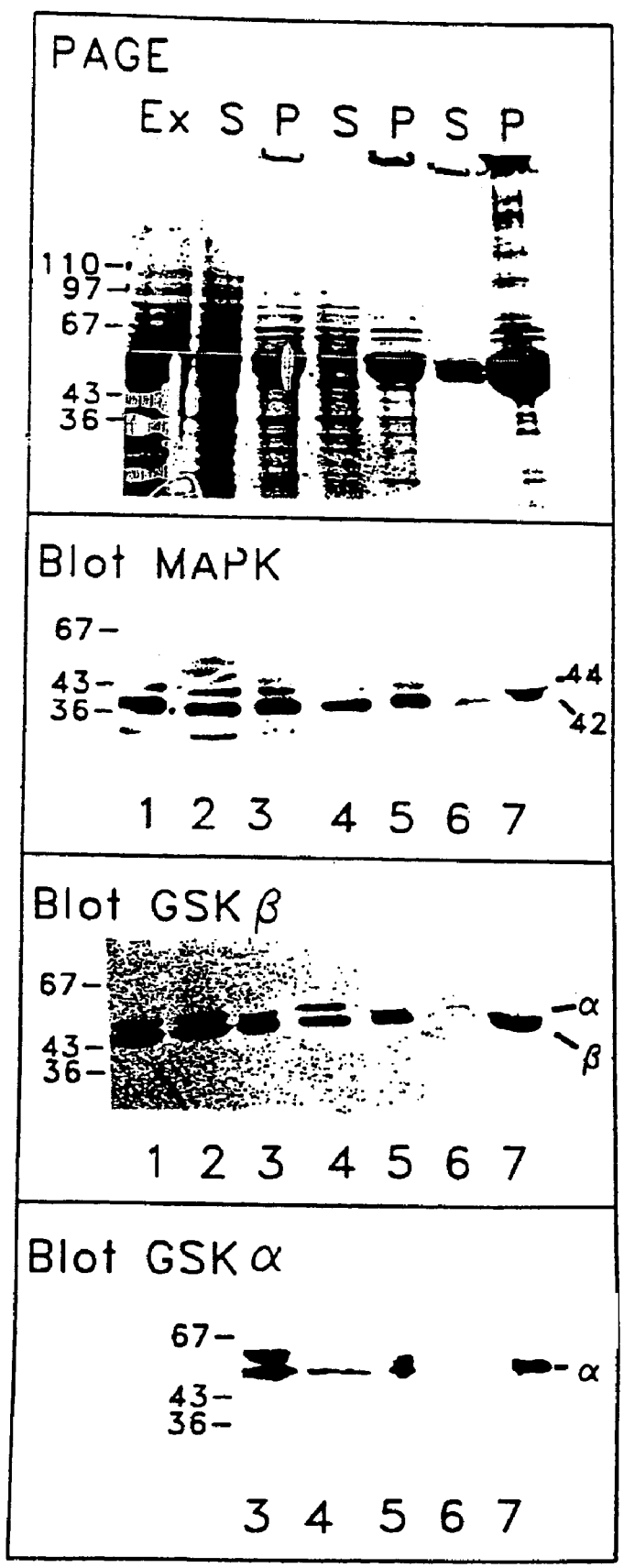

Considering that tau is a microtubule-associated protein one might expect that kinases that phosphorylate tau might be localized in the vicinity. It was therefore tested whether MAP kinase or GSK3 were microtube-associated proteins according to the usual criterium of co-purification through repeated circles of assembly and disassembly. This was indeed the case. FIG. 32b shows that both the p42 and p44 isoforms of MAP kinase co-purified with porcine brain microtubules, FIG. 32c, d demonstrates the same for the case of GSK3 α and β. Interestingly, the microtubule-associated MAP kinase was not in an activated state since it was not phosphorylated on Tyr (as judged by immunoblotting, not shown).

Considering this result, it was of interest to investigate whether the kinases were also associated with Alzheimer PHFs. The immunoblots of FIG. 33a demonstrate that GSK3 is present in normal and in Alzheimer brain in roughly equivalent amounts and thus resembles MAP kinase in this respect. Moreover, the kinases co-purify directly with PHFs isolated by two different procedures, following Wischik et al., J. Cell. Biol. 100 (1985), 1905–1912 (FIG. 33b, lane 1) and Wolozin et al., Science 232 (1986), 648–650 (lane 2).

The fact that GSK3 is associated with microtubules and PHFs and phosphorylates tau would suggest that the kinase might be able to affect the interaction between tau and microtubules. This would be in agreement with a common notion about the pathological effects of tau phosphorylation. Surprisingly, however, there was no influence on the binding. FIG. 34 shows the binding of htau23 to microtubules without phosphorylation, with phosphorylation by GSK3, and by the kinase activity of the brain extract. In the latter case, there is a strong reduction in affinity, but the effect of GSK3 itself is minimal.

(d) Phosphorylation of Tau by cdk2-cyclin A

The protein kinase cdk2-cyclin A (a proline-directed ser/thr kinase; see Hunter, ibid.) induces the Alzheimer-like state, as judged by phosphorylation, gel shift and antibody response. The kinase cdk2 incorporated 3.5 Pi into htau40 and generated a similar shift in the gel as MAP kinase and GSK-3. The antibodies AT-8, SMI31, SMI34 recognize the phosphorylated tau, TAU-1 and SMI33 do not, again similar to MAP kinase and GSK-3. All ser-pro motifs (Ser 199, 202, 235, 396, 405, 422) can be phosphorylated to some extent; see FIG. 46.

The preparation was as follows: Cells overproducing the cdk2/cyclin A complex were obtained by Dr. Piwnica Worms, Boston.

Cyclin A was fused to glutathione-S-transferase. Thus, the complex is easily purified using glutathione agarose beads as outlined below:

Kinase Assays on Glutathione Beads:

3×10$^6$ cells were infected with viruses encoding human p33$^{cdk2}$ and human cyclin A (fused to glutathione-S-transferase) each at an m.o.i. of 10. At 40 hours post infection, cells were rinsed (2×) in PBS. Cells were frozen on plate at −70° C. (Cells are kept frozen until experiments are carried out.)

Preparation of Cell Lysates:
Lyse cells in 1 ml of the following buffer:
50 mM Tris pH 7.4
250 mM NaCl
50 mM NaF
10 mM NaPPi
0.1% NP40
10% glycerol
protease inhibitors (0.15 units/ml aprotinin, 2 mM PMSF, 20 μM leupeptin)

Plates were rocked for 15 min at 4° C., lysates were collected, placed in Eppendorf tube and spun at 10K for 10 min at 4° C. clarified lysates were placed in fresh Eppendorf tube.

Glutathione Precipitation

100 μl (50 % slurry of agarose in PBS) of glutathione agarose (from sigma) were added to the clarified lysate, rocked ≈1 hour at 4° C. and were spun briefly to pellet beads. Beads were washed two times in 1 ml of above lysis buffer and washed two times with incomplete kinase buffer (50 mM Tris pH 7.4, 10 mM $MgCl_2$). As much buffer as possible was removed from the beads after the final wash.

For kinase assays:

Exogenous substrate was added and then complete kinase buffer was added:

50 mM Tris, pH 7.4

10 mM $MgCl_2$ 1 mM DTT

10 µM unlabeled ATP

2 µl of gamma $^{32}$P-labelled ATP (NEN: 3000 Ci/mM) and incubated at 30° C. for the desired amount of time.

EXAMPLE 11

Phosphorylation of Ser 262 of Tau Protein by a Novel Kinase and Effect Thereof on Binding to Microtubules by Tau Proteins So far it has been shown that the Alzheimer-like state of tau protein includes phosphorylation of Ser-Pro and Thr-Pro motifs, and that this state can be mimicked by a brain extract kinase activity and by MAP kinase, as judged by the response with Alzheimer-specific antibodies. As will be demonstrated in the following, a crucial regulation of tau's binding to microtubules occurs at Ser262, a residue phosphorylated by the brain extract activity but not by MAP kinase. A novel kinase from mammalian brain which phosphorylates this residue and thereby strongly reduces the interaction between microtubules and tau protein has furthermore been purified.

Binding studies between tau and taxol-stabilized microtubules were done as described in Example 6. This provides a direct measure of the attachment of tau to pre-formed microtubules and yields dissociation constants and binding stoichiometries (n=$tau_{bound}$/tubulin dimer); the reduction in stoichiometry is the most conspicuous and reproducible parameter. The drop in stoichiometry in a wild type tau isoform upon phosphorylation, $D_{n,wt}=(n_{unphos}-n_{phos})_{wt}$, is taken as 100% and can be compared to the effect of phosphorylation on a mutant. $D_{n,mut}$.

Preparation of the kinase from brain: An extract from 250 g of porcine brain tissue was prepared and submitted to ammonium sulfate precipitation as described in Example 2. The precipitate obtained between 30 and 45% saturation was homogenized in buffer 1 (25 mM Tris-HCl pH 7.4 containing 25 mM NaCl, 2 mM EGTA, 2 mM DTT, 1 mM PMSF) and dialyzed against 1 liter of this buffer with two changes overnight. Total protein concentration was determined using the Pierce BCA assay kit. After clarification of the dialysate by ultracentrifugation, portions of up to 250 mg of protein were loaded on a Mono QHR 10/10 column (Pharmacia) equilibrated with buffer 1. Elution was performed with a linear gradient of 25–500 mM NaCl in 120 ml of buffer 1 with a flow rate of 2 ml/min. Fractions were screened by phosphorylation of bacterially expressed tau and tau constructs as described below. Active peaks were pooled and concentrated 10 to 40-fold by centrifugation through Centriprep 10 microconcentrators (Amicon) and chromatographed on a Superdex 75 HiLoad 16/60 size exclusion column (Pharmacia) equilibrated and eluted with buffer 1 containing 50 mM NaCl. Active fractions were pooled and rechromatographed on a Mono Q HR 5/5 column with a gradient of 0–600 mM NaCl in 30 ml of buffer 1 with a flow rate of 0.5 ml/min. Active fractions were dialyzed against buffer 1 and stored at 0° C. The gel filtration column was calibrated with the Pharmacia low weight marker set. Phosphorylation assays were performed as described (Steiner et al., 1990, ibid.).

In-gel assays of tau phosphorylation were done following Geahlen et al., Anal. Biochem. 153 (1986), 151–158. MonoQ-fractions with kinase activity were subjected to 11% SDS PAGE (0.5 mm thick slab gels). Tau protein was added to the separation gel solution just prior to polymerisation (final concentration 0.1 mg/ml). The following steps were then performed: (1) To remove SDS, the gels were washed with two changes of 20% propanol in 50 mM Tris-HCl pH 8.0 for 30 min at room temperature, then 50 mM Tris-HCl pH 8.0 containing 5 mM β-mercaptoethanol (=buffer A) for another 30 min at RT. (2) The enzyme was denatured by two changes of 6 M guanidine-HCL for 1 hour at room temperature (RT). (3) The enzyme was renatured by five changes of buffer A containing 0.04% Tween 40 for ≈15 hours at 4° C. (4) Pre-incubation with phosphorylation buffer without ATP for 30 min at RT (40 mM Hepes pH 7.5, 5 mM EGTA, 3 mM MgCl, 0.1 mM PMSF, 2 mM DTT). (5) Phosphorylation with added 0.1 mM ATP and 130 Ci/Mol (gamma-32)ATP was performed by incubation of the gel in a plastic bag at 37° C. for 20 hours on a rotating wheel. (6) Removal of excess (gamma-32)ATP: The gel was washed by incubation in five changes of 300–500 ml of 5% TCA containing 1% sodiumpyrophosphate until unbound radioactivity was negligible. (7) Staining and autoradiography were done according to conventional methods.

(a) Phosphorylation of Ser262 Strongly Reduces the Binding of Tau to Microtubules As shown in Example 6, when tau protein is phosphorylated by the brain extract kinase activity, the stoichiometry typically dropped from ≈0.5 tau per tubulin dimer down to ≈0.1–0.15, i.e. about 3–4-fold; this effect on the wild type protein will be taken as 100% in this Example. The parameters affected by phosphorylation have distinct time courses. A major part of the gel shift occurs early (stage 1 phosphorylation, up to ≈2 hours) and can be ascribed to a single site, Ser 404 (numbering of htau40). Most of the Alzheimer-like antibody response, as well as an additional gel shift, sets in during stage 2 (up to ≈6 hours); a further shift combined with more incorporation of phosphate occurs during stage three (up to 24 hours). However, the effect on microtubule binding was already fully visible after stage 1. At this point, the protein bound about two moles of $P_i$ (out of a maximum of ≈5–6). About one of these was at Ser404, identifiable by the first gel shift. The other phosphate was distributed among Ser202, 235, and 262, but exact quantification by autoradiograpghy and phosphopeptide sequencing was difficult.

Figure 35B:
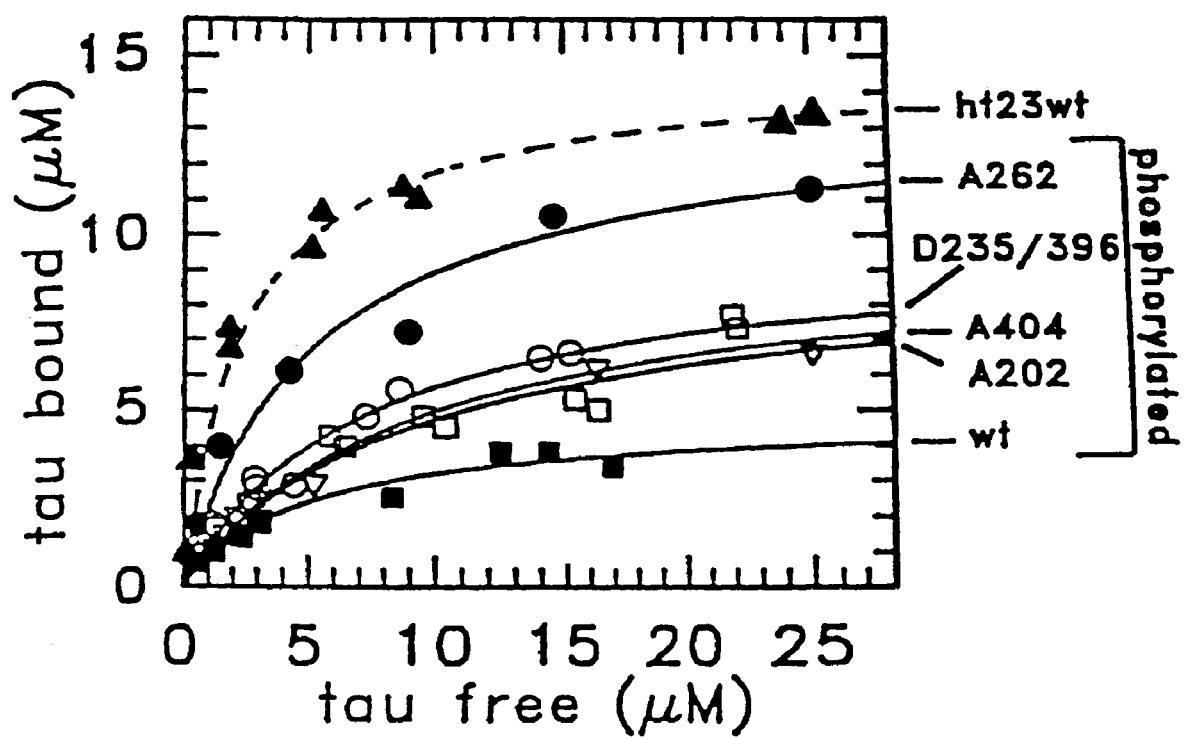

It was therefore decided to approach the problem by site-directed mutagenesis. The Ser residues in question were replaced by Ala (making them non-phosphorylatable) or Asp (mimicking the negative charge of the phosphorylated state; see FIG. 35a). These mutants were then assayed with respect to gel shift, phosphate incorporation, and microtubule binding (FIG. 35b). The mutant Ser404-Ala loses its shift during stage 1 phosphorylation, but the phosphorylation of this protein still has a sizable effect in reducing the microtubule binding capacity (difference in stoichiometry $D_n$=0.17, i.e. 52% of the unmutated control with $D_n$=0.33). This suggests that one or more of the remaining Ser202, 235, and 262 are responsible for a major fraction of the phosphorylation effect on binding. Similar results are obtained when Ser202, 235, and 396 are mutated into Ala or Asp, indicating that neither of these residues accounts for the low stoichiometry after phosphorylation observed with wild type htau23. However, when Ser262 was altered, the binding to microtubules was nearly unaffected by phosphorylation ($D_n=0.04$). In other words, it appears that mutating one residue, Ser262 in the first repeat, nearly eliminates the phosphorylation sensitivity of tau towards microtubule binding; or conversely, phosphorylation of Ser262 reduces the binding of tau to microtubules dramatically.

(b) MAP Kinase Induces the Alzheimer-like Immune Response of Tau but does not Impair Microtubule Binding The binding data in section (a) were obtained with a brain extract, but most of the properties of extract phosphorylation could be induced by purified MAP kinase from Xenopus oocytes or porcine brain. Extract and MAP kinase induce a gel shift, they have a similar time course of phosphorylation, and both induce a similar pattern of antibody responses (including the onset of the "Alzheimer-like" response in stage 2 phosphorylation). The majority of sites found with the extract are in Ser-Pro motifs; all of them are phosphorylated by MAP kinase as well, plus Thr-Pro motifs, i.e. purified MAP kinase is more efficient as a Pro-directed Ser/Thr kinase than the brain extract. Finally, MAP kinase is a major phosphorylating component in the brain extracts.

However, when the effect of highly purified MAP kinase on tau's microtubule binding was tested it turned out to be surprisingly small ($D_n=0.09$) compared with the brain extract ($D_n=0.31$ in FIG. 36). This was consistent with the above experiments, suggesting that phosphorylation of Ser-Pro or Thr-Pro motifs by itself was only of secondary importance with respect to microtubule binding.

Figure 37A:
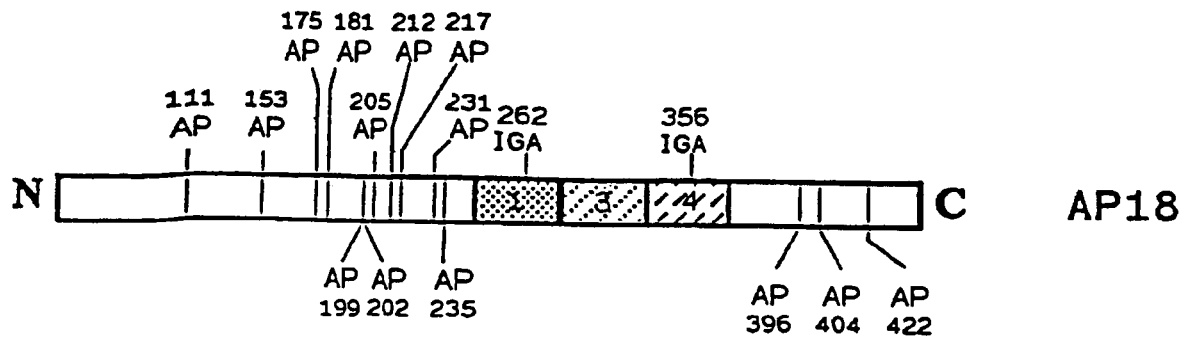

This was tested by employing two "total" mutants, AP17 and AP18 derived from htau23 (FIG. 37a). AP18 is similar to AP17, but in addition Ser262 and 356 (the two serines not followed by Pro found earlier in extract phosphorylations) were changed into Ala. While MAP kinase phosphorylates all Ser-Pro and Thr-Pro sites of wild type htau23 (typically up to a maximum of 10–12 moles of $P_i$ per htau23), AP17 incorporates at most 1.4 $P_i$, illustrating the high specificity of MAP kinase for Ser-Pro or Thr-Pro motifs. AP17 binds tightly to microtubules, independently of phosphorylation by MAP kinase, with similar parameters as unphosphorylated wild type htau23. The same results are obtained with AP18 and MAP kinase (<1 $P_i$ incorporated).

Figure 37B:
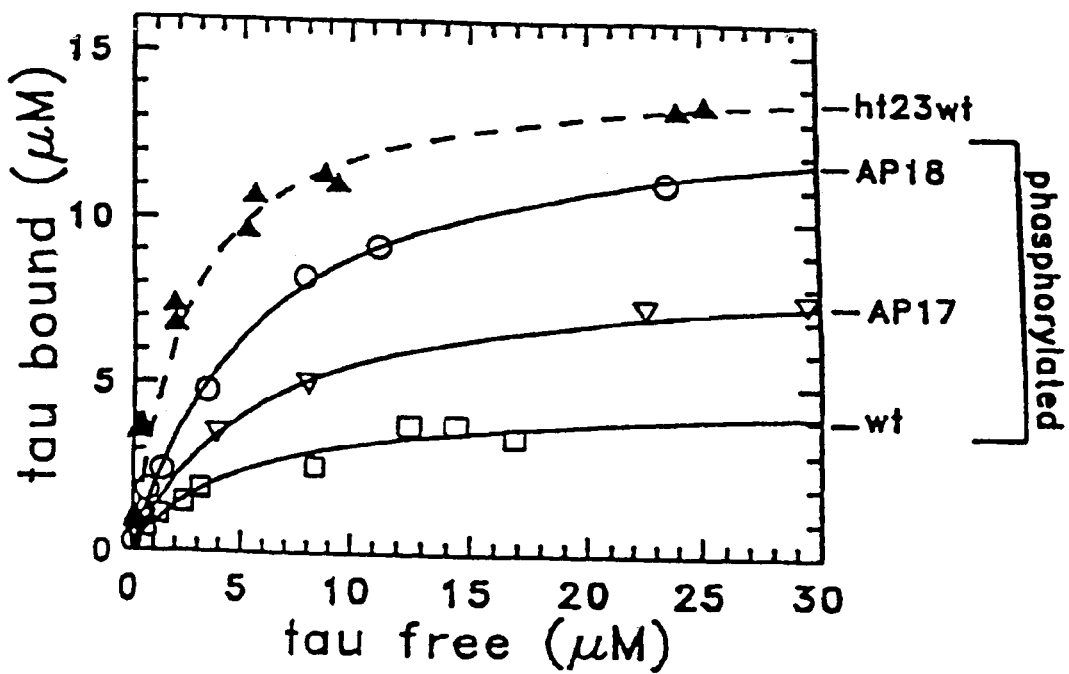

However, when AP17 and AP18 are phosphorylated with the brain extract activity the two mutants are dramatically different (FIG. 37b). AP18 incorporates about 0.5 $P_i$ and shows only a minor reduction of the stoichiometry of tau bound to microtubules upon phosphorylation ($D_n=0.01$). AP17 incorporates ≈1.3 $P_i$, and yet its reduction of the binding of tau to microtubules upon phosphorylation is the same as that of wild type htau23 ($D_n=0.31$).

These results made it clear that the brain extract apparently contains some phosphorylating component distinct from MAP kinase which phosphorylates Ser262 in the first repeat of tau protein, and that this single Ser, when phosphorylated, is capable of dramatically altering the interaction of tau with microtubules. By contrast, MAP kinase affects the other indicators of the Alzheimer state of tau, the gel shift and the immune response.

(c) The 35 kDal and 70 kDal Kinases in Brain Reduces Microtubule Binding by Phosphorylating Ser 262

The sequence around Ser 262 does not fit obvious consensus motifs of known kinases so that it did not seem promising to test them. Instead, the kinase was purified from the brain extract. Active fractions were identified by the criteria of tau phosphorylation and effect on microtubule binding.

Figure 38D:
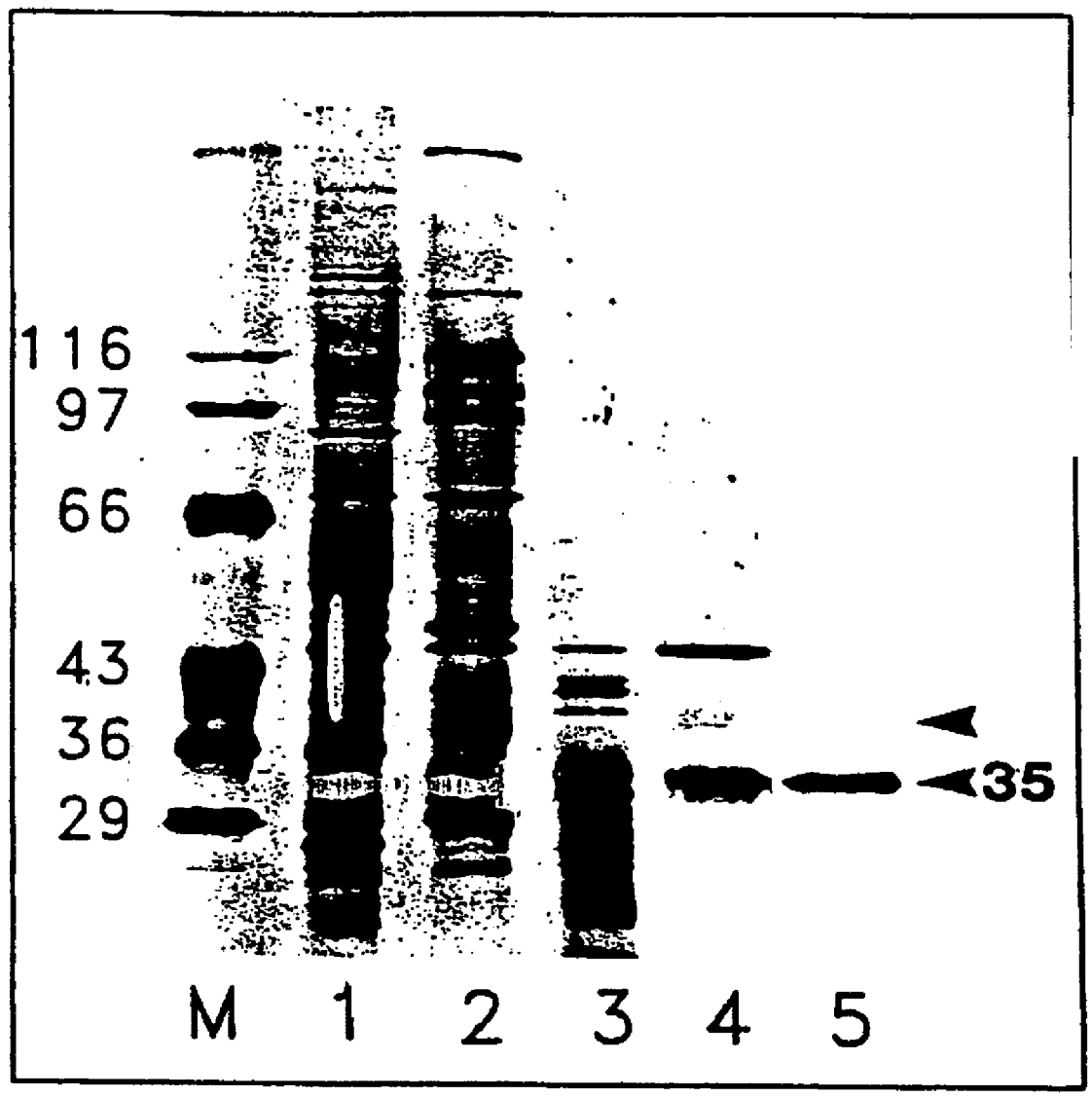

The first step was ion exchange chromatography on Mono Q (FIG. 38a), yielding 3 main peaks of kinase activity. The fractions with the largest effect on microtubule binding were further subjected to gel chromatography (FIG. 38b). The main active fraction eluted at an Mr around 35 kDal. This was followed by another ion exchange run. The protein did not bind to Mono S, suggesting an acidic pI, but it eluted as one major peak on Mono Q (FIG. 38c). Silver stained gels of fraction 9 showed a 35 kDal band with >95% purity, and minor (<5%) bands around 41 kDal (FIG. 38d, lane 5). Other fractions ahd an additional band at ≈45 kDal, but this had no kinase activity (see below).

To determine directly which of the bands in the gel were capable of phosphorylating tau an in-gel assay following the method of Geahlen et al., Anal. Biochem. 153 (1986), 151–158 was performed. Tau protein was polymerized into the gel matrix, the Mono Q fractions were separated on the gel by SDS electrophoresis, the the bound proteins were renatured in situ, incubated with radioactive ATP and assayed for activity by autoradiography. FIG. 39 shows that the 35 kDal and 41 kDal bands contained kinase activity, but not the 45 kDal band.

Quantification of the amount of phosphate incorporated into tau constructs by the kinase yielded the following results: 3.2 $P_i$ for htau34, 3.4 for htau40, 3.3 for htau23, but only 2.8 for the mutant htau23(Ser262→Ala). The total mutant AP17 incorporated 3.0 $P_i$, indicating that Ser-Pro or Thr-Pro motifs were not targets of the kinase, and the 3-repeat construct K18 contained 1.4 $P_i$.

Figure 40A:
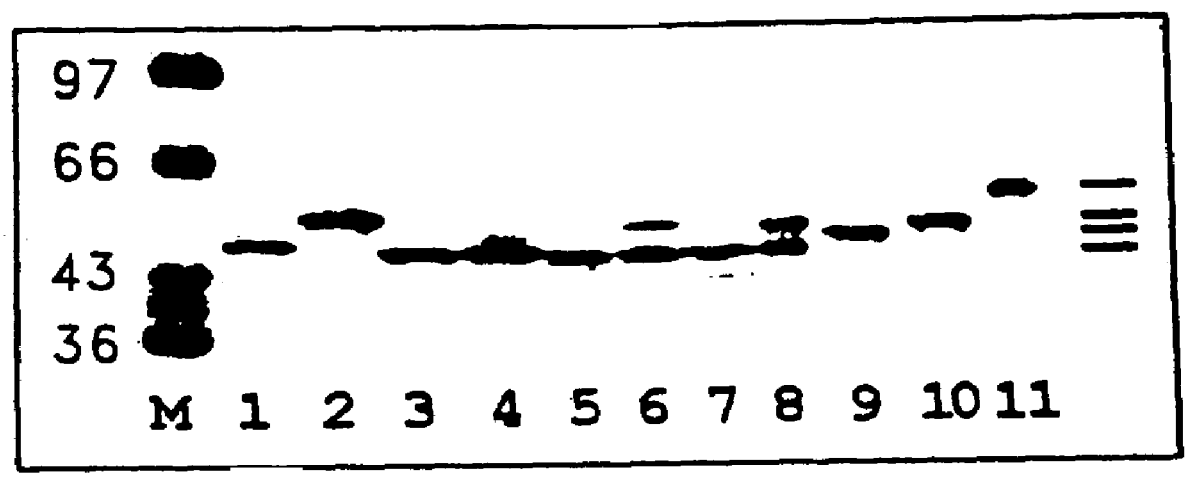
Figure 40B:
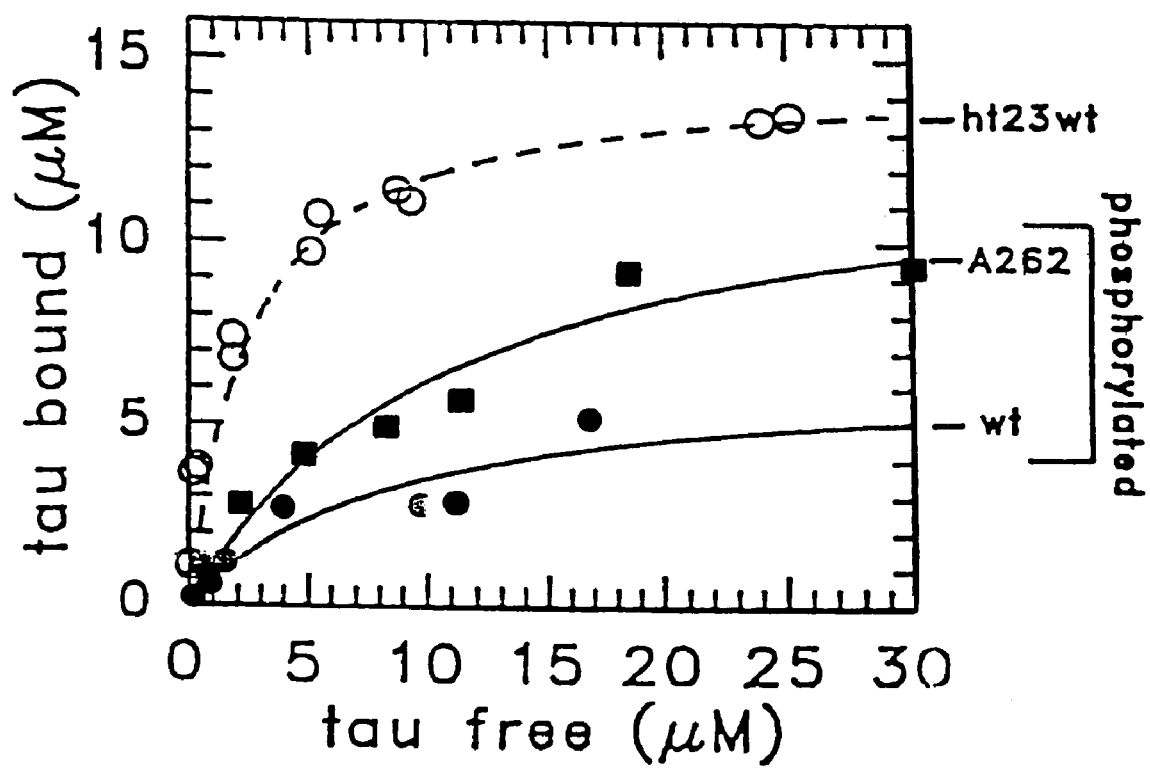

Tau phosphorylated by the kinase is shifted upward in the SDS gel. FIG. 40a shows a comparison of different tau gel shifts and kinases. The shift by the 35 kDal kinase is of medium magnitude (lane 2), like that of PKA (lane 10), larger than that of CaM kinase (lane 9) but distinctly smaller than that of MAP kinase (lane 11) which induces the Alzheimer-like immune response. The mutant Ser409-Ala (lanes 3,4) is not shifted by phosphorylation, but other mutants are (e.g. at Ser416, lanes 5, 6, or at Ser404, lanes 7,8), indicating that Ser49 is the residue whose phosphorylation by the 35 kDal kinase generates the shift. This same shift is found with PKA (lane 10) which also phosphorylates Ser409. Since phosphorylation sites within the repeat region generally do not produce a shift these data confirm that the shift sites (mostly in the C-terminal tail) are distinct from the sites controlling microtubule binding (e.g. Ser262).

The effect of the purified kinase of the binding of tau (FIG. 40b) is similar to that of the brain extract (FIG. 37b). For example, the stoichiometry of htau23 is reduced by $D_n=0.28$ upon phosphorylation, but only by 0.05 in the point mutant Ser262-Ala, again emphasizing the importance of Ser262.

A diagram of htau40, highlighting the first microtubule-binding repeat and the Ser262 that is important for microtubule-binding is depicted in FIG. 41.

A similar effect on the binding of tau to microtubules is observed when tau is phosphorylated by the 70 kDal kinase (see FIG. 45). This kinase incorporates about 3–4 Pi into the repeat region of tau, specifically at serines 262, 293, 324, 409. It is prepared by the following steps: (a) Preparation of high spin supernatant of brain extract. (b) Chromatography on Q-Sepharose. (c) Chromatography of flowthrough on S-Sepharose. Kinase activity elutes at 250 mM NaCl. (d) Chromatography on heparin agarose. Kinase activity elutes at 250 mM NaCl. (e) Gel filtration. Kinase activity elutes at 70 kDal. (f) Chromatography on Mono Q. Kinase activity elutes at 150 mM NaCl.

EXAMPLE 12

Figure 42A:
Figure 42B:
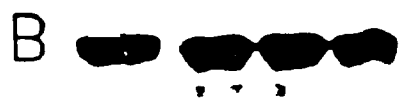
Figure 42C:
Figure 42D:
Figure 43A:
Figure 43B:
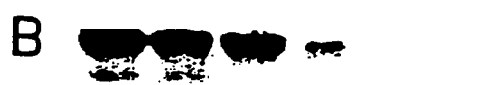
Figure 43C:
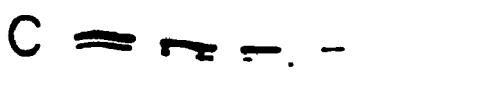
Figure 43D:
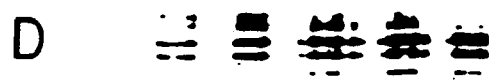
Figure 43E:

Dephosphorylation of Tau Protein by Phosphatases PP2a and PP1 htau 40 was phosphorylated with porcine MAP kinase (p42) and $^{32}$P-ATP according to methods described throughout this specification. Subsequently, htau40 was dephosphoylated with several isoforms of PP2a (FIG. 42 A to C) as PP1 (FIG. 42D). The results show that htau40 is dephosphorylated by all isoforms of PP2a, and, although much slower, by PP1 FIG. 43 shows that upon dephosphorylation the antibody-specific epitopes disappear as well. In FIG. 44 the time course of dephosphorylation and the Michaelis-Menten-kinetics are shown.

Thus, PP2a and PP1 serve as antagonist to MAP-kinases and may therefore be used in pharmaceutical compositions-for the treatment of Alzheimer disease.

TABLE 1

Interactions of tau constructs with antibodies in the phosphorylated or unphosphorylated state (+ or −). The staining on immunoblots ranges from very weak, (x), to very strong, xxx.

| construct | phosph. +/− | SM133 | SM131 | SM134 |
|---|---|---|---|---|
| htau40 | − | xxx | | |
| | + | | xxx | xxx |
| htau23 | − | xxx | | |
| | + | | xxx | xxx |
| K3M | − | | | |
| | + | | (x) | |
| K2 | − | | | |
| | + | | xxx | |
| K17 | − | xxx | | |
| | + | | | xx |
| K10 | − | | | |
| | + | | xxx | xxx |
| K19 | − | | | |
| | + | | | |
| htau40/A235 | − | (x) | | |
| | + | | xxx | xxx |
| htau40/A396 | − | xxx | | |
| | + | | xx | xxx |
| htau40/A235/A396 | − | (x) | | |
| | + | | xx | xxx |

TABLE 1-continued

Interactions of tau constructs with antibodies in the phosphorylated or unphosphorylated state (+ or −). The staining on immunoblots ranges from very weak, (x), to very strong, xxx.

| construct | phosph. +/− | SM133 | SM131 | SM134 |
|---|---|---|---|---|
| htau23/A404 | − | xxx | | |
| | + | | xxx | xxx |
| htau23/A396/A404 | − | xxx | | |
| | + | | | xxx |
| K4 | − | xxx | | |
| | + | | | xx |
| K5 | − | xxx | | |
| | + | | xx | xxx |
| K6 | − | xxx | | |
| | + | | xx | xxx |
| K7 | − | xxx | | |
| | + | | x | xx |
| K13 | − | xxx | | |
| | + | | | xx |
| K14 | − | xxx | | |
| | + | | | xx |
| K15 | − | xxx | | |
| | + | | | xx |

TABLE 2

Summary of lengths of various tan constructs.

| construct | length (nm) | s.d. (nm) | number |
|---|---|---|---|
| htau23 | 35 | 7 | 232 |
| T8R-1 | 58 | 15 | 304 |
| T8R-2 | 61 | 17 | 75 |
| T7R-2 | 60 | 16 | 73 |
| K11 | 26 | 5 | 32 |
| K11 dimer | 32 | 6 | 24 |
| K12 | 25 | 4 | 27 |
| K12 dimer | 30 | 4 | 25 |
| K12 PDM dimer | 29 | 6 | 79 |
| K12 MBS dimer | 34 | 6 | 85 |

The invention claimed is:

1. An isolated antibody that binds phosphorylated tau as set out in SEQ ID NO: 1, wherein the antibody binds a tau epitope comprising a serine residue only when the serine residue is phosphorylated, said serine residue consisting of.

2. The antibody of claim 1, wherein the antibody is a $F_{ab}$ fragment.

3. The antibody of claim 1, wherein the antibody is a monoclonal antibody.

4. A hybridoma that produces an antibody of claim 3.

5. A method of detecting a phosphorylated tau protein as set out in SEQ ID NO: 1 comprising
   (a) contacting a sample comprising a tau protein with an antibody that binds phosphorylated tau according to claim 1; and
   (b) detecting binding of the antibody to phosphorylated tau protein.

* * * * *

UNITED STATES PATENT AND TRADEMARK OFFICE
CERTIFICATE OF CORRECTION

PATENT NO. : 7,176,290 B2
APPLICATION NO. : 10/066810
DATED : February 13, 2007
INVENTOR(S) : Eva-Maria Mandelkow et al.

It is certified that error appears in the above-identified patent and that said Letters Patent is hereby corrected as shown below:

On the Title Page:

At Item (30), "91 12 0974" should be -- 91 12 0974.0 --.

At Item (30), "92 11 9551" should be -- 92 11 9551.7 --.

In the Claims:

At Column 47, line 14, claim 1, "residue only" should be -- residue 262 of SEQ ID NO: 1 only --.

At Column 47, line 15, Claim 1, "said serine residure consisting of" should be -- and wherein the antibody does not bind tau epitope when the serine is not phosphorylated --.

Signed and Sealed this

Seventeenth Day of June, 2008

JON W. DUDAS
*Director of the United States Patent and Trademark Office*